(12) United States Patent
Smallheer et al.

(10) Patent No.: US 11,059,818 B2
(45) Date of Patent: *Jul. 13, 2021

(54) TRIAZOLOPYRIDINE INHIBITORS OF MYELOPEROXIDASE

(71) Applicant: BRISTOL-MYERS SQUIBB COMPANY, Princeton, NJ (US)

(72) Inventors: Joanne M. Smallheer, Yardley, PA (US); Carol Hui Hu, New Hope, PA (US); Meriah Neissel Valente, Bedminster, NJ (US); Scott A. Shaw, Lawrence Township, NJ (US); Benjamin P. Vokits, New York City, NY (US); Oz Scott Halpern, Robbinsville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 266 days.

This patent is subject to a terminal disclaimer.

(21) Appl. No.: 16/083,951

(22) PCT Filed: Mar. 10, 2017

(86) PCT No.: PCT/US2017/021807
§ 371 (c)(1),
(2) Date: Sep. 11, 2018

(87) PCT Pub. No.: WO2017/160632
PCT Pub. Date: Sep. 21, 2017

(65) Prior Publication Data
US 2020/0291015 A1     Sep. 17, 2020

Related U.S. Application Data

(60) Provisional application No. 62/307,723, filed on Mar. 14, 2016.

(51) Int. Cl.
*C07D 471/04* (2006.01)

(52) U.S. Cl.
CPC ................... *C07D 471/04* (2013.01)

(58) Field of Classification Search
CPC .................................. C07D 471/04
See application file for complete search history.

(56) References Cited

U.S. PATENT DOCUMENTS 10,214,527 B2 *   2/2019   Shaw .................. A61P 25/00
10,407,422 B2 *   9/2019   Smallheer ........... A61P 29/00
2018/0282320 A1  10/2018   Shaw et al.

FOREIGN PATENT DOCUMENTS

WO    WO 2017/040449 A1    3/2017

OTHER PUBLICATIONS

Schönherr "Profound Methyl Effects in Drug Discovery and a Call for New C-H Methylation Reactions" Angew. Chem. Int. Ed. 2013, 52, 12256-12267.*
Patani "Bioisosterism: A Rational Approach in Drug Design" Chemical Reviews 1996, 96, 3147-3176.*
Wermuth, Camille G. "Molecular Variation Based on Isosteric Replacements" in Chapter 13, The Practice of Medicinal Chemistry, Academic: 1996.*
Nakamura, Toshio "Imidazole derivatives as new potent and selective 20-HETE synthase inhibitors." Bioorganic & Medicinal Chemistry Letters 2004, 14, 333-336.*
Li, Bing et. al. "N-(Arylacetyl)-biphenylalanines as Potent VLA-4 Antagonists" Bioorganic & Medicinal Chemistry Letters 2002, 12, 2141-2144.*

* cited by examiner

*Primary Examiner* — David K O'Dell
(74) *Attorney, Agent, or Firm* — Elliott Korsen; Shrikant M. Kulkarni

(57) ABSTRACT

The present invention provides compounds of Formula (I). wherein A and Z are as defined in the specification, and compositions comprising any of such novel compounds. These compounds are myeloperoxidase (MPO) inhibitors and may be useful for the treatment and/or prophylaxis of atherosclerosis, heart failure, chronic obstructive pulmonary disease (COPD), and related diseases.

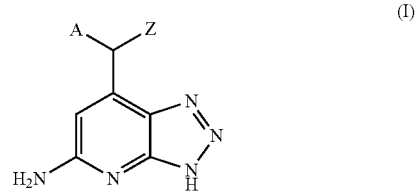

(I)

5 Claims, No Drawings

TRIAZOLOPYRIDINE INHIBITORS OF MYELOPEROXIDASE

CROSS REFERENCE TO RELATED APPLICATION

This application claims priority to U.S. Provisional Patent Application Ser. No. 62/307,723, filed Mar. 14, 2016, which is incorporated by reference in its entirety.

FIELD OF THE INVENTION

The present invention relates to novel triazolopyridine compounds, which are myeloperoxidase (MPO) inhibitors, compositions containing them, and methods of using them, for example, for the treatment and/or prophylaxis of atherosclerosis, heart failure, chronic obstructive pulmonary disease (COPD), and related diseases.

BACKGROUND OF THE INVENTION

Cardiovascular disease is a major health risk throughout the industrialized world. Atherosclerosis, the most prevalent of cardiovascular diseases, is the principal cause of heart attack and stroke, and thereby the principal cause of death in the United States. Atherosclerosis is a complex disease involving many cell types and molecular factors (for a detailed review, see Weber et al., Nature Med, 17(11):1410-1422 (2011)).

MPO inhibitors have been suggested to reduce the atherosclerotic burden and/or the vulnerability of existing atherosclerotic lesions and thereby decrease the risk of acute myocardial infarction, unstable angina or stroke, and reduce ischemia-reperfusion injury during acute coronary syndrome and ischemic cerebrovascular events. Several lines of data support a role for MPO in atherosclerosis. MPO is expressed in the shoulder regions and necrotic core of human atherosclerotic lesions and active enzyme has been isolated from autopsy specimens of human lesions (Daugherty, A. et al., J. Clin. Invest., 94(1):437-444 (1994)). Moreover, HOCl-modified lipoproteins have been detected in advanced human atherosclerotic lesions (Hazell, L. J. et al., J. Clin. Invest., 97:1535-1544 (1996)). In eroded and ruptured human lesions, as compared to fatty streaks, an increased number of MPO expressing macrophages have been demonstrated, suggesting a particular role for MPO in acute coronary syndromes (Sugiyama, S. et al., Am. J. Pathol. 158(3):879-891 (2001); Tavora, F. R., BMC Cardiovasc. Disord., 9:27 (Jun. 23, 2009)).

Data accumulated during the last fifteen years indicate that the pro-atherogenic actions of MPO include oxidation of lipoproteins, induction of endothelial dysfunction via consuming nitric oxide and destabilization of atherosclerotic lesions by activation of proteases (Nicholls, S. J. et al., Arterioscler. Thromb. Vasc. Biol., 25(6):1102-1111 (2005); Nicholls, S. J. et al., JLR, S346-S351 (2009)). Several studies have focused on nitro- and chlorotyrosine modifications of LDL and HDL lipoproteins. Since chlorotyrosine modifications in vivo are generated by hypochlorous acid produced by MPO these modifications are regarded as specific markers of MPO activity (Hazen, S. et al., J. Clin. Invest., 99(9):2075-2081 (1997)).

ApoA-I isolated from atherosclerotic lesions is modified by reactive chlorine and nitrogen species as well as by reactive carbonyls (Pennathur, S. et al., J. Biol. Chem., 279:42977-42983 (2004); Shao, B. et al., J. Biol. Chem., 279:7856-7866 (2004); Zheng, L. et al., J. Clin. Invest., 114(4):529-541 (2004); Shao, B. et al., JBC in press (2012)). Chlorotyrosine modification of apoA1, the main apolipoprotein of HDL cholesterol, was associated with impaired cholesterol acceptor function (Bergt, C. S. et al., Proc. Natl. Acad. Sci. USA, 101(35):13032-13037 (2004); Zheng, L. et al., J. Clin. Invest., 114(4):529-541 (2004)). Thus, oxidation of apoA-I amino acid residues by the MPO-$H_2O_2$—Cl$^-$ system is one mechanism for loss of its biological activities.

The lipid and protein content of LDL are also targets for MPO oxidation and presence of chlorotyrosine in LDL extracted from human atherosclerotic tissues has been shown (Hazen, S. et al., J. Clin. Invest., 2075-2081 (1997)). LDL particles exposed to MPO in vitro become aggregated, leading to facilitated uptake via macrophage scavenger receptors and foam cell formation (Hazell, L. J. et al., Biochem. J., 290 (Pt. 1):165-172 (1993); Podrez, E. A. et al., J. Clin. Invest. 105:1095-1108 (2000)). Thus, MPO appears to play a role in the generation of oxidized LDL, which contributes to atherosclerosis plaque development.

Further evidence implicating MPO in the pathophysiology of atherosclerosis comes from the study of hMPO transgenic mice crossed with LDL-R KO mice (Castelini L. W. et al., J. Lipid Res., 47:1366-1377 (2006)). These mice expressed MPO in lesions and developed significantly larger aortic lesions than control LDL-R KO mice.

Many clinical studies have implicated MPO in cardiovascular disease in human patients. Patients with established coronary artery disease have higher plasma and leukocyte MPO levels than healthy controls (Zhang, R. et al., JAMA, 286(17):2136-2142 (2001)). Moreover, in three large prospective studies plasma levels of MPO predicted the risk of future coronary events or revascularization (Baldus, S. et al., Circulation, 108(12):1440-1445 (2003); Brennan, M. et al., N. Engl. J Med., 349(17):1595-1604 (2003); Kohli, P. et al., Circulation, 122:A13175 (2010)). In two recent large nested case control prospective studies, the EPIC-Norfolk and MONICA-/KORA Augsburg studies, baseline MPO levels in these initially healthy populations turned out to be an excellent predictor of future risk of CAD and CHD respectively, showing that this inflammatory marker precedes the presentation of clinical symptoms of CVD (Meuwese, M. C. et al., J. Am. Coll. Cardiol., 50:159-165 (2007); Karakas et al., J. Int. Med., 271:43-50 (2011)). Interestingly, MPO deficient humans are less affected by cardiovascular disease than controls with normal MPO levels (Kutter, D. et al., Acta Haematol., 104:10-15 (2000)). A polymorphism in the MPO promoter affects expression leading to high and low MPO expressing individuals. In three different studies the high expression genotype has been associated with an increased risk of cardiovascular disease (Nikpoor, B. et al., Am. Heart J., 142(2):336-339 (2001); Makela, R. et al., Lab. Invest. 83(7):919-925 (2003); Asselbergs, F. W. et al., Am. J. Med., 116(6):429-430 (2004)).

MPO inhibitors are expected to preserve heart function and reduce heart failure burden in patients. In MPO null mice, preservation of left ventricular (LV) function has been observed in both a coronary artery ligation model (Askari, A. T. et al., J. Exp. Med., 197:615-624 (2003)) and an ischemia reperfusion model (Vasilyev, N. et al., Circulation, 112:2812-2820 (2005)), suggesting that MPO may provide a mechanistic link between inflammation, oxidant stress, and impaired cardiac remodeling. High circulating levels of MPO have also been linked to chronic heart failure in patients. Systemic MPO was increased in patients with established chronic systolic HF and correlated with diastolic dysfunction independent of age and plasma B-type natriuretic peptide (Tang, W. H. et al., Am. J. Cardiol., 98:796-

799 (2006)). Studies also showed that systemic MPO in subjects with myocardial infarction (MI) (Mocatta, T. J. et al., *J. Am. Coll. Cardiol.*, 49:1993-2000 (2007)) or chronic systolic HF (Tang, W. H. et al., *J. Am. Coll. Cardiol.*, 49:2364-2370 (2007)) may predict long-term adverse clinical events.

Inhibitors of MPO may be used to treat other neuroinflammatory diseases, including multiple sclerosis, Alzheimer's disease, Parkinson's disease, multiple system atrophy, and stroke as well as other inflammatory diseases or conditions like asthma, COPD, cystic fibrosis, inflammatory bowel disease, chronic kidney disease, renal glomerular damage and rheumatoid arthritis.

In these chronic inflammatory diseases, a role of MPO in the development of tissue injury has been suggested. In lesional tissues of patients with Alzheimer's disease, MPO protein was detected along with elevated levels of chlorotyrosine (Green, P. S. et al., *J. Neurochem.*, 90:724-733 (2004)). In an animal model of Parkinson's disease, increased levels of chlorotyrosine and HOCl-modified proteins in brain tissues have been reported (Choi, D. K. et al., *J. Neuroscience*, 25(28):6394-6600 (2005)). In asthmatic patients the level of bromotyrosine, a molecular fingerprint of eosinophil-catalyzed oxidation was associated with symptom severity (Wedes, S. H. et al., *J. Pediatr.*, 248-255 (2011)). Upon allergen challenge, a model that elicits primarily a strong eosinophilic response, lung segments of asthmatic subjects exhibit a >10 fold increase in bronchioalveolar lavage 3-bromotyrosine an indicator of eosinophil activity vs. a 3-fold increase in 3-chlorotyrosine characteristic of MPO activity (Wu, W. et al., *JCI*, 105:1455-1463 (2000)). The presence of HOCl-modified protein was also detected in patients with membranous glomerulonephritis (Grone et al., *Lab. Invest.*, 82:5-14 (2002)). High MPO circulating levels have been implicated in the development of cardiovascular and chronic kidney disease in patients on hemodialysis (Honda, H. et al., *Clin. J Am. Soc., Nephrol.*, 142-151 (2009). In addition MPO activity and 3-chlorotyrosine levels were also increased during hemodyalisis in patients with end-stage renal disease (Delporte, C et al., *Talanta*, 99:603-609 (2012)). Similarly, there is accumulation of neutrophils and eosinophils in conjunction with MPO and EPX seen in intestinal mucosa of patients with inflammatory bowel disease (Kruidenier, L. et al., *J Pathol.*, 201:17-27 (2003); Carlson, M. et al., *Am. J. Gastrol.*, 94(7):1876-1883 (1999)) and in synovial fluids of rheumatoid arthritis patients (Edwards, S. W. et al., *Biochem. J.*, 250:81-85 (1988); Nucombe, H. L. et al., *Ann. Rheum. Dis.*, 50:237-242 (1991)).

Thus, there is considerable evidence that MPO derived oxidants contribute to tissue injury in chronic inflammatory disorders. MPO inhibitors are anticipated to reduce the levels of oxidants and tissue injury associated with the progression of these diseases.

SUMMARY OF THE INVENTION

The present disclosure provides novel triazolopyridine compounds, including stereoisomers, tautomers, pharmaceutically acceptable salts, or solvates thereof, which are useful as MPO inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of diseases or disorders associated with the activity of MPO.

The compounds of the invention may be used in therapy.

The compounds of the invention may be used for the manufacture of a medicament for the treatment and/or prophylaxis of diseases or disorders associated with the activity of MPO.

Examples of diseases or disorders associated with the activity of MPO include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

I. Compounds of the Invention

In a first aspect, the present invention provides a compound of Formula (I):

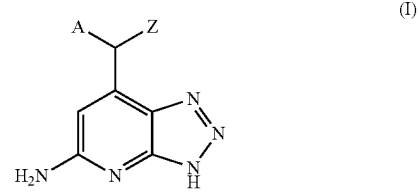

wherein:

Z is $C_1$-$C_6$ alkyl, $C_1$-$C_6$ alkoxyalkyl, $C_3$-$C_8$ cycloalkyl $C_1$-$C_6$ alkyl-, hydroxy $C_1$-$C_6$ alkyl-, aryl $C_1$-$C_6$ alkyl-, aryl $C_1$-$C_6$ alkoxy $C_1$-$C_6$ alkyl-, aryl $C_1$-$C_6$ alkyl $NR^z$ $(CH_2)_2$—, heteroaryl $C_1$-$C_6$ alkyl-, aryl $C_3$-$C_8$ cycloalkyl $NR^z$ $(CH_2)_2$—, aryl $C_3$-$C_8$ cycloalkyl $C_1$-$C_6$ alkyl-, bridged $C_6$-$C_{10}$ carbocyclyl $NR^z(CH_2)_2$—, heterocyclyl $C_1$-$C_6$ alkyl-, or $C_9$-$C_{10}$ bicyclic carbocyclyl $NR^z$ $(CH_2)_2$—, any of which is substituted with 0-3 $R^2$ groups;

$R^z$ is hydrogen, $C_1$-$C_4$ alkyl, $C_1$-$C_4$ haloalkyl, $C_1$-$C_4$ alkoxy $C_1$-$C_4$ alkyl-, —$C_1$-$C_4$ alkyl $CONH_2$ or hydroxy $C_2$-$C_4$ alkyl;

$R^2$ is, independently at each occurrence, one or more halogen, hydroxy, cyano, hydroxy $C_1$-$C_6$ alkyl, halo $C_1$-$C_6$ alkyl, $C_1$-$C_6$ alkyl, —$C_{3-6}$ cycloalkyl, aryl, aryloxy, aryl $C_1$-$C_6$ alkyl-, $CONR^xR^y$;

said —$C_{3-6}$ cycloalkyl substituted with 0-3 $R^a$, aryl substituted with 0-4 $R^a$, and 5- to 10-membered heterocycle comprising carbon atoms and 1-4 heteroatoms selected from N, O, and S; wherein said heterocycle is substituted with 0-3 $R^a$;

$R^a$ is, independently at each occurrence, OH, CN, —CONH$_2$, halogen, C$_{1-4}$ alkyl, C$_{1-4}$ alkoxy, C$_{1-4}$ haloalkyl, or C$_{1-4}$ haloalkoxy;

$R^x$ is hydrogen or C$_{1-4}$ alkyl;

$R^y$ is hydrogen or C$_{1-4}$ alkyl;

A is pyrazole, triazole, pyridine or dihydropyridinone optionally substituted with $R^1$;

$R^1$ is hydrogen, halogen, C$_1$-C$_6$ alkyl, C$_1$-C$_6$ alkoxy, aryl C$_1$-C$_6$ alkyl-, halo C$_1$-C$_6$ alkyl-, heterocyclyl C$_1$-C$_6$ alkyl- or C$_3$-C$_8$ cycloalkyl, any of which is substituted with 0-4 $R^3$ groups;

$R^3$ is, independently at each occurrence, one or more halogen, hydroxy, cyano, hydroxy C$_1$-C$_4$ alkyl, halo C$_1$-C$_4$ alkyl, halo C$_1$-C$_4$ alkoxy, C$_3$-C$_6$ cycloalkyl, aryl, aryloxy, aryl C$_1$-C$_4$ alkyl-, —COO C$_1$-C$_4$ alkyl, CONR$^x$R$^y$, —CO-heterocyclyl, —SO$_2$-aryl or SO$_2$-heteroaryl;

or a pharmaceutically acceptable salt, a stereoisomer, a tautomer, or a solvate thereof, In a second aspect, the present invention provides within the scope of the first or second aspect, a compound of Formula (II) of the formula

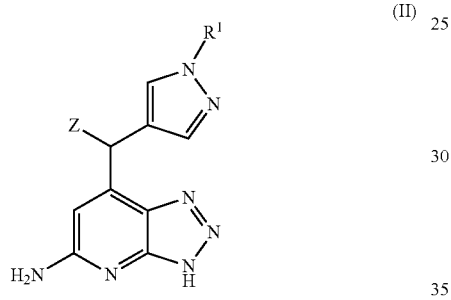

(II)

Z is C$_1$-C$_6$ alkyl, C$_1$-C$_6$ alkoxy C$_1$-C$_6$ alkyl, C$_3$-C$_8$ cycloalkyl C$_1$-C$_6$ alkyl-, hydroxy C$_1$-C$_6$ alkyl-, aryl C$_1$-C$_6$ alkyl-, aryl C$_1$-C$_6$ alkoxy-, aryl C$_1$-C$_6$ alkoxy C$_1$-C$_6$ alkyl-, aryl C$_1$-C$_6$ alkyl NR$^z$ alkyl-, heteroaryl C$_1$-C$_6$ alkyl-, aryl C$_3$-C$_8$ cycloalkyl NR$^z$ C$_1$-C$_6$ alkyl-, aryl C$_3$-C$_8$ cycloalkyl C$_1$-C$_6$ alkyl-, bridged carbocyclyl NR$^z$ C$_1$-C$_6$ alkyl- or heterocyclyl C$_1$-C$_6$ alkyl-, any of which is substituted with 0-3 $R^2$ groups;

$R^z$ is hydrogen, C$_1$-C$_4$ alkyl, C$_1$-C$_4$ haloalkyl, C$_1$-C$_4$ alkoxy C$_1$-C$_4$ alkyl-, —C$_1$-C$_4$ alkyl CONH$_2$ or hydroxy C$_1$-C$_4$ alkyl;

$R^2$ is, independently at each occurrence, one or more halogen, hydroxy, cyano, hydroxy C$_1$-C$_6$ alkyl, halo C$_1$-C$_6$ alkyl, C$_1$-C$_6$ alkyl, —C$_{3-6}$ cycloalkyl, aryl, aryloxy, aryl C$_1$-C$_6$ alkyl-, —COO C$_1$-C$_6$ alkyl, CONR$^x$R$^y$, —CO-heterocyclyl, —SO$_2$-aryl or SO$_2$-heteroaryl;

said —C$_{3-6}$ cycloalkyl substituted with 0-3 $R^a$, aryl substituted with 0-4 $R^a$, and 5- to 10-membered heterocycle comprising carbon atoms and 1-4 heteroatoms selected from N, O, and S; wherein said heterocycle is substituted with 0-3 $R^a$;

$R^a$ is, independently at each occurrence, OH, CN, —CONH$_2$, halogen, C$_{1-4}$ alkyl, C$_{1-4}$ alkoxy, C$_{1-4}$ haloalkyl, or C$_{1-4}$ haloalkoxy;

$R^x$ is hydrogen or C$_{1-4}$ alkyl;

$R^y$ is hydrogen or C$_{1-4}$ alkyl;

$R^1$ is hydrogen, C$_1$-C$_6$ alkyl, C$_1$-C$_6$ alkoxy, aryl C$_1$-C$_6$ alkyl-, halo C$_1$-C$_6$ alkyl-, heterocyclyl C$_1$-C$_6$ alkyl- or C$_3$-C$_8$ cycloalkyl, any of which is substituted with 0-4 $R^3$ groups;

$R^3$ is, independently at each occurrence, one or more halogen, hydroxy, cyano, hydroxy C$_1$-C$_4$ alkyl, halo C$_1$-C$_4$ alkyl, halo C$_1$-C$_4$ alkoxy, C$_3$-C$_6$ cycloalkyl, aryl, aryloxy, aryl C$_1$-C$_4$ alkyl-, —COO C$_1$-C$_4$ alkyl, CONR$^x$R$^y$, —CO-heterocyclyl, —SO$_2$-aryl or SO$_2$-heteroaryl;

or a pharmaceutically acceptable salt, a stereoisomer, a tautomer, or a solvate thereof, In a third aspect, the present invention includes a compound of Formula (II), or a pharmaceutically acceptable salt, a stereoisomer, a tautomer, or a solvate thereof, within the scope of the first aspects, wherein:

Z is Me, propyl, 3-phenylpropyl, 2-benzyloxyethyl, 3,3-diphenylpropyl, 3-cyclohexylpropyl, 1-naphthylpropyl, 2-naphthylpropyl, 1-indanylpropyl, 2-(tetrahydro-2H-pyran-4-yl)ethyl, 2-phenoxyethyl, 3-(1,2,3,4-tetrahydroisoquinolin-1-yl)propyl, 2-benzylaminoethyl,

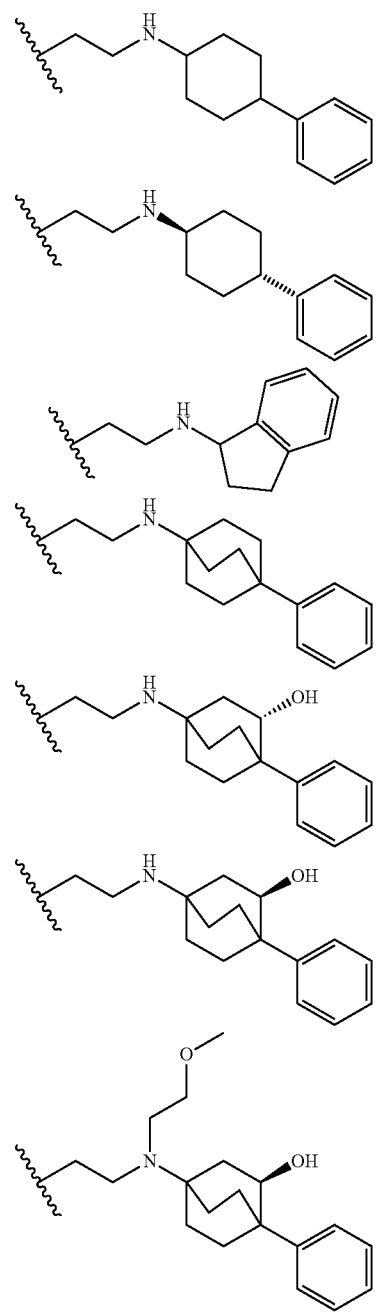

-continued

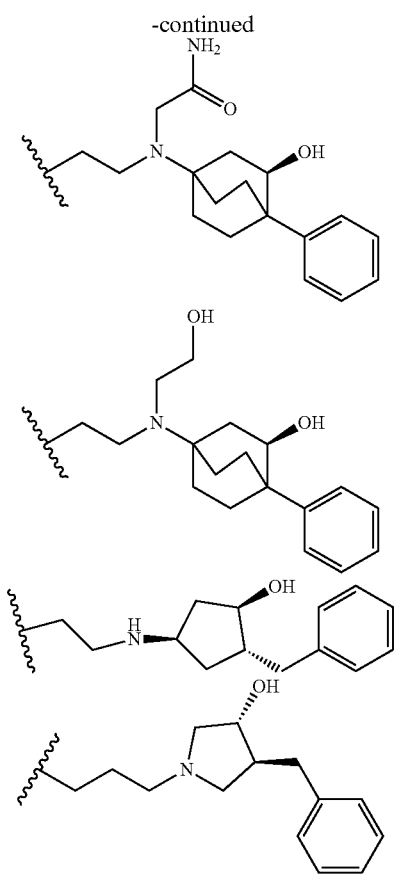

R[1] is H, benzyl, 4-chlorobenzyl, 3-difluoromethoxybenzyl, 3,5-difluorobenzyl, 3-trifluoromethylbenzyl, 3-hydroxybenzyl, 3-hydroxyphenethyl, 3-(4-piperidinyl)benzyl, 1-naphthylmethyl, 3-pyridinylmethyl, 3-2-oxo-1,2-dihydropyridin-4-yl, cyclopropyl, cyclobutyl, cyclobutylmethyl, cyclopentyl, 3,3-difluorocyclopentyl, 2,2-difluorocyclobutyl, 2,2,3-trifluorocyclobutyl, 3,3,3-trifluoropropyl, 3-pyridylmethyl, or 1,2,3,4-tetrahydroisoquinolin-6-yl) methyl;

In a fourth aspect, the present invention provides a compound selected from the exemplified examples or a pharmaceutically acceptable salt, a stereoisomer, a tautomer, or a solvate thereof.

In another aspect, the present invention provides a compound selected from any subset list of compounds within the scope of the fifth aspect.

In another embodiment, the compounds of the present invention have $IC_{50}$ values $\leq 10$ µM, using the MPO peroxidation assay disclosed herein, preferably, $IC_{50}$ values $\leq 3$ µM, more preferably, $IC_{50}$ values $\leq 0.3$ µM, even more preferably, $IC_{50}$ values $\leq 0.1$ µM.

In another embodiment, the compounds of the present invention have $IC_{50}$ values $\leq 10$ µM, using the MPO chlorination assay disclosed herein, preferably, $IC_{50}$ values $\leq 3$ µM, more preferably, $IC_{50}$ values $\leq 0.3$ µM, even more preferably, $IC_{50}$ values $\leq 0.1$ µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a pharmaceutical composition as defined above further comprising additional therapeutic agent(s).

In another embodiment, the present invention provides a process for making a compound of the present invention.

In another embodiment, the present invention provides an intermediate for making a compound of the present invention.

In another embodiment, the present invention provides a compound of the present invention, for use in therapy, alone, or optionally in combination with another compound of the present invention and/or at least one other type of therapeutic agent.

In another embodiment, the present invention provides a compound of the present invention for use in therapy, for the treatment and/or prophylaxis of diseases or disorders associated with the activity of MPO, alone, or optionally in combination with another compound of the present invention and/or at least one other type of therapeutic agent.

In another embodiment, the present invention provides a method for the treatment and/or prophylaxis of diseases or disorders associated with the activity of MPO, comprising administering to a patient in need of such treatment and/or prophylaxis a therapeutically effective amount of at least one of the compounds of the present invention, alone, or optionally in combination with another compound of the present invention and/or at least one other type of therapeutic agent.

In another embodiment, the present invention provides a method for the treatment and/or prophylaxis of diseases or disorders associated with the activity of MPO, comprising administering to a patient in need thereof a therapeutically effective amount of a first and second therapeutic agent, wherein the first therapeutic agent is a compound of the present invention and the second therapeutic agent is one other type of therapeutic agent.

In another embodiment, the present invention also provides the use of a compound of the present invention for the manufacture of a medicament for the treatment and/or prophylaxis of diseases or disorders associated with the activity of MPO, alone, or optionally in combination with another compound of the present invention and/or at least one other type of therapeutic agent.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of diseases or disorders associated with the activity of MPO.

Examples of diseases or disorders associated with the activity of MPO that may be prevented, modulated, or treated according to the present invention include, but are not limited to, atherosclerosis, coronary heart disease, coronary artery disease, coronary vascular disease, cerebrovascular disorders, peripheral vascular disease, dyslipidemias and the sequelae thereof, cardiovascular disorders, angina, ischemia, cardiac ischemia, heart failure, stroke, myocardial infarction, reperfusion injury, angioplastic restenosis, hypertension, vascular complications of diabetes, obesity or endotoxemia.

In one embodiment, examples of diseases or disorders include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, transient ischemic attack and stroke. In one embodiment, examples of diseases or disorders include atherosclerosis, coronary heart disease, cerebrovascular disorders and dyslipidemias and the sequelae thereof. In one embodiment, examples of diseases or disorders include coronary artery disease and acute coronary syndrome. In one embodiment, examples of diseases or disorders include dyslipidemias and the sequelae thereof. In one embodiment, examples of diseases or disorders include heart failure. In one embodiment, examples of diseases or disorders include lung diseases including asthma, COPD and cystic fibrosis. In one embodiment, examples of diseases or disorders include neuroinflammatory diseases, including multiple sclerosis, Alzheimer's disease, Parkinson's disease, multiple system atrophy, and stroke.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, diuretics, mineralocorticoid receptor antagonists, calcium channel blockers, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma high-density lipoprotein (HDL)-raising agents, anti-hypercholesterolemic agents, cholesterol biosynthesis inhibitors (such as HMG CoA reductase inhibitors), acyl-coenzyme A: cholesterol acytransferase (ACAT) inhibitors, cholesterylester transfer protein (CETP) inhibitors, liver X receptor (LXR) agonists, anti-probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, diuretics, mineralocorticoid receptor antagonists, calcium channel blockers, anti-diabetes agents, angiotensin II receptor antagonists, angiotensin converting enzyme inhibitors, platelet aggregation inhibitors, factor Xa inhibitors, anti-thrombotic agents, renin inhibitors, fibrinogen receptor antagonists, aspirin and fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 15th Edition, John Wiley & Sons, Inc., New York (2007). "$C_6$ or $C_{10}$ aryl" or "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Greene, T. W. et al., *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

As a person of ordinary skill in the art would be able to understand, a ketone (—CH—C=O) group in a molecule may tautomerize to its enol form (—C=C—OH). Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of the present invention may have prodrug forms. Any compound that will be converted in vivo to provide the bioactive agent (i.e., a compound of Formula (I) or Formula (II)) is a prodrug within the scope and spirit of the invention. Various forms of prodrugs are well known in the art. For examples of such prodrug derivatives, see:

(a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield Formula (I) or Formula (II) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) or Formula (II) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2nd Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for "aqueous", "sat" or "sat'd" for saturated, "MW" for molecular weight, "mw" or "µwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Ac | acetic |
| AcOH | acetic acid, |
| ACN (or MeCN) | acetonitrile |
| APF | aminophenyl fluorescein |
| Aq. | aqueous |
| BINAP | 2,2'-bis(diphenylphosphino)-1,1'-binaphthyl |
| Bn | benzyl |
| Boc | tert-butyl carbonyl |
| Boc$_2$O | di-tert-butyl dicarbonate |
| Bu | butyl |
| dba (Pd$_2$(dba)$_3$) | dibenzylideneacetone |
| DCM | dichloromethane |
| DEAD | diethyl azodicarboxylate |
| DIAD | diisopropyl azodicarboxylate |
| DIEA | diisopropylethylamine |
| DMAP | 4-dimethylaminopyridine |
| DME | dimethoxy ethane |
| DMF | dimethylformamide |
| DMSO | dimethyl sulfoxide |
| dppf | 1,1'-bis(diphenylphosphino)ferrocene |
| (DtBPF)PdCl$_2$ | 1.1'-bis(di-tert-butylphosphino)ferrocene palladium dichloride |
| EPX | eosinophil peroxidase |
| Et | ethyl |
| EtOH | ethanol |
| EtOAc | ethyl acetate |
| HATU | 2-(7-aza-1H-benzotriazole-1-yl)-1,1,3,3-tetramethyluronium hexafluorophosphate |
| HBTU | 2-(1H-benzotriazole-1-yl)-1,1,3,3-tetramethyluronium hexafluorophosphate |
| i-Bu | isobutyl |
| IBCF | isobutylchloroformate |
| i-Pr | isopropyl |
| LAH | lithium aluminum hydride |
| m-CPBA | meta-chloroperbenzoic acid |
| Me | methyl |
| MeOH | methanol |
| MPO | myeloperoxidase |
| NMM | N-methylmorpholine |

-continued

| | |
|---|---|
| NMP | N-methylpyrrolidone |
| PCC | pyridinium chlorochromate |
| Ph | phenyl |
| Pr | propyl |
| t-Bu | tert-butyl |
| tetrakis | tetrakis(triphenylphosphine) palladium |
| TBDMS-Cl | t-butyldimethylchlorosilane |
| TBDMS | t-butyldimethylsilyl |
| TBDPS | t-butyldiphenylsilyl |
| TEA | triethylamine |
| TFA | trifluoroacetic acid |
| THF | tetrahydrofuran |
| TIPS | triisopropylsilyl |
| TIPS-Cl | tri-isopropylsilyl chloride |
| TMAD | N,N,N',N'-tetramethylazodicarbonamide (1,1'azobis(N,N-dimethylformamide)) |
| Tr | trityl (triphenylmethyl) |
| Ts | tosyl |

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH Publishers, Inc., New York, N.Y. (1999). Preferred methods include, but are not limited to, those described below. All references cited herein are hereby incorporated in their entirety herein by reference.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene, T. W. et al., *Protecting Groups in Organic Synthesis*, 4th Edition, Wiley (2007)).

Compounds having the general Formula (I):

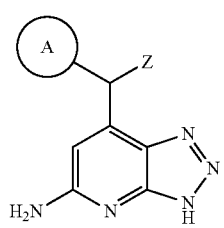

(I)

wherein A and Z are each defined above, can be prepared by the following one or more of the synthetic schemes outlined below.

Triazolopyridine compounds of formula (I) can be prepared by the general route shown in Scheme 1 starting from a suitably protected 7-bromotriazolopyridine such as the bis-trityl intermediate 1-1. Miyaura borylation of 1-1 to yield the corresponding 5,5-dimethyl-1,3,2-dioxaborinane followed by Suzuki-Miyaura condensation with a suitable heteroarylmethylbromide provides intermediates of formula 1-2. Alkylation of compound 1-2 with an appropriately substituted alkyl bromide (ZBr) in the presence of a base such as KOtBu or KHMDS in a suitable solvent such as DMF or THF, provides intermediates 1-3, which after deprotection of the trityl protecting groups leads to compounds of this invention of formula (I).

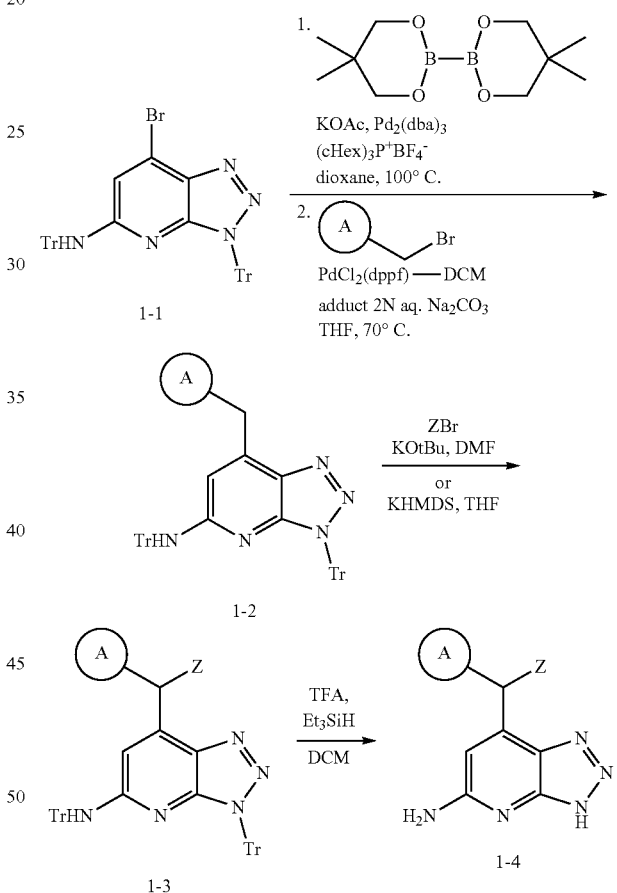

Scheme 1.

Compounds of this invention can also be synthesized by the general route outlined in Scheme 2. Sonogashira condensation between 1-1 and propargyl alcohol provides alkynol 2-1, which is then converted to vinyl iodide 2-2 by treatment with LiAlH$_4$, followed by I$_2$. Iodide 2-2 is then subjected to a Suzuki-Miyaura coupling with an appropriately functionalized heteroaryl boronic acid or boronate in the presence of a base such as Cs$_2$CO$_3$ and a palladium catalyst such as Pd(dppf)Cl$_2$ using a suitable solvent such as THF at elevated temperature to furnish alcohol 2-3. The allylic alcohol is then oxidized with a suitable oxidizing agent, such manganese dioxide, to the corresponding α,β- unsaturated aldehyde 2-4. Reductive amination with the appropriate amine, using either NaBH₄ in EtOH at 60° C. or Na(OAc)₃BH in DCM at rt, provides allylic amines 2-5. Acidic deprotection of the trityl groups followed by reduction of the double bond by hydrogenation over Pt₂O, or by reduction with NiCl₂/NaBH₄, gives compounds of this invention of formula 2-6.

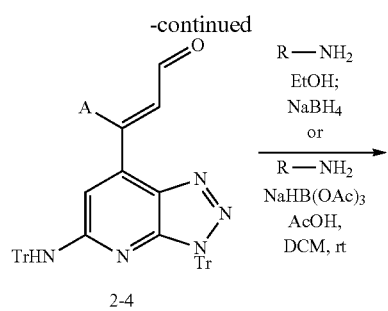

For compounds where Ring A is an N-substituted pyrazole, the steps outlined in Scheme 3 can be used as alternate routes from 1-1 to pyrazole intermediate 3-2 useful for synthesis of additional compounds of this invention. Coupling of 1-1 to Boc-protected pyrazolylmethyl boronate 3-1, followed by in situ hydrolysis of the Boc protecting group provides 3-2. Alternately bromide 1-1 can undergo a Semmelhack carbonylation to provide methyl ester 3-3. This ester can then be converted to bromide 3-4 in two steps by reduction to the corresponding alcohol with LiBH₄ and subsequent treatment with carbon tetrabromide and triphenylphosphine. It is also possible to prepare intermediate 3-2 from bromide 1-1 by first converting the bromide to the boronate 3-5, which can then undergo a Suzuki-Miyaura coupling with 4-bromomethyl-1-Boc-4-pyrazole 3-6 to give 3-2. Intermediate 3-5 can also serve as the starting point for synthesis of additional compounds of this invention of Formula (I) by coupling to other suitably substituted bromomethylheterocycles, followed by trityl deprotection as described above in Scheme 1.

Scheme 3

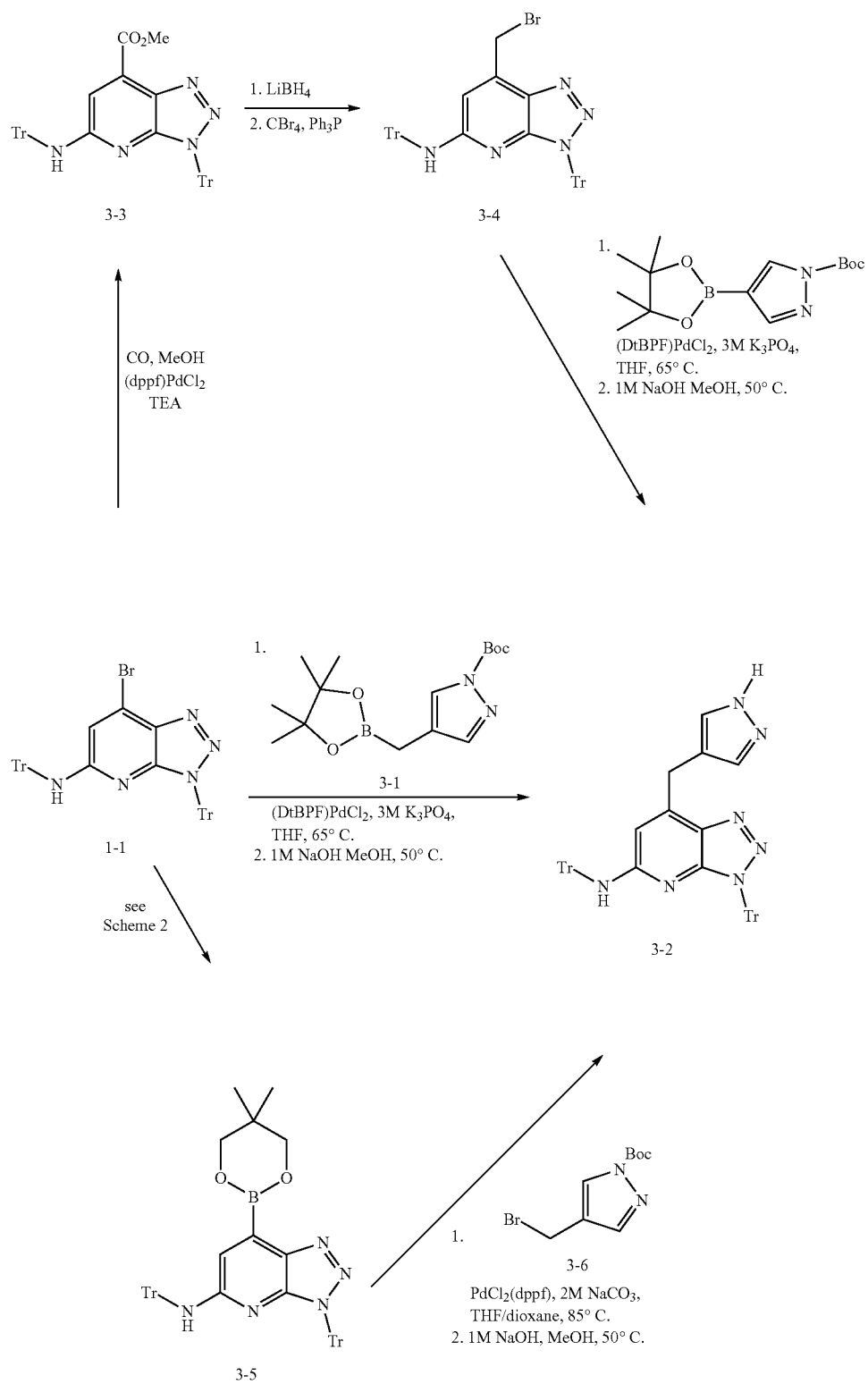

The pyrazole intermediate 3-2 can be converted to compounds of this invention as shown in Scheme 4. Mitsunobu alkylation on the pyrazole N using TMAD, tributylphosphine and an appropriate alcohol in toluene provides 4-1, followed by alkylation at the benzylic position to provide 4-2, and deprotection of the trityl protecting groups as described in Scheme 1 to provide compounds of formula 4-3.

Scheme 4

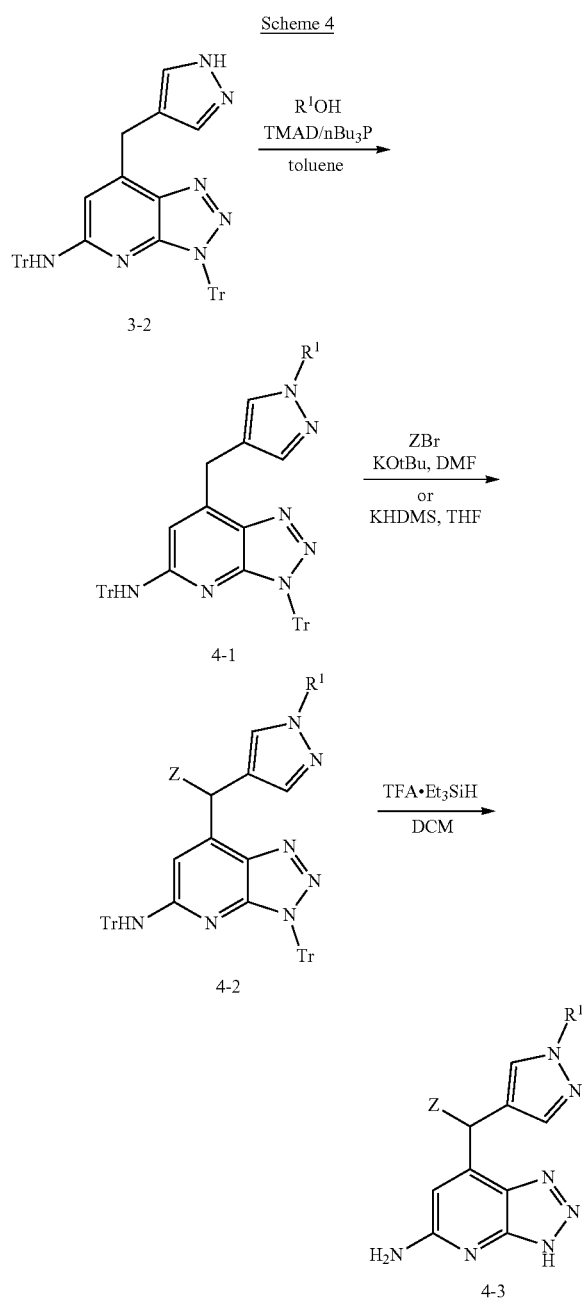

Scheme 5

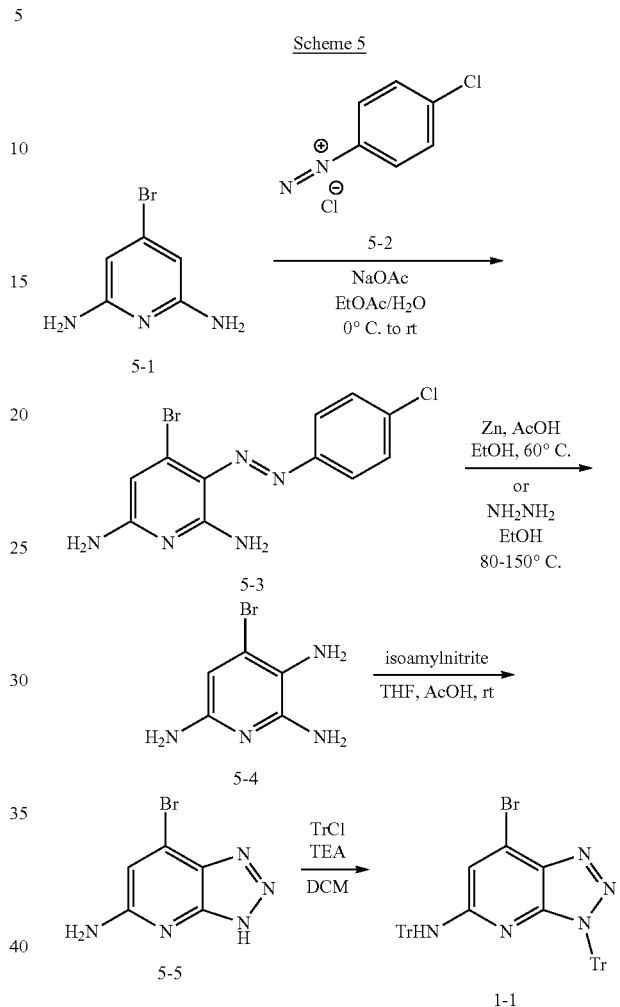

and examples are obtained as mixtures of two trityl regioisomers and are not separated, but used in the various syntheses and procedures described herein as mixtures.

Scheme 5 shows the preparation of triazolopyridine 1-1 from 4-bromo-2,6-diaminopyridine 5-1. Addition of a freshly prepared, cold solution of 4-chlorophenyldiazonium chloride 5-2 in aq. HCl to a solution of 5-1 in water or a biphasic mixture of EtOAc and water at 0° C. to rt provides diazene intermediates 5-3. Intermediate 5-3 is then reduced to the corresponding triamine by treatment with zinc and acetic acid in EtOH at 60° C. or by heating with excess hydrazine in EtOH. The resulting 2,3,6-triamino-4-bromopyridine 5-4 is then treated with isoamylnitrite in THF to furnish 5-amino-7-bromotriazolopyridine 5-5, which is converted to the corresponding bis-trityl derivative 1-1 by treatment with trityl chloride in the presence of TEA in DCM or other suitable solvent. It should be noted that unless otherwise noted the bis-trityl analogs shown in the schemes Alternately, the triazolopyridine ring can be constructed subsequent to the introduction of the ring A and group Z to an appropriately protected 2,6-diaminopyridine intermediate as outlined in Scheme 6. Commercially available 2,6-diamino-pyridine 6-1 or 4-bromo-2,6-diaminopyridine 5-1 are protected as the respective bis-1,5-dimethylpyrrole compounds using a modification of the procedure of Laird et al. (*J. Med. Chem.*, 13:1022 (1970)), by heating the corresponding bis-hydrochloride (X=H) or bis-hydrobromide salt (X=Br) with 2,5-hexanedione in DMF in the presence of MgSO$_4$ at a temperature from 85-120° C. to furnish the protected diaminopyridines 6-2 and 6-3, respectively. Treatment of bromopyridine 6-3 with nBuLi followed by trapping with a heteroarylaldehyde, results in the formation of secondary alcohol 6-4. The des-bromo analog 6-2 may also be used as a starting material for this transformation via direct lithiation carried out at 0° C.; however, this often results in the formation of varying amounts of regioisomeric products. Alternately, bromide 6-3 can be treated with nBuLi at 0° C., followed by quenching with DMF. The resulting aldehyde 6-5 can then be treated with a suitable heteroaryl Grignard reagent to provide the secondary alcohol intermediates 6-4. Conversion of 6-4 to the corresponding acetate 6-6 can be achieved by treatment with acetic anhydride, DMAP and pyridine. Reduction/deoxygenation of 6-6 with samarium iodide in THF in the presence of an alcoholic additive such as tert-butanol or isopropanol, followed by alkylation at the benzylic position results in the formation of intermediate 6-7. Removal of the dimethylpyrrole protecting groups by treatment with hydroxylamine hydrochloride and triethylamine in refluxing aq. iPrOH or EtOH, where water may be added as a cosolvent, results in the formation of the diamine intermediates 6-8, which can be converted to triazolopyridine compounds 6-10 of this invention using the steps outlined in Scheme 5 for conversion of 5-1 to 5-5.

Scheme 6

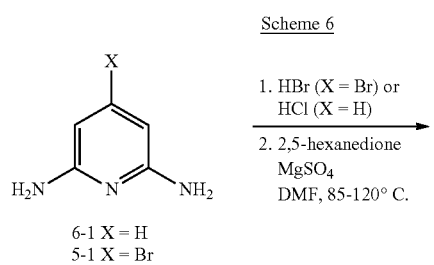

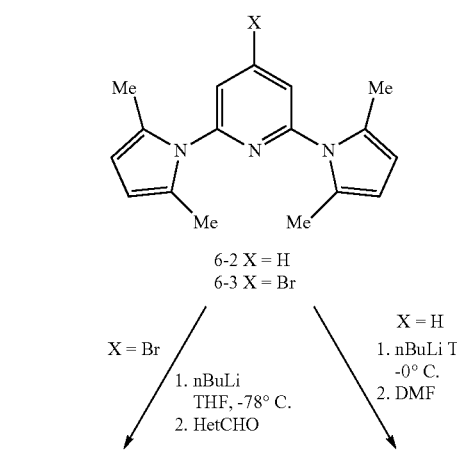

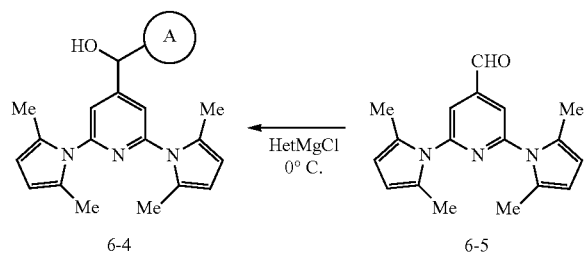

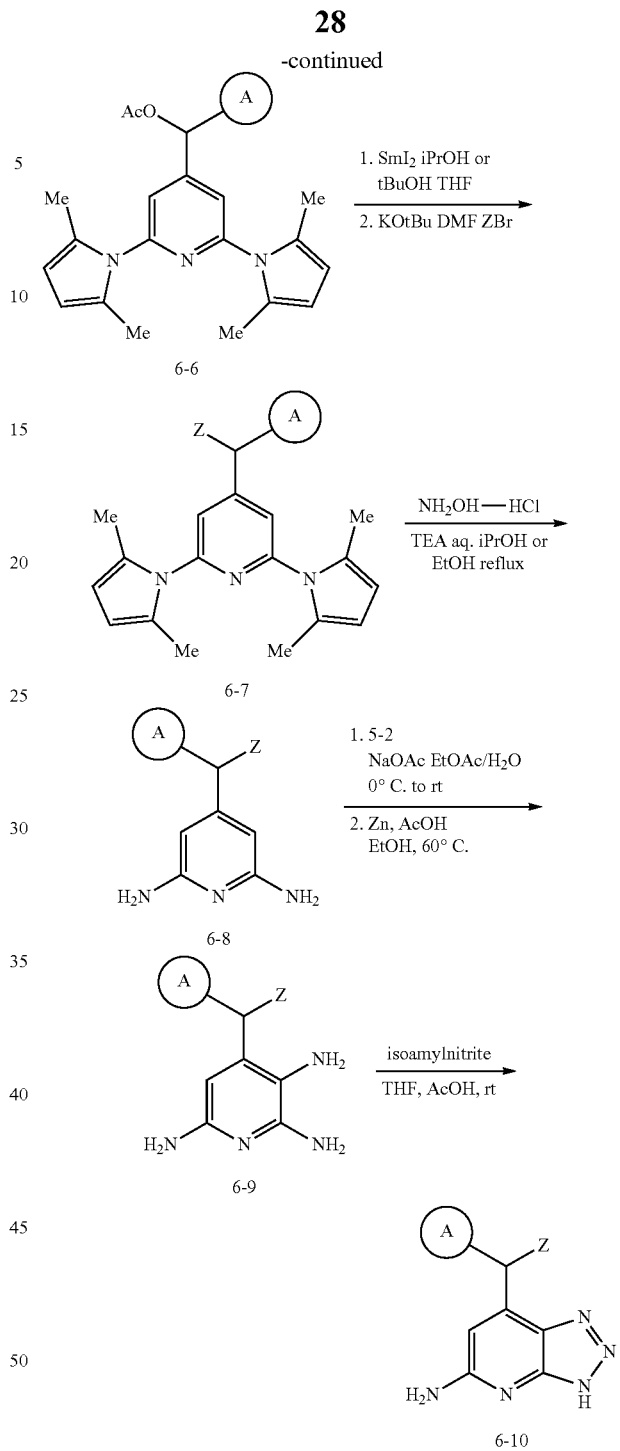

Scheme 7 illustrates the synthesis of pyrazole intermediate 7-4 which can also be used as a starting point for preparation of compounds of this invention. Aldehyde 6-5, prepared as described in Scheme 6, is reduced by treatment with sodium borohydride in EtOH to the corresponding alcohol 7-1. Alternately, this alcohol intermediate can be prepared from bromide 6-3 via a Semmelhack carbonylation, followed by reduction of the resulting methyl ester 7-2 with lithium borohydride. Treatment of the resulting alcohol 7-1 with either methanesulfonic anhydride in the presence of TEA and LiBr or with carbon tetrabromide and triphenylphosphine provides bromide 7-3, which undergoes a Suzuki coupling with commercially available Boc-4-pyrazole pinacolboronate 7-4 in the presence of a suitable catalyst such as (DtBPF)PdCl$_2$. Base hydrolysis removes the Boc-protecting group to provide pyrazole intermediate 7-5 that can then be further elaborated to compounds of this invention as outlined in Scheme 8 below. It should also be recognized by one skilled in the art that additional intermediates useful for the preparation of compounds of the invention wherein A is a heterocycle other than pyrazole can also be obtained from bromide 6-3 through the application of the above described Suzuki coupling conditions or a modification thereof with the appropriate heterocyclic boronic acids or boronates.

TMAD and tributylphosphine in toluene or mixtures of toluene with THF or DMF, or by base-catalyzed alkylation in the presence of an alkyl halide under carefully controlled conditions to avoid bis-alkylation at the benzylic position to yield substituted pyrazole intermediates 8-1. Alternately, aryl or heteroaryl groups can be introduced on the pyrazole via Ullmann type copper mediated arylations with aryl or heteroaryl bromides or iodides to provide the analogous 1-arylpyrazole intermediates. A second alkylation on the benzylic carbon is then carried out to provide compounds 8-2. Treatment with hydroyxlamine to remove the pyrrole protecting groups, followed by conversion of the resulting 2,6-diaminopyridines to triazolopyridine compounds via the Scheme 7

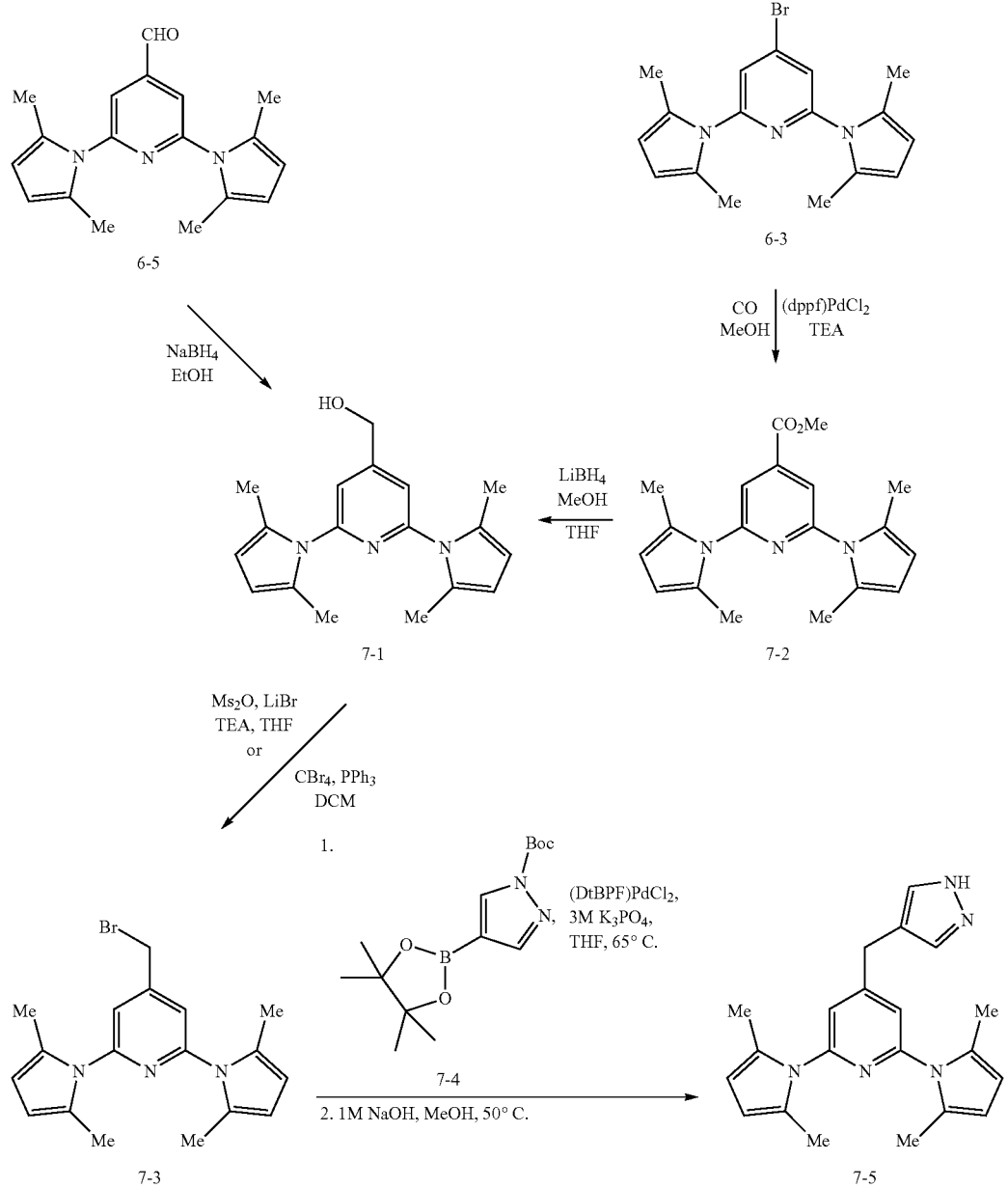

As shown in Scheme 8, pyrazole intermediate 7-5 can be alkylated preferably using Mitsunobu conditions with steps outlined for the conversion of 6-8 to 6-10 in Scheme 6 provides compounds 8-3 of this invention.

Scheme 8

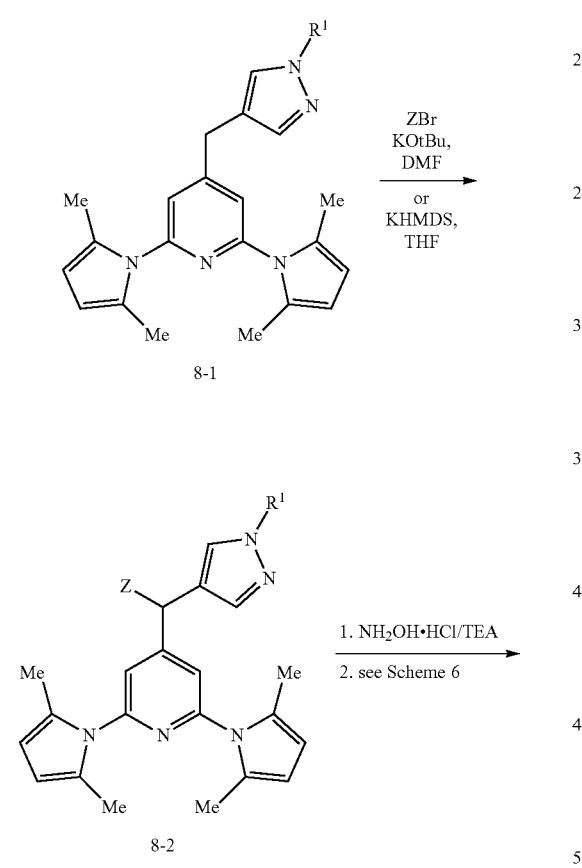

An alternate synthesis of pyrazole compounds of formula 8-3 is outlined in Scheme 9. Protection of the pyrazole NH in intermediate 7-5 as its 2-tosylethyl analog 9-1 can be achieved by treatment of 7-5 with 2-tosylethanol under the previously described Mitsunobu conditions (TMAD/tri-n-butylphosphine in toluene). Deprotection of the bis-dimethylpyrrole protecting groups gives the corresponding diamine, which is converted by the steps outlined in Scheme 6 to triazolopyridine intermediate 9-2. Treatment of 9-2 with excess trityl chloride in the presence of triethylamine provides the bis-trityl protected intermediate 9-3. Benzylic alkylation to introduce the group Z as described above provides 9-4. The 2-tosylethyl protecting group is then removed from the pyrazole by treatment with KOtBu in THF in the presence of excess hydrazine added to trap the resulting vinylsulfone by-product. The resulting pyrazole intermediate 3-2 can then be converted to final compounds 4c by alkylation of the pyrazole followed by removal of the trityl protecting groups (see Scheme 4).

Scheme 9

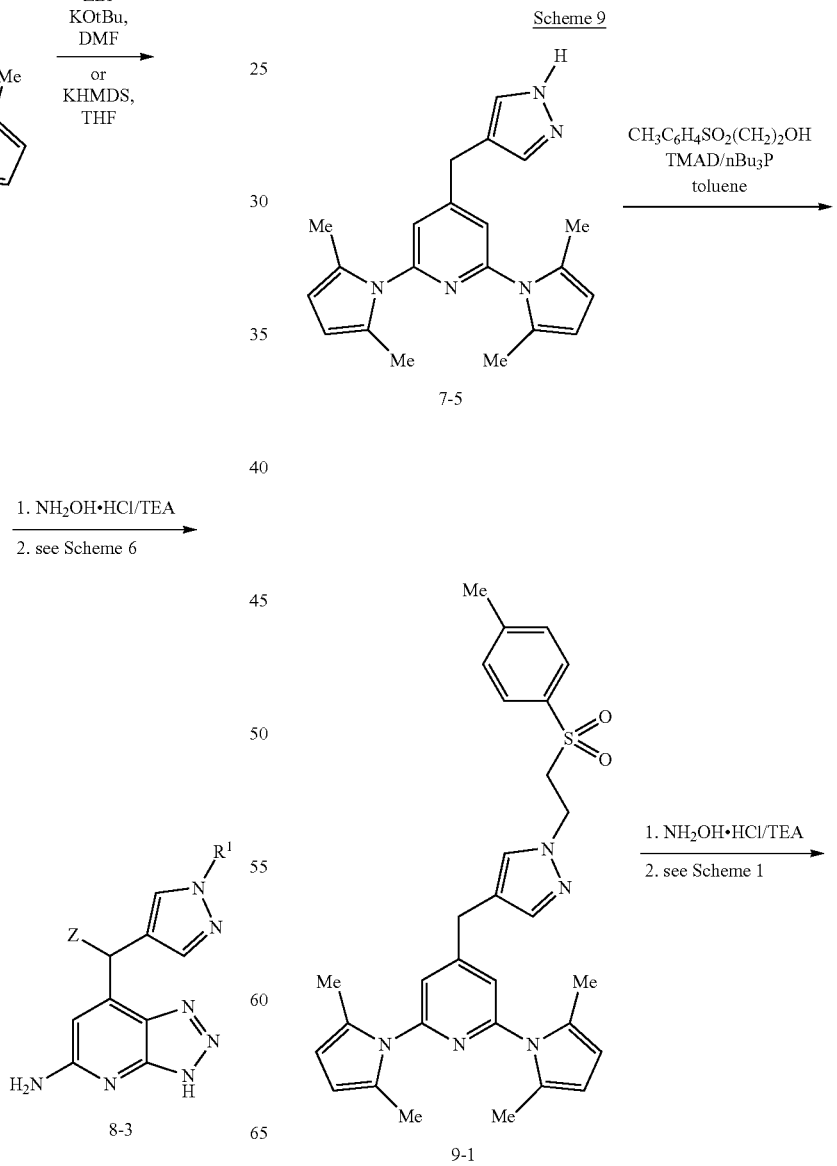

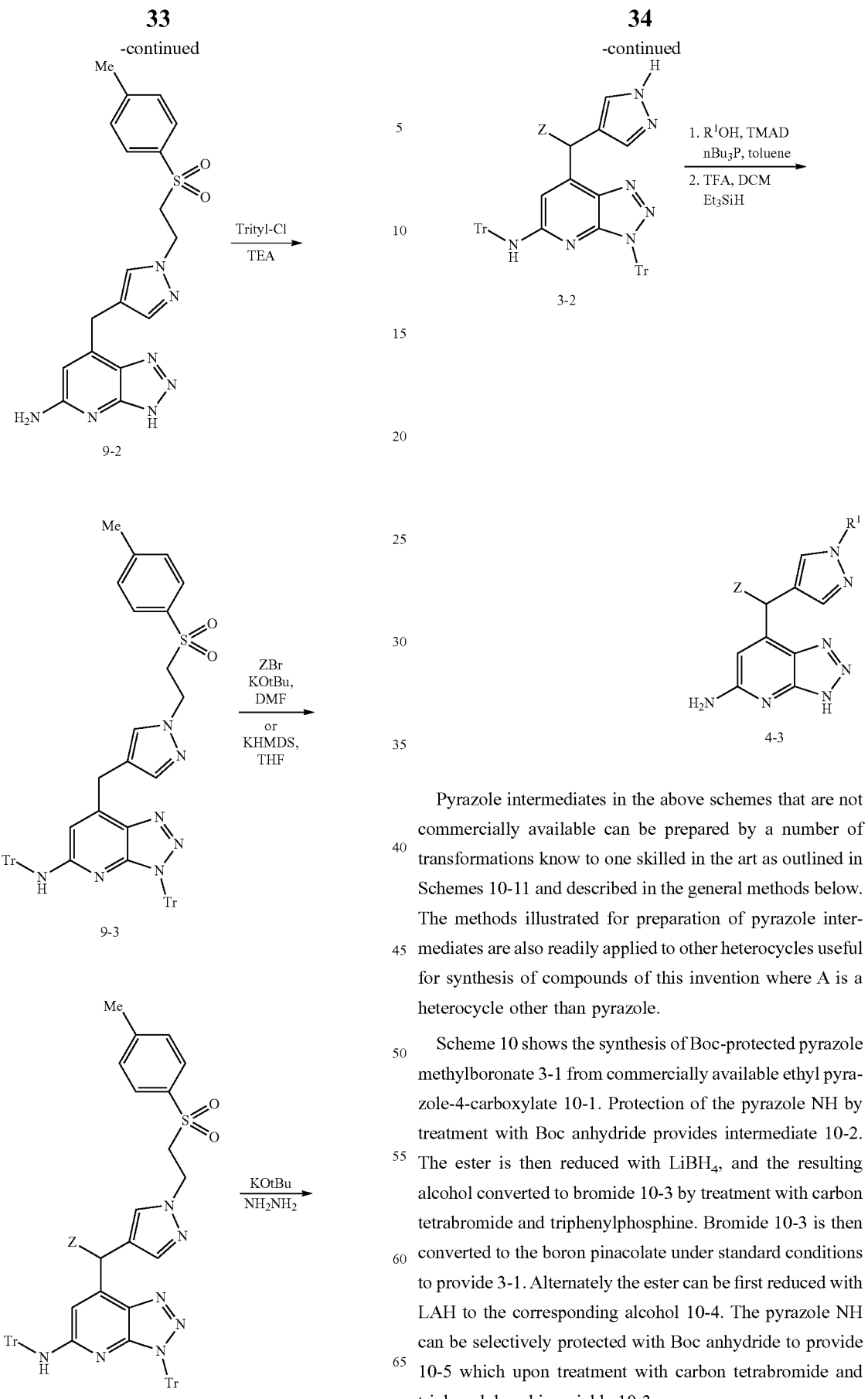

Pyrazole intermediates in the above schemes that are not commercially available can be prepared by a number of transformations know to one skilled in the art as outlined in Schemes 10-11 and described in the general methods below. The methods illustrated for preparation of pyrazole intermediates are also readily applied to other heterocycles useful for synthesis of compounds of this invention where A is a heterocycle other than pyrazole.

Scheme 10 shows the synthesis of Boc-protected pyrazole methylboronate 3-1 from commercially available ethyl pyrazole-4-carboxylate 10-1. Protection of the pyrazole NH by treatment with Boc anhydride provides intermediate 10-2. The ester is then reduced with LiBH$_4$, and the resulting alcohol converted to bromide 10-3 by treatment with carbon tetrabromide and triphenylphosphine. Bromide 10-3 is then converted to the boron pinacolate under standard conditions to provide 3-1. Alternately the ester can be first reduced with LAH to the corresponding alcohol 10-4. The pyrazole NH can be selectively protected with Boc anhydride to provide 10-5 which upon treatment with carbon tetrabromide and triphenylphosphine yields 10-3.

Scheme 10

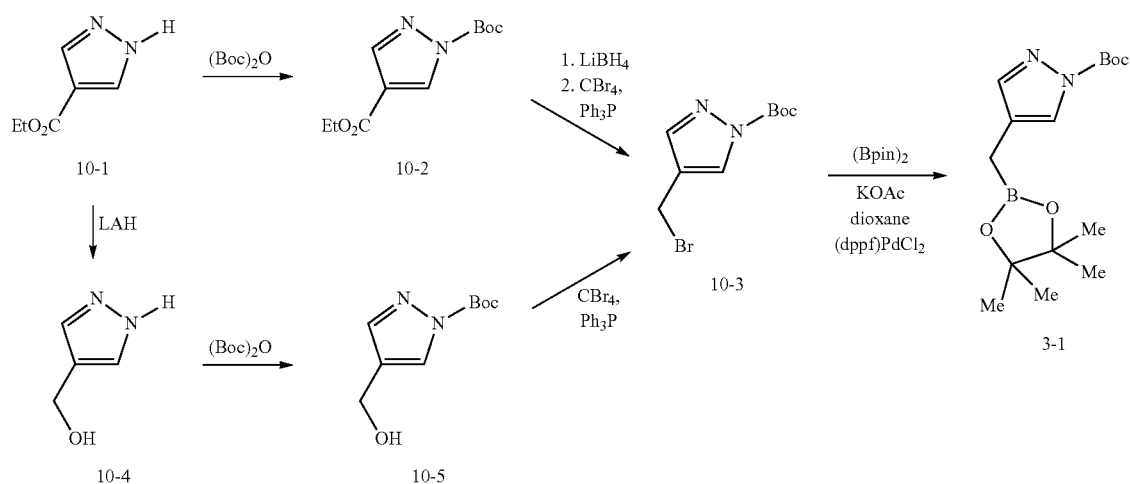

N-alkylylated pyrazole-4-boronates suitable for preparing compounds of this invention according to Scheme 2 above can be prepared as shown in Scheme 11, wherein commercially available pyrazole-4-boronate 11-1 is alkylated either with a suitable alkyl bromide or chloride in the presence of a base such as sodium hydride, or alternately, via the previously described Mitsunobu conditions using an appropriate alcohol. The resulting pyrazole boronate 11-2 is then coupled via a Suzuki-Miyaura condensation with intermediate 2-2 to give 11-3. Following the steps outlined in Scheme 2, intermediate 11-3 is converted in 4 steps into compounds of this invention of formula 11-6.

-continued

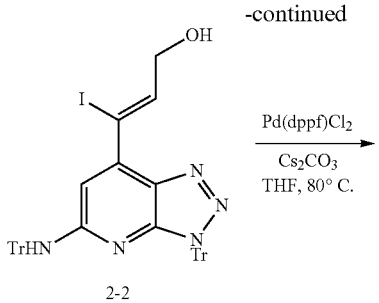

Scheme 11

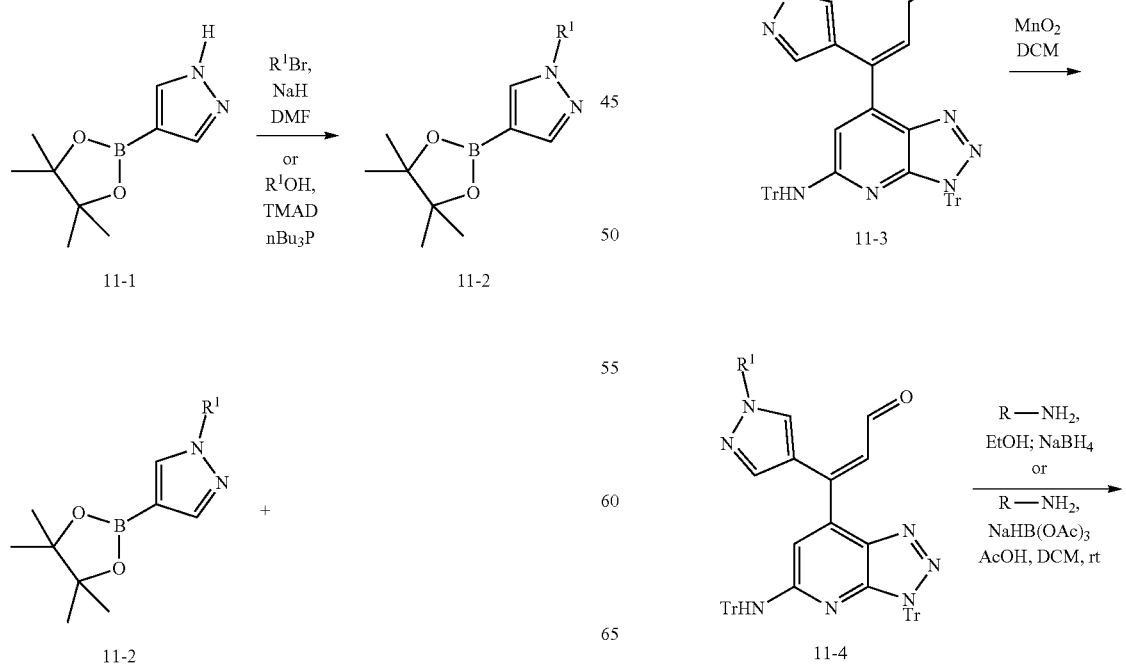

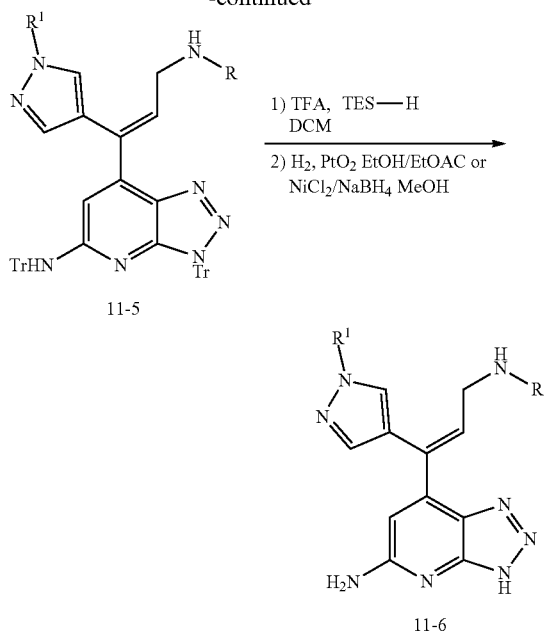

11-5

11-6

General Methods

The following methods were used in the exemplified Examples, except where noted otherwise.

Purification of intermediates and final products was carried out via either normal or reverse phase chromatography. Normal phase chromatography was carried out using pre-packed $SiO_2$ cartridges eluting with either gradients of hexanes and ethyl acetate or DCM and MeOH unless otherwise indicated. For highly polar amines, gradients of DCM and 1M $NH_3$ in MeOH were used. Reverse phase preparative HPLC was carried out using C18 columns with UV 220 nm or prep LCMS detection eluting with gradients of Solvent A (90% water, 10% MeOH, 0.1% TFA) and Solvent B (10% water, 90% MeOH, 0.1% TFA) or with gradients of Solvent A (90% water, 10% ACN, 0.1% TFA) and Solvent B (10% water, 90% ACN, 0.1% TFA) or with gradients of Solvent A (95% water, 2% ACN, 0.1% HCOOH) and Solvent B (98% ACN, 2% water, 0.1% HCOOH) or with gradients of Solvent A (95% water, 5% ACN, 10 mM $NH_4OAc$) and Solvent B (98% ACN, 5% water, 10 mM $NH_4OAc$) or with gradients of Solvent A (95% water, 2% ACN, 0.1% $NH_4OH$) and Solvent B (98% ACN, 2% water, 0.1% $NH_4OH$).

Analytical HPLC: Methods Employed in Characterization of Examples

Products were analyzed by reverse phase analytical HPLC: carried out on a Shimadzu Analytical HPLC: system running Discovery VP software. RT=retention time.

Method A: Linear gradient of 0 to 100% B over 10 min, with 5 min hold at 100% B
UV visualization at 254 nm
Column: SunFire C18; 3.5 μm; 4.6×150 mm
Flow rate: 1 mL/min (Method A)
Solvent A: 10% acetonitrile, 90% water, 0.05% TFA
Solvent B: 10% water, 90% acetonitrile, 0.05% TFA Method B: Linear gradient of 0 to 100% B over 10 min, with 5 min hold at 100% B
UV visualization at 254 nm
Column: XBridge Phenyl 3.5 μm; 4.6×150 mm
Flow rate: 1 mL/min (Method A)
Solvent A: 10% acetonitrile, 90% water, 0.05% TFA
Solvent B: 10% water, 90% acetonitrile, 0.05% TFA Method C: Linear gradient: 0-100% B over 3 min, then a 0.75-min hold at 100% B
Temperature: 50° C.
UV visualization at 220 nm
Column: Waters Acquity UPLC BEH C18, 1.7 m; 2.1×50 mm
Flow: 1.11 mL/min (Method A)
Solvent A: 5:95 acetonitrile:water with 0.1% TFA
Solvent B: 95:5 acetonitrile:water with 0.1% TFA Method D: Linear gradient: 0-100% B over 3 min, then a 0.75-min hold at 100% B
Temperature: 50° C.
UV visualization at 220 nm
Column: Waters Acquity UPLC BEH C18, 1.7 μm; 2.1×50 mm
Flow: 1.11 mL/min (Method A)
Solvent A: 5:95 acetonitrile:water with 10 mM ammonium acetate
Solvent B: 95:5 acetonitrile:water with 10 mM ammonium acetate LC/MS Methods Employed in Characterization of Examples Reverse phase analytical HPLC/MS was performed on Shimadzu LC10AS systems coupled with Waters ZMD Mass Spectrometers (Methods A-E) or Waters Acquity system coupled with a Waters MICROMASS® ZQ Mass Spectrometer (Method F).

Method A: Linear gradient of 0 to 100% B over 4 min, with 1 min hold at 100% B
UV visualization at 220 nm
Column: PHENOMENEX® Luna C18 4.6×50 mm
Flow rate: 4 mL/min (Method A)
Solvent A: 0.1% trifluoroacetic acid, 90% water, 10% acetonitrile
Solvent B: 0.1% trifluoroacetic acid, 90% acetonitrile, 10% water Method B: Linear gradient of 0 to 100% B over 4 min, with 1 min hold at 100% B
UV visualization at 220 nm
Column: PHENOMENEX® Luna C18 2×50 mm
Flow rate: 4 mL/min (Method A)
Solvent A: 98% water, 2% methanol, 0.1% formic acid
Solvent B: Methanol, 0.1% formic acid Method C: Linear gradient of 0 to 100% B over 4 min, with 1 min hold at 100% B
UV visualization at 220 nm
Column: PHENOMENEX® Luna C18 4.6×50 mm
Flow rate: 4 mL/min (Method A)
Solvent A: 0.1% trifluoroacetic acid, 90% water, 10% methanol
Solvent B: 0.1% trifluoroacetic acid, 90% methanol, 10% water Method D: Linear gradient of 0 to 100% B over 2 min, with 1 min hold at 100% B
UV visualization at 220 nm
Column: PHENOMENEX® Luna C18 2.0×30 mm
Flow rate: 1 mL/min (Method A)
Solvent A: 0.1% trifluoroacetic acid, 90% water, 10% methanol
Solvent B: 0.1% trifluoroacetic acid, 90% methanol, 10% water Method E: Linear gradient of 0 to 100% B over 2 min, with 1 min hold at 100% B
UV visualization at 220 nm
Column: PHENOMENEX® Luna C18 2.0×30 mm
Flow rate: 1 mL/min (Method A)

Solvent A: 98% water, 2% methanol, 0.1% formic acid
Solvent B: Methanol, 0.1% formic acid.
Method F: Linear gradient of 2 to 98% B over 1 min, with 0.5 min hold time at 98% B
  UV visualization at 220 nm
  Column: Waters BEH C18 2.1×50 mm
  Flow rate: 0.8 mL/min (Method A)
  Solvent A: 0.05% TFA, 100% water
  Solvent B: 0.05% TFA, 100% acetonitrile
Preparative HPLC: Methods Employed in the Purification of Products
Method G: Linear gradient of 20 to 100% B over 10 min, with 2 min hold time at 100% B
  Shimadzu LC-8A binary pumps
  Shimadzu SPD-10 A or 20A UV detector
  UV visualization at 220 nm
  Column: Waters SunFire 19×100 mm 5 µm C18
  Flow rate: 20 mL/min (Method A).
  Solvent A: 0.1% TFA, 10% MeOH, 90% water
  Solvent B: 0.1% TFA, 90% MeOH, 10% water
Method J: Linear gradient of 20 to 100% B over 10 min, with 2 min hold time at 100% B
  Shimadzu LC-8A binary pumps
  Shimadzu SPD-10A or 20A UV detector
  UV visualization at 220 nm
  Column: PHENOMENEX® Luna Axia 30×100 mm 5 µm C18
  Flow rate: 20 mL/min (Method A).
  Peak collection triggered by UV absorbance
  Solvent A: 0.1% TFA, 10% MeOH, 90% water
  Solvent B: 0.1% TFA, 90% MeOH, 10% water
Method K: Linear gradient of 0 to 100% B over 10 min, with 2 min hold time at 100% B
  Shimadzu LC-8A binary pumps
  Shimadzu SPD-20A UV detector
  UV visualization at 220 nm
  Column: PHENOMENEX® Luna Axia 30×75 mm 5 µm C18
  Flow rate: 20 mL/min (Method A).
  Peak collection triggered by UV absorbance
  Solvent A: 0.1% TFA, 10% ACN, 90% water
  Solvent B: 0.1% TFA, 90% ACN, 10% water
NMR Employed in Characterization of Examples
$^1$H NMR spectra were obtained with Bruker or JEOL® Fourier transform spectrometers operating at frequencies as follows: $^1$H NMR: 400 MHz (Bruker or JEOL®) or 500 MHz (Bruker or JEOL®). $^{13}$C NMR: 100 MHz (Bruker or JEOL®). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled. For $^1$H NMR spectrum taken in 1:1 mixtures of $CDCl_3$ and MeOH, the spectra were referenced to the $CD_3OD$ solvent peak.

IV. Biology

Myeloperoxidase (MPO) and eosinophil peroxidase (EPX) are heme-containing enzymes and are members of the family of mammalian heme peroxidases that also includes salivary peroxidase, lactoperoxidase (LPO), thyroid peroxidase (TPO), prostaglandin H synthase and others. Both MPO and EPX use hydrogen peroxide to oxidize an array of substrates to either hypohalous acids or free radicals. Whereas both EPX and MPO are able to oxidize bromine ($Br^-$), iodine ($I^-$) and thiocyanate ($^-SCN$), MPO is also able to oxidize chloride ($Cl^-$) to hypochlorous acid (HOCl) efficiently.

MPO is present predominantly in neutrophils and to a lesser extent in monocytes and subtypes of tissue macrophages. The processed mature form of the enzyme is a glycosylated 146 kDa homodimer. Each subunit is made of a light and heavy polypeptide chain and contains a protoporphyrin IX group with a central iron. The three-fold linkage of the heme is unique compared to other heme proteins and provides specific spectral and catalytic properties to MPO. MPO uses hydrogen peroxide to oxidize an array of substrates to either hypohalous acids or free radicals. The main substrate for MPO is generally accepted to be chloride, which is oxidized to hypochlorous acid. This is one of the most reactive oxidants produced in vivo. Other substrates include thiocyanate, bromide, tyrosine, tryptophan, sulfhydryls, phenol and indole derivatives, ascorbate, nitrite, nitric oxide, and urate.

The physiological role of MPO is to participate in the killing of invading bacterial and fungal pathogens (Klebanoff, S. J., *J. Exp Med.*, 126:1063-1078 (1967); Klebanoff, S. J., *J. Bacteriol.*, 95:2131-2138 (1968); Klebanoff, S. J., *Science*, 169:1095-1097 (1970)). However, excessive generation of oxidants by MPO and other peroxidases has been linked to tissue damage in many diseases, especially those characterized by acute or chronic inflammation. At sites of inflammation, PMNs or tissue macrophages can generate hydrogen peroxide and upon activation also produce myeloperoxidase. This is evidenced by the fact that, in many cases, enzymatically active MPO in conjunction with 3-chlorotyrosine, a tissue marker for HOCl-mediated damage, or HOCl-modified proteins can be detected in diseased tissues colocalized with neutrophils or macrophages (Daugherty, A. et al., *JCI*, 94:437-444 (1994); Bergt et al., *Proc. Natl. Acad. Sci.*, 101:13032-13037 (2004); Pennathur, S. et al., *JBC*, 279:42977-42983 (2004); Choi D. K. et al., *J. Neurosci.*, 25(28):6394-6600 (2005)).

Eosinophil peroxidase (EPX) is a cationic heme-containing protein, and represents nearly 25% of the total mass of the secondary granule protein in eosinophils. It is a highly basic 77 kDa protein made up of two subunits containing a modified Fe-protoporphyrin-IX prosthetic group. EPX shares with MPO the ability to use $H_2O_2$ to oxidize thiocyanate, bromide, and nitrite in vivo to kill bacteria, and viruses (Jong, E. C. et al., *J. Immunol.*, 124:1949-1953 (1980)). Eosinophils play a unique role in host defense mechanisms but increased levels of circulating and tissue eosinophils are implicated in promoting cellular and tissue injury in particular in asthma, and during allergic inflammatory responses of lung diseases.

MPO Peroxidation Assay (Amplex Red Assay)

MPO peroxidation activity was measured in 100 mM KPi (pH 7.4) by utilizing the non-fluorescent reagent Amplex Red (Invitrogen Cat. #A12222) which can be oxidized to the highly fluorescent resorufin. Amplex Red is oxidized by the peroxidase action of MPO to resorufin. Reactions were carried out in 50 µL total volume by adding a 25 µL mixture of 200 pM myeloperoxidase and 40 nM $H_2O_2$ (Sigma #349887) to 100 nL inhibitor in 100% DMSO in a 384 well Perkin Elmer Optiplate. Enzyme and compound were preincubated for ten minutes at rt.

After the ten minute preincubation, 25 µL of an Amplex Red mixture containing 200 µM Amplex Red and 10 mM H$_2$O$_2$ was added to the plate. Kinetic determinations were carried out immediately on a Perkin Elmer Envision (15 minute kinetic read, Ex: 535 nm, Em: 590 nm).

IC$_{50}$ values were calculated by determining the slope of the linear portion of the kinetic trace (180-540 secs), and using that calculated slope to determine % inhibition occurring at each concentration of inhibitor using the following equation:

$$Y = A + \frac{B - A}{1 + (C/x)^D}$$

where A=minimal Y value (activity level of inhibited sample), B=maximal Y value (activity level of uninhibited sample), C=Log IC$_{50}$, D=Hill Slope, x=concentration of inhibitor.

MPO Chlorination Assay (APF Assay)

MPO chlorination activity was measured in 100 mM KPi (pH 7.4) by utilizing the non-fluorescent reagent Aminophenyl fluorescein (APF, Invitrogen Cat. #A36003). APF is cleaved by (—OCl) to yield the fluorescent compound fluorescein. Reactions were carried out in 50 µL total volume by adding a 25 µL mixture of 200 pM myeloperoxidase and 120 mM NaCl to 100 nL inhibitor in 100% DMSO in a 384 well, non-binding surface clear bottom plate (Corning #3655). Enzyme, inhibitor, and chloride were preincubated for ten minutes at rt.

After the ten minute preincubation, 25 µL of an APF mixture containing 10 mM APF, 120 mM NaCl and 10 µM H$_2$O$_2$ was added to the plate using the internal dispensing system of a Hammatsu FDSS 6000. Kinetic determinations were carried out immediately on the FDSS 6000 (3 minute kinetic read, 1 read every second, ex: 485 nm, em: 535 nm). IC$_{50}$ values for inhibitors were calculated by taking the slope of the linear portion of the kinetic measurement (20 seconds to ~80-120 secs).

IC$_{50}$ values were calculated by determining the slope of the linear portion of the kinetic trace (180-540 secs), and using that calculated slope to determine % inhibition occurring at each concentration of inhibitor using the following equation:

$$Y = A + \frac{B - A}{1 + (C/x)^D}$$

where A=minimal Y value (activity level of inhibited sample), B=maximal Y value (activity level of uninhibited sample), C=Log IC$_{50}$, D=Hill Slope, x=concentration of inhibitor.

The exemplified Examples disclosed below were tested in the MPO peroxidation assay described above and found to have MPO inhibitory activity. A range of IC$_{50}$ values of ≤10 µM (10000 nM) was observed.

Most of the exemplified Examples disclosed below were tested in the MPO chlorination assay described above and found to have MPO inhibitory activity. A range of IC$_{50}$ values of ≤10 µM (10000 nM) was observed. Table 1 below lists IC$_{50}$ value range in the MPO peroxidation (Amplex Red) assay and MPO chlorination assay (APF) measured for the following Examples. Potency ranges A=1-100 nM; B=101-999 nM; C=1000-10000 nM.

TABLE 1

| Example No. | Amplex Red Assay IC$_{50}$ value (µM) | APF Assay IC$_{50}$ value (µM) |
|---|---|---|
| 1 | C | A |
| 2 | B | B |
| 3 | B | B |
| 4 | C | B |
| 5 | C | A |
| 6 | B | A |
| 7 | B | A |
| 8 | C | B |
| 9 | C | A |
| 10 | B | C |
| 11 | B | B |
| 12 | B | — |
| 13 | B | A |
| 14 | B | A |
| 15 | B | C |
| 16 | B | A |
| 17 | B | A |
| 18 | A | A |
| 19 | B | A |
| 20 | B | A |
| 21 | B | B |
| 22 | C | B |
| 23 | C | A |
| 24 | B | A |
| 25 | B | A |
| 26 | B | A |
| 27 | B | A |
| 28 | B | A |
| 29 | B | A |
| 30 | B | A |
| 31 | B | A |
| 32 | C | B |
| 33A | C | B |
| 33B | A | A |
| 34 | B | A |
| 35 | B | A |
| 36 | C | B |
| 37 | A | A |
| 38 | A | A |
| 39 | B | A |
| 40 | B | B |
| 41 | A | A |
| 42 | A | A |
| 43 | C | A |
| 44 | C | B |
| 45 | B | B |
| 46 | B | B |
| 47 | B | B |
| 48 | C | B |
| 49 | C | B |
| 50 | B | A |
| 51 | A | A |
| 52 | A | A |
| 53 | C | B |
| 54 | C | B |
| 55 | B | B |

Accordingly, the compounds of the present invention may be administered to mammals, preferably humans, for the treatment of a variety of conditions and disorders, including, but not limited to, atherosclerosis, coronary artery disease, acute coronary syndrome, dyslipidemias and the sequelae thereof, angina, ischemia, cardiac ischemia, myocardial infarction, reperfusion injury, angioplastic restenosis, hypertension, vascular complications of diabetes, obesity or endotoxemia, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrastemal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors, antihypertensives or other pharmaceutically active material.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin and fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians'Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the myeloperoxidase. Such compounds may be provided in a commercial kit, for example, for use in pharmaceutical research involving myeloperoxidase activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving myeloperoxidase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

VI. Examples

The following Examples have been prepared, isolated and characterized using the methods disclosed herein. The following examples demonstrate a partial scope of the invention and are not meant to be limiting of the scope of the invention Intermediate 1 (Scheme 5). 7-Bromo ditrityl-3H-[1,2,3]triazolo[4,5-b]pyridin-5-amine

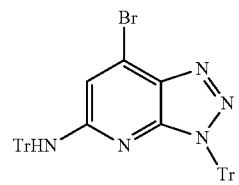

Step A. (E)-4-Bromo-3-((4-chlorophenyl)diazenyl)pyridine-2,6-diamine

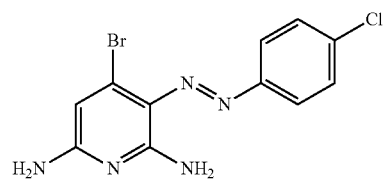 [SMILES: Nc1cc(Br)c(/N=N/c2ccc(Cl)cc2)c(N)n1]

To a solution of 4-chloroaniline (0.678 g, 5.32 mmol) in 6 N HCl (3.37 mL, 20.2 mmol) at 0° C. was added a solution of sodium nitrite (0.367 g, 5.32 mmol) in water (0.581 mL), and the reaction mixture was stirred for 30 min. The reaction mixture was then treated with urea (0.032 g, 0.53 mmol). The solution was then poured into a solution of 4-bromopyridine-2,6-diamine (1.00 g, 5.32 mmol) in water (14.5 mL). After 30 min, sodium acetate (1.96 g, 23.9 mmol) was added, and the reaction mixture was allowed to stir overnight. The reaction mixture was then filtered, and the filtrate was dried in vacuo to furnish the diazene intermediate (1.19 g, 68.7%). MS(ESI) m/z 328.0 (M+H).

Step B. 4-Bromopyridine-2,3,6-triamine

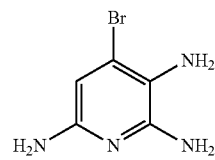

To a solution of the product of Step A (1.19 g, 3.65 mmol) in EtOH (12 mL) was added acetic acid (0.627 mL, 11.0 mmol) and zinc powder (0.717 g, 11.0 mmol), and the reaction mixture was heated to 70° C. After 90 min, the reaction mixture was filtered through Celite® and concentrated. The residue was purified by silica gel chromatography to furnish the triamine intermediate (0.57 g, 77%).

Step C. 7-Bromo-3H-[1,2,3]triazolo[4,5-b]pyridin-5-amine

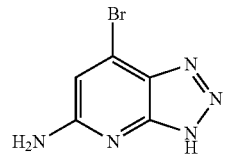

To a solution of the triamine from Step B (0.568 g, 2.80 mmol) in THF (28.0 mL) was added isoamyl nitrite (0.377 mL, 2.80 mmol). The reaction mixture was allowed to stir overnight. The solution was then treated with an additional 0.20 mL of isoamyl nitrite, and the solution allowed to stir overnight. The solution was then concentrated, and the residue purified by silica gel chromatography to furnish the desired triazolopyridine (0.185 g, 30.9%). MS(ESI) m/z 214 (M+H).

Intermediate 1. TEA (81.0 mL, 581 mmol) was added to a suspension of diaminotriazolopyridine from Step C (25.0 g, 117 mmol) and trityl chloride (75.0 g, 269 mmol) in DCM (1500 mL), and the reaction mixture was stirred at rt overnight. The reaction mixture was concentrated and purified by column chromatography to yield the title compound as a mixture of 2 trityl regioisomers (~15 g, 18%) as a tan solid. MS(ESI) m/z 700.1

Intermediate 2 (Compound 2-2 in Scheme 2). (Z)-3-iodo-3-(3-trityl-5-(tritylamino)-3H-[1,2,3]triazolo[4,5-b]pyridin-7-yl)prop-2-en-1-ol

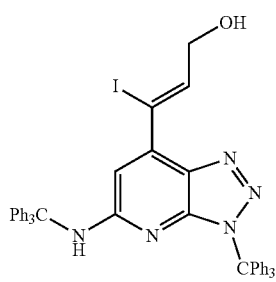

Step A. 3-(3-trityl-5-(tritylamino)-3H-[1,2,3]triazolo[4,5-b]pyridin-7-yl)prop-2-yn-1-ol

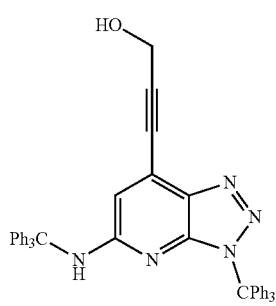

A mixture of Intermediate 1 (10.0 g, 14.3 mmol), bis(triphenylphosphine)palladium(II) chloride (0.402 g, 0.573 mmol), prop-2-yn-1-ol (1.60 g, 28.6 mmol), CuI (0.109 g, 0.573 mmol), DMF (47.7 mL) and TEA (5.98 mL, 42.9 mmol) in a pressure rated vial was degassed by evacuating and back-filling with argon three times. The vial was capped, and the reaction mixture was stirred at 85° C. for 24 hours. The reaction mixture was filtered and concentrated. The residue was purified by flash chromatography on silica gel to yield, 3-(3-trityl-5-(tritylamino)-3H-[1,2,3]triazolo[4,5-b]pyridin-7-yl)prop-2-yn-1-ol (7.88 g, 82%), as a brown solid. MS (ESI) m/z 673.9 (M+H).

Intermediate 2. A solution of the alkynyl alcohol of Step A (7.88 g, 11.7 mmol) in THF (50 mL) was added dropwise to a mixture of LAH (24.6 mmol) and sodium methoxide (0.063 g, 1.2 mmol) in THF (100 mL) at 0° C. under Ar, and the mixture was stirred for 1 h at 0° C. Dimethyl carbonate (2.11 g, 23.4 mmol) was then added at 0° C., and the reaction mixture was stirred for 10 minutes at 0° C., then cooled to −78° C. A solution of iodine (5.94 g, 23.4 mmol) in THF (20 mL) was added. The reaction mixture was allowed to warm to rt over a period of 30 minutes, stirred at rt for 20 minutes, and then quenched with 20 mL of MeOH. The mixture was diluted with water and EtOAc. The aqueous phase was extracted 3× with EtOAc, and the combined organics washed with brine, dried with Na₂SO₄, filtered and concentrated. The residue purified by flash chromatography on silica gel to yield the title compound as an orange solid (5.24 g, 55.9%). MS (ESI) m/z 802.0 (M+H).

Intermediate 3 (Compound 3-2 in Scheme 3). 7-((1H-Pyrazol-4-yl)methyl)-ditrityl-3H-[1,2,3]triazolo[4,5-b]pyridin-5-amine

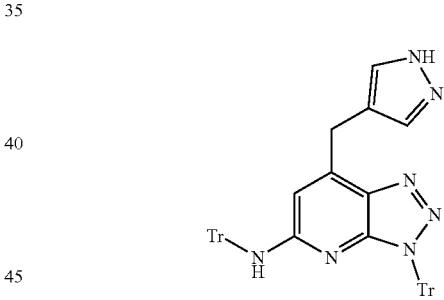

Step A. tert-Butyl 4-(bromomethyl)-1H-pyrazole-1-carboxylate

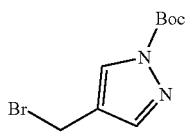

To a suspension of LAH (45.2 mL, 45.2 mmol, 1M in THF) in a flame-dried flask was added a solution of ethyl 1H-pyrazole-4-carboxylate (3.17 g, 22.6 mmol) in THF (20 mL) dropwise at 0° C. The reaction mixture was gradually warmed to rt and stirred overnight. The reaction mixture was cooled in an ice bath, and carefully quenched by sequential dropwise addition of 1.36 mL H₂O, and 10 mL of 1M NaOH, followed by 20 min of stirring. Solid MgSO₄ was added, the ice bath was removed, and stirring was continued for 30 min at rt. Solids were removed by filtration through Celite® and washed with THF, then MeOH. The combined filtrate was evaporated to give (1H-pyrazol-4-yl)methanol (1.75 g, 78.9%), as a white solid. $^1$H NMR (500 MHz, DMSO-d$_6$) δ 12.58 (br. s., 1H), 7.58 (s, 1H), 7.40 (s, 1H), 4.74 (t, J=5.5 Hz, 1H), 4.37 (d, J=5.2 Hz, 2H). A mixture of this alcohol (1.32 g, 13.5 mmol) and DMAP (0.033 g, 0.27 mmol) was suspended in 20 mL THF under nitrogen with stirring, while a solution of di-tert-butyl dicarbonate (2.94 g, 13.5 mmol) in 10 mL THF was added dropwise at 0° C. The turbid solution became clear. The reaction mixture was stirred at rt overnight. The reaction mixture was concentrated, combined with a second 1.52 g scale reaction and purified by silica gel chromatography to provide tert-butyl 4-(hydroxymethyl)-1H-pyrazole-1-carboxylate (4.07 g from 2.84 g SM, 71.4%) as a pale yellowish oil. MS(ESI) m/z 142.9 (M-tBu+H). To a solution of this Boc-protected pyrazole methyl alcohol (4.07 g, 20.5 mmol) in DCM (30 mL) was added triphenylphosphine (5.65 g, 21.6 mmol) at 0° C., followed by dropwise addition of a solution of CBr$_4$ (7.15 g, 21.6 mmol) in DCM (10 mL). The reaction mixture was gradually warmed to rt and stirred for 3 h. The reaction mixture was concentrated. tert-Butyl 4-(bromomethyl)-1H-pyrazole-1-carboxylate (4.26 g, 79.5%) was obtained as a colorless oil after flash chromatography and drying in vacuo. MS(ESI) m/z 206.9 (M+H-tBu).

Intermediate 3: A mixture of Intermediate 1 (5.62 g, 8.04 mmol), 5,5,5',5'-tetramethyl-2,2'-bi(1,3,2-dioxaborinane) (2.0 g, 8.8 mmol), KOAc (1.18 g, 12.0 mmol), Pd$_2$(dba)$_3$ (0.368 g, 0.402 mmol) and tricyclohexylphosphonium tetrafluoroborate (0.296 g, 0.804 mmol) was degassed and back-filled with argon several times before adding pre-degassed dioxane (27 mL). The resulting mixture was heated overnight at 100° C. To this reaction mixture was added PdCl$_2$(dppf)-DCM adduct (0.328 g, 0.402 mmol), followed by 2M aqueous Na$_2$CO$_3$ (20.1 mL) and a solution of the bromomethylpyrazole of Step A (2.1 g, 8.0 mmol) dissolved in THF (20 mL). The reaction mixture was blanketed under argon and heated to 70° C. for 5 h. MeOH (10 mL) and 1M NaOH (16 mL, 16 mmol) were added. The reaction mixture was stirred at 65° C. overnight. The reaction mixture was partitioned between DCM and water. The organic layer was washed with brine. The combined aqueous layers were re-extracted with DCM. The combined organics were dried with Na$_2$SO$_4$, filtered, and concentrated. Purification by flash chromatography provided Intermediate 3 as a mixture of trityl regioisomers (2.44 g, 43.4%) as a light brown solid. MS(ESI) m/z 700.3 (M+H).

Alternate Procedure for Preparation of Intermediate 3 (Via Scheme 7 and 9):

Step A.
2,6-(2,5-Dimethylpyrrol-1-yl)-4-formylpyridine

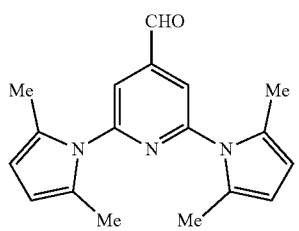 [SMILES: Cc1ccc(C)n1-c1cc(C=O)cc(-n2c(C)ccc2C)n1]

2,6-(2,5-Dimethylpyrrol-1-yl)pyridine prepared using a modification of procedure of Miller, L. F. et al. (*J. Med. Chem.*, 13:1022 (1970)) (2.65 g, 9.99 mmol) was dissolved in THF (50 mL) in an oven-dried 250 mL 3-neck flask under argon. The solution was cooled to 0° C. in an ice/salt water bath and nBuLi, 1.6 M in hexane (6.24 mL, 9.99 mmol) was added over ~2 min. The resulting solution was stirred for 5-6 min, then DMF (1.5 mL, 20 mmol) was added. Stirring was continued for 30 min in ice bath then at rt for 1 h. The mixture was quenched by addition of saturated aq. NH$_4$Cl solution and extracted with EtOAc (3×). The combined extracts were washed with brine, dried over Na$_2$SO$_4$, filtered and evaporated. The residue was purified by silica gel chromatography to provide the aldehyde as a bright yellow crystalline solid (1.51 g, 51.5%). $^1$H NMR (500 MHz, CDCl$_3$) δ 10.16 (s, 1H), 7.61 (s, 2H), 5.94 (s, 4H), 2.19 (s, 12H).

Step B. (2,6-Bis(2,5-dimethyl-1H-pyrrol-1-yl)pyridin-4-yl)methanol

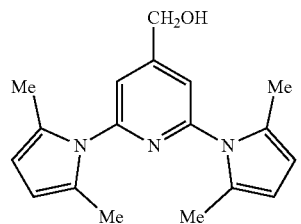 [SMILES: Cc1ccc(C)n1-c1cc(CO)cc(-n2c(C)ccc2C)n1]

To a suspension of the product of Step A (5.0 g, 17 mmol) in EtOH (75 mL) was added NaBH$_4$ (0.967 g, 25.6 mmol). The mixture was stirred for 4 h at rt, then quenched by addition of water. Most of the EtOH was removed on a rotary evaporator. Additional water was added and the mixture was extracted with EtOAc (3×). The combined extracts were dried over Na$_2$SO$_4$, filtered and evaporated to give the crude alcohol as a light yellow solid (5.0 g, 99%), which was used without further purification. MS(ESI) m/z 296.1 (M+H).

Step C. 4-Bromomethyl-2,6-(2,5-dimethylpyrrol-1-yl)-pyridine

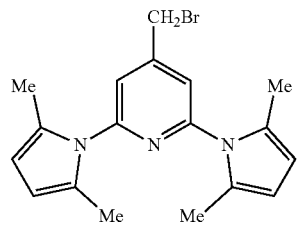

The crude alcohol from Step B (4.00 g, 13.5 mmol) was dissolved in DCM (65 mL), followed by addition of triphenylphosphine (4.26 g, 16.3 mmol) and CBr$_4$ (5.39 g, 16.3 mmol). The resulting solution was stirred at rt under argon overnight. The volatiles were removed under vacuum, and the residue was purified by silica gel chromatography to provide 4-bromomethyl-2,6-(2,5-dimethylpyrrol-1-yl)-pyridine (3.8 g, 78%). MS(ESI) m/z 357.9 (M+H). $^1$H NMR (500 MHz, CDCl$_3$) δ 7.23 (s, 2H), 5.90 (s, 4H), 4.49 (s, 2H), 2.16 (s, 12H).

Alternate Step C Procedure

LiBr (20.5 g, 237 mmol) was dissolved in 50 mL of THF. The crude alcohol from Step B (6.99 g, 23.7 mmol) was added using 20 mL THF to rinse in all of the material, followed by TEA (16.5 mL, 118 mmol). The solution was cooled to 0° C. in an ice/salt water bath with stirring, and then treated dropwise with methanesulfonic anhydride (10.3 g, 59.2 mmol) in THF (20 mL). The reaction mixture was stirred at 0° C. for 2 h then at rt. The reaction mixture was diluted with saturated aq. NaHCO$_3$ and EtOAc, and the phases were separated. The aqueous layer was re-extracted with EtOAc (3×). The combined organics were washed with 5% citric acid, water, and brine and then dried over Na$_2$SO$_4$, filtered and evaporated. The bromide was obtained as a brownish solid after drying overnight in vacuo (8.45 g, 100%). MS(ESI) m/z 359.9 (M+2+H)$^+$.

Step D. 4-((1H-Pyrazol-4-yl)methyl)-2,6-bis(2,5-dimethyl-1H-pyrrol-1-yl)pyridine

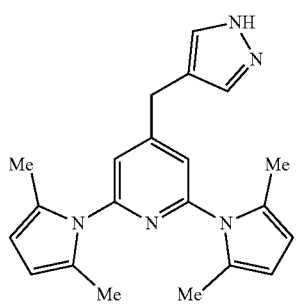 [SMILES: Cc1ccc(C)n1-c1cc(Cc2cn[nH]c2)cc(-n2c(C)ccc2C)n1]

In a 20 mL vial was added the bromide from Step C (1.00 g, 2.79 mmol), tert-butyl 4-(4,4,5,5-tetramethyl-1,3,2-dioxaborolan-2-yl)-1H-pyrazole-1-carboxylate (0.862 g, 2.93 mmol), (DtBPF)PdCl$_2$ (0.182 g, 0.279 mmol) and 3M K$_3$PO$_4$ (2.79 mL, 8.37 mmol). The reaction flask was purged with argon, and THF (9.30 mL) was added. The reaction mixture was heated at 70° C. for 2.5 hours. After cooling to rt, the mixture was transferred to a round bottom flask and methanol (4 mL) and 1N NaOH (4 mL) were added, followed by heating at 50° C. for 30 min to cleave the Boc protecting group. The reaction mixture was cooled to rt, diluted with EtOAc and washed with water and brine. The organic layer was dried over Na$_2$SO$_4$, filtered and concentrated. The residue was purified by silica gel chromatography to provide 4-((1H-Pyrazol-4-yl)methyl)-2,6-bis(2,5-dimethyl-1H-pyrrol-1-yl)pyridine (0.73 g, 75%) as a light tan foam which was used without further purification. MS(ESI) m/z 346.2 (M+H). $^1$H NMR (400 MHz, CDCl$_3$) δ 7.48 (s, 2H), 7.05 (s, 2H), 5.87 (s, 4H), 4.02 (s, 2H), 2.12 (s, 12H).

Step E. 2,6-bis(2,5-Dimethyl-1H-pyrrol-1-yl)-4-((1-(2-tosylethyl)-1H-pyrazol-4-yl)methyl)pyridine

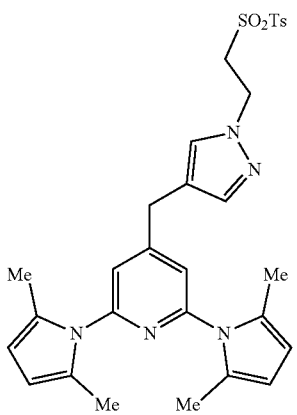

Pyrazole intermediate from Step D (3.45 g, 9.99 mmol) and 2-tosylethanol (4.0 g, 20 mmol) were dissolved in toluene (20 mL). Tris(butyl)phosphine (3.74 mL, 15.0 mmol) was added followed by 1,1'-azobis(N,N-dimethylformamide) (2.58 g, 15.0 mmol), and the reaction mixture was stirred at rt for 2 days. Reaction mixture was filtered and concentrated. The product was the purified by silica gel chromatography to provide 2,6-bis(2,5-dimethyl-1H-pyrrol-1-yl)-4-((1-(2-tosylethyl)-1H-pyrazol-4-yl)methyl)pyridine (3 g, 56.9%), as yellow oil. MS (ESI): m/z 527.8 (M+H).

Step F. 4-((1-(2-Tosylethyl)-1H-pyrazol-4-yl)methyl)pyridine-2,6-diamine

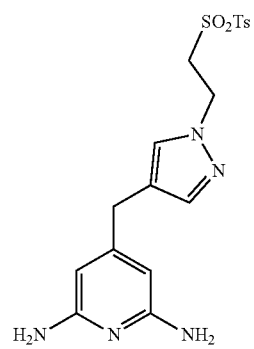

Intermediate from Step E (3.00 g, 5.69 mmol) was dissolved in EtOH (56 mL) along with hydroxylamine hydrochloride (7.90 g, 114 mmol) and TEA (7.92 mL, 56.9 mmol) in a pressure-rated vial. The reaction mixture was stirred for 2 days at 75° C. The reaction mixture was cooled to rt and diluted with EtOAc and water. The aqueous phase was extracted 3× with EtOAc, and the combined organic phases were washed with brine, dried with Na$_2$SO$_4$, filtered and concentrated to yield 4-((1-(2-tosylethyl)-1H-pyrazol-4-yl)methyl)pyridine-2,6-diamine, as an orange oil, which was brought forward without further purification. MS (ESI): m/z 371.8 (M+H).

Step G. 7-((1-(2-tosylethyl)-1H-pyrazol-4-yl)methyl)-3H-[1,2,3]triazolo[4,5-b]pyridin-5-amine

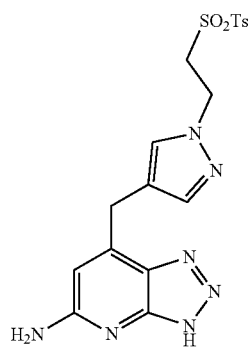

Diamine intermediate from Step F (2.11 g, 5.69 mmol) was dissolved in EtOAc (5 mL) and water. A solution of 4-chlorobenzenediazonium (9.24 mL, 7.39 mmol) was added followed by NaOAc (2.33 g, 28.4 mmol). The reaction mixture was stirred at rt under Ar for 3 hours. The reaction mixture was diluted with saturated aq. NaHCO$_3$ and EtOAc. The organic phase was washed with saturated aq. NaHCO$_3$2×, brine 1×, dried with Na$_2$SO$_4$, filtered and concentrated to yield (E)-3-((4-chlorophenyl)diazenyl)-4-((1-(2-tosylethyl)-1H-pyrazol-4-yl)methyl)pyridine-2,6-diamine, as an orange oil. MS (ESI): m/z 509.8 (M+H). The crude triamine (872 mg, 2.26 mmol) was dissolved in THF (100 mL). AcOH (0.129 mL, 2.26 mmol) was added, followed by isoamyl nitrite (0.273 mL, 2.03 mmol), and the reaction mixture stirred at rt under Ar overnight. An additional 0.2 equiv. of isoamyl nitrite was added, and stirring continued for 3 days at rt under Ar. The reaction mixture was concentrated, and crude 7-((1-(2-tosylethyl)-1H-pyrazol-4-yl)methyl)-3H-[1,2,3]triazolo[4,5-b]pyridin-5-amine was taken forward without further purification.

Step H. 7-((1-(2-tosylethyl)-1H-pyrazol-4-yl)methyl)-N,3-ditrityl-3H-[1,2,3]triazolo[4,5-b]pyridin-5-amine

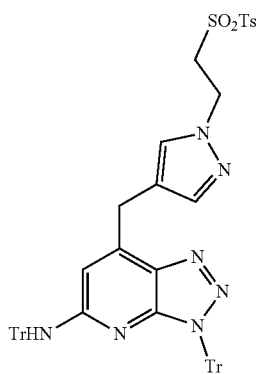

Triazolopyridine intermediate from Step G was protected as the bis-trityl analog using the procedure described for Intermediate 1. MS (ESI): m/z 882.0 (M+H).

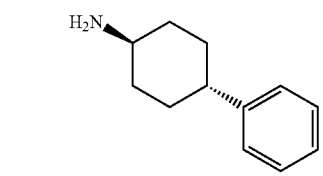 [SMILES: N[C@H]1CC[C@H](c2ccccc2)CC1]

Step A.
trans-N-benzhydryl-4-phenylcyclohexanamine

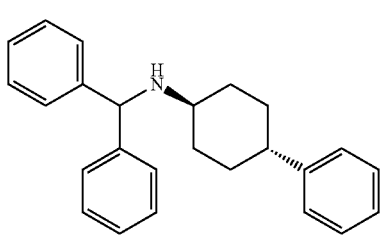 [SMILES: c1ccc(C(N[C@H]2CC[C@H](c3ccccc3)CC2)c2ccccc2)cc1]

To a solution of diphenylmethanamine (9.88 mL, 57.4 mmol) and 4-phenylcyclohexanone (10.0 g, 57.4 mmol) in DME (100 mL) was added Na(OAc)$_3$BH (18.3 g, 86.0 mmol) at rt. After the addition was finished, the reaction mixture was stirred for 3 hours. The reaction mixture was quenched carefully with saturated NaHCO$_3$, extracted with EtOAc 3×, dried over MgSO$_4$, filtered and concentrated. Purification on silica gel separated the cis isomer (first eluting peak) and desired trans isomer (major, second eluting peak) trans-N-benzhydryl-4-phenylcyclohexanamine (11.3 g, 57.8%). MS (ESI): m/z 342.3 (M+H).

Intermediate 4. To a mixture the benzhydryl amine from Step A (2.90 g, 8.49 mmol) and acetic acid (0.486 mL, 8.49 mmol) in MeOH (21 mL) and DCM (21 mL) was added 10% Pd/C (0.904 g, 0.849 mmol), and the reaction mixture was stirred under 30 psi H$_2$ overnight. The reaction mixture was filtered, and the filtrate was concentrated. The residue was taken up in 20 mL of 4M HCl in dioxane, and the solid was filtered off and washed with 4M HCl in dioxane and dried to provide Intermediate 4 (1.48 g, 82%) as a white solid. MS (ESI): m/z 176.1 (M+H).

Intermediate 5.
4-Phenylbicyclo[2.2.2]octan-1-amine, HCl

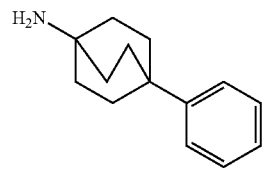 [SMILES: NC12CCC(c3ccccc3)(CC1)CC2]

Step A. 4-Acetyl-4-(4-bromophenyl)heptanedinitrile

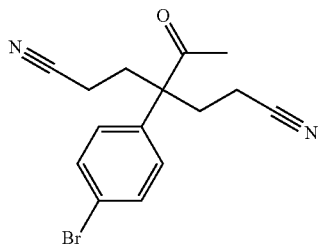 [SMILES: CC(=O)C(CCC#N)(CCC#N)c1ccc(Br)cc1]

To 1-(4-bromophenyl)propan-2-one (15.0 g, 70.4 mmol) dissolved in t-butanol (17.6 mL) was added N,N,N-trimethyl-1-phenylmethanaminium hydroxide in MeOH (1.9 mL, 4.2 mmol), followed by acrylonitrile (9.3 mL, 140 mmol) dropwise with use of a water cooling bath to regulate exotherm. After addition was complete, the reaction mixture was stirred an additional hour. The reaction mixture was diluted with water, further diluted with toluene and ether, neutralized with 4.3 mL 1N HCl, and the layers were separated. The aqueous layer was washed 1× with ether. The combined organic layers were washed with water and brine. The organic layer was concentrated, and the crude product was taken forward without further purification (28.1 g, 100%). MS (ESI) m/z 321.1 (M+H).

Step B. 4-Acetyl-4-(4-bromophenyl)heptanedioic acid

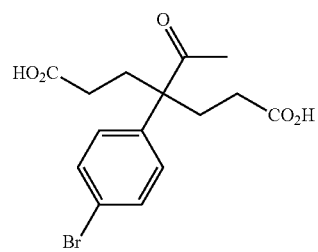 [SMILES: CC(=O)C(CCC(=O)O)(CCC(=O)O)c1ccc(Br)cc1]

To a slurry of the dinitrile of Step A (28.1 g, 70.4 mmol) in water (78 mL) was added KOH (11.0 g, 200 mmol), and the mixture was heated to reflux overnight. The reaction mixture was cooled. The aqueous phase was washed with ether, then acidified with 16 mL of conc. HCl. The resulting precipitate was collected by filtration and washed with water to furnish 4-acetyl-4-(4-bromophenyl)heptanedioic acid (26.0 g, 103%) which was used directly in the next step. MS (ESI): m/z 359.0 (M+H).

Step C. 4-Acetyl-4-(4-bromophenyl)cyclohexanone

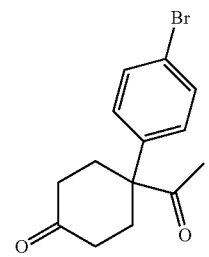 [SMILES: CC(=O)C1(c2ccc(Br)cc2)CCC(=O)CC1]

To a slurry of the diacid of Step B (16.8 g, 46.9 mmol) in Ac$_2$O (22.1 mL, 235 mmol) was added KOAc (0.138 g, 1.41 mmol), and the mixture was refluxed for 2 hours. The acetic acid and acetic anhydride was removed by evaporation. The flask containing the product residue was fitted with a 6" glass condensing tube, and the reaction mixture was heated to 210° C. with stirring for 1 h. The residue was purified by flash chromatography to furnish 4-acetyl-4-(4-bromophenyl)cyclohexanone (3.2 g, 23%). MS (ESI): m/z 297.0 (M+H). $^1$H NMR (500 MHz, CDCl$_3$) δ 7.56 (d, J=8.5 Hz, 2H), 7.25 (d, J=8.8 Hz, 2H), 2.66-2.58 (m, 2H), 2.56-2.47 (m, 2H), 2.46-2.38 (m, 2H), 2.34-2.25 (m, 2H), 2.03 (s, 3H).

Step D. 4-(Benzylamino)-1-(4-bromophenyl)bicyclo[2.2.2]octan-2-one

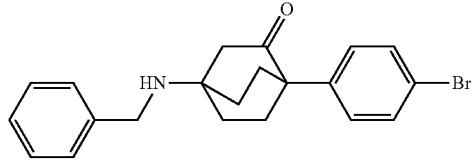 [SMILES: O=C1CC2(NCc3ccccc3)CCC1(c1ccc(Br)cc1)CC2]

To a solution of cyclohexanone intermediate of Step C (0.20 g, 0.68 mmol) dissolved in toluene (1.4 mL) was added benzylamine (0.22 mL, 2.0 mmol) and p-toluenesulfonic acid (1.0 mg, 7.0 µmol), and the solution was heated to reflux with a Dean-Stark trap. After 2 hours, the reaction mixture was cooled to rt, and 0.66 mL of 3M HCl was added. Reaction mixture was stirred overnight at rt. The mixture was then partitioned between 1.5 M pH 7.4 buffer and ethyl acetate, and the layers were separated. The organic layer was dried over MgSO$_4$, filtered and concentrated to furnish a brown residue. The residue was purified via flash chromatography to furnish 4-(benzylamino)-1-(4-bromophenyl)bicyclo[2.2.2]octan-2-one (0.23 g, 0.60 mmol, 88%). MS (ESI) m/z 386.1 (M+H), $^1$H NMR (400 MHz, CDCl$_3$) δ 7.47 (d, J=8.6 Hz, 2H), 7.36-7.32 (m, 5H), 7.07 (d, J=8.6 Hz, 2H), 3.79 (s, 2H), 2.56 (s, 2H), 2.30-2.18 (m, 2H), 2.16-2.03 (m, 2H), 2.02-1.83 (m, 4H).

Step E. N-benzyl-4-(4-bromophenyl)bicyclo[2.2.2]octan-1-amine

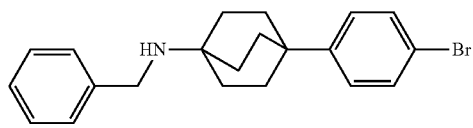 [SMILES: Brc1ccc(C23CCC(NCc4ccccc4)(CC2)CC3)cc1]

To the ketone intermediate of Step D (4.06 g, 10.6 mmol) was added hydrazine hydrate (2.27 g, 45.4 mmol), and the mixture was heated to 120° C. for 2.5 h. The mixture was cooled, and KOH (2.96 g, 52.8 mmol) and diglyme (19.2 mL) were added. The reaction mixture was heated to 160° C., and hydrazine was distilled off. The reaction mixture was then heated to 220° C. for 2 hours. The reaction mixture was poured into water and extracted into ether 2×. The organic layer was dried over $Na_2SO_4$, filtered and concentrated to furnish N-benzyl-4-(4-bromophenyl)bicyclo[2.2.2]octan-1-amine (3.91 g, 100%). MS (ESI): m/z 370.3/372.3 (M+H).

Intermediate 5. To a solution of the N-benzylamine intermediate of Step E (3.91 g, 10.6 mmol) in EtOH (52.8 mL) (w/AcOH added) was added Pd/C (1.12 g, 1.06 mmol), and the reaction mixture was stirred under $H_2$ (55 psi). The reaction mixture was filtered through Celite® and concentrated to furnish Intermediate 5. (1.5 g, 71%). MS (ESI): m/z 202.4 (M+H).

Intermediate 6. 4-(4,4,5,5-Tetramethyl-1,3,2-dioxaborolan-2-yl)-1-(3-((triisopropylsilyl)oxy)benzyl)-1H-pyrazole

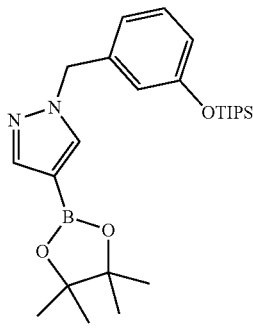

Step A. Methyl 3-((triisopropylsilyl)oxy)benzoate

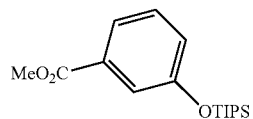

Methyl 3-hydroxybenzoate (10.0 g, 65.7 mmol) and imidazole (5.28 g, 78.0 mmol) were dissolved in DMF (43.8 mL). The solution was cooled to 0° C. in an ice/salt water bath while TIPS-Cl (15.9 mL, 67.7 mmol) was added dropwise. After completion of addition, stirring was continued at 0° C. for ~1 h, then at rt overnight. Additional imidazole (2.64 g, 39.0 mmol) and TIPS-Cl (8 mL, 33.8 mmol) were added. The reaction mixture was stirred for another 5 h at rt. The reaction mixture was diluted with water and extracted 3× with $Et_2O$. The combined extracts were washed with water and brine, then dried over anhydrous sodium sulfate, filtered and evaporated. The crude product was purified by silica gel chromatography to provide the desired TIPS protected alcohol (18.2 g, 90%). MS (ESI): m/z 309.2 (M+H) $^1$H NMR (500 MHz, DMSO-$d_6$) δ 7.56 (d, J=7.7 Hz, 1H), 7.46-7.33 (m, 2H), 7.20-7.11 (m, 1H), 1.32-1.15 (m, 3H), 1.10-1.00 (m, 18H).

Step B. (3-((Triisopropylsilyl)oxy)phenyl)methanol

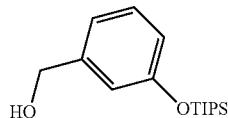

The TIPS-protected intermediate from Step A (18.2 g, 59.1 mmol) was dissolved in THF (236 mL) with stirring under argon. The solution was cooled to 0° C., and a solution of $LiBH_4$, 2M in THF (59.1 mL, 118 mmol) was added in rapid dropwise fashion. MeOH (4.78 mL, 118 mmol) was then added slowly dropwise. The reaction mixture was stirred overnight allowing the ice to melt, and the reaction to gradually assume rt. The reaction mixture was then heated to reflux for 4-5 h to drive the reduction to completion. The reaction flask was cooled to rt, then placed in an ice bath, and the reaction was quenched with water, then 1M NaOH. EtOAc was added, and the mixture was stirred to dissolve most of the solids. The phases were separated, and the aqueous was re-extracted 2× with EtOAc. Remaining solid was carefully dissolved with a little 1M HCl and water and added to the aqueous layer which was extracted once more with EtOAc. The combined extracts were washed with brine, then dried over $Na_2SO_4$, filtered and evaporated to yield (3-((triisopropylsilyl)oxy)phenyl)methanol as a colorless liquid (16 g, 97%). $^1$H NMR (500 MHz, $CDCl_3$) δ 7.20 (t, J=7.70 Hz, 1H), 6.92 (d, J=7.43 Hz, 1H), 6.90 (d, J=1.93 Hz, 1H), 6.80 (dd, J=1.79, 8.12 Hz, 1H), 4.64 (s, 2H), 1.58 (br s, 1H), 1.20-1.32 (m, 3H), 1.10 (d, J=7.15 Hz, 18H).

Intermediate 6. A mixture of 4-(4,4,5,5-tetramethyl-1,3,2-dioxaborolan-2-yl)-1H-pyrazole (0.692 g, 3.57 mmol), and the benzyl alcohol from step B (1.00 g, 3.57 mmol) in toluene (7.13 mL) was sonicated for 10 min to obtain a homogeneous solution. Tris(butyl)phosphine (1.34 mL, 5.35 mmol) was added, followed by TMAD (0.921 g, 5.35 mmol), and the reaction mixture was stirred at rt overnight. The reaction mixture was filtered, the solid washed with additional toluene, and filtrate evaporated. The product was the purified by silica gel chromatography to provide Intermediate 6 (1.29 g, 79%) as a white solid. MS (ESI): m/z 457.2 (M+H). $^1$H NMR (500 MHz, $CDCL_3$) δ 7.83 (s, 1H), 7.67 (s, 1H), 7.19 (t, J=7.8 Hz, 1H), 6.88-6.79 (m, 2H), 6.70 (s, 1H), 5.28 (s, 2H), 1.33 (s, 12H), 1.25-1.19 (m, 3H), 1.08 (d, J=7.2 Hz, 18H).

Intermediate 7. (Z)-3-(1-(3-((triisopropylsilyl)oxy)benzyl)-1H-pyrazol-4-yl)-3-(3-trityl-5-(tritylamino)-3H-[1,2,3]triazolo[4,5-b]pyridin-7-yl)acrylaldehyde

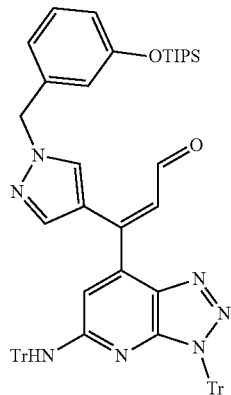

Step A. (Z)-3-(1-(3-((triisopropylsilyl)oxy)benzyl)-1H-pyrazol-4-yl)-3-(3-trityl-5-(tritylamino)-3H-[1,2,3]triazolo[4,5-b]pyridin-7-yl)prop-2-en-1-ol

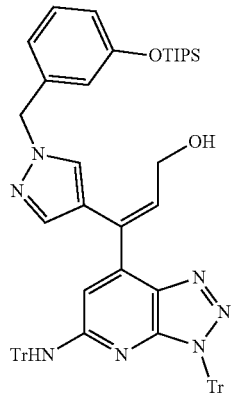

To a solution of $K_2CO_3$ (1.29 g, 9.35 mmol) in water (6.24 mL) was added a solution of Intermediate 6 (0.854 g, 1.87 mmol) in THF (6.24 mL), followed by a solution of Intermediate 2 (1.50 g, 1.87 mmol) in THF (6.24 mL). The mixture was degassed by bubbling argon through the mixture for 10 min, and then $PdCl_2(dppf)\text{-}CH_2Cl_2$ Adduct (0.153 g, 0.187 mmol) was added. The reaction mixture was heated at 80° C. for 3 hours, then cooled to rt. The reaction mixture was diluted with EtOAc and water. Phases were separated, and organic layer washed with water and brine, then dried over $Na_2SO_4$, filtered and evaporated. The crude was the purified by silica gel chromatography to provide the product (1.01 g, 53.7%) as a yellow foam. MS (ESI): m/z 1004.6 (M+H).

Intermediate 7: The allylic alcohol intermediate from Step A (1.00 g, 0.996 mmol) was dissolved in DCM (10 mL) and $MnO_2$ (0.866 g, 9.96 mmol) was added. The reaction mixture was stirred at rt overnight. An additional portion of $MnO_2$ (0.300 g, 3.45 mmol) was added and stirring was continued for 7 hours. The reaction mixture was filtered through a pad of Celite® and the filtrate was concentrated to give Intermediate 7 (0.912 g, 91%). MS (ESI): m/z 1002.4 (M+H).

Intermediate 8. (S)-4-Amino-1phenylbicyclo[2.2.2]octan-2-ol, TFA salt

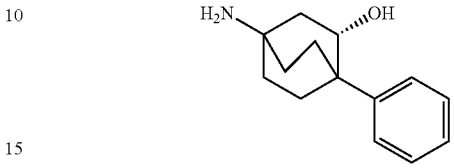

Step A. 4-(Benzylamino)-1-(4-bromophenyl)bicyclo[2.2.2]octan-2-ol

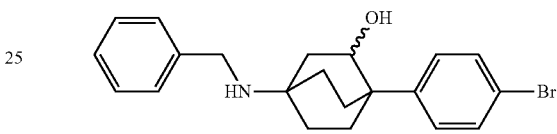

To a solution of the ketone from Intermediate 5, Step D (7.03 g, 18.3 mmol) dissolved in EtOH (340 mL) at 0° C. was added $NaBH_4$ (1.04 g, 27.4 mmol), and the reaction mixture was stirred at rt for 3 days. The reaction mixture was concentrated, partitioned between brine and EtOAc, and the aqueous layer was separated and washed 1× with EtOAc. The combined organic layers were dried over $MgSO_4$, and purified via flash chromatography to furnish 4-(benzylamino)-1-(4-bromophenyl)bicyclo[2.2.2]octan-2-ol (5.3 g, 75%). MS (ESI) m/z 388.0 (M+H).

Step B. tert-Butyl benzyl(4-(4-bromophenyl)-3-oxobicyclo[2.2.2]octan-1-yl)carbamate

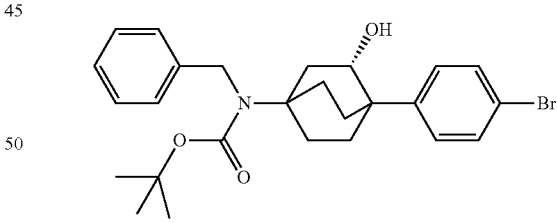

To a solution of the intermediate amine from Step A (5.0 g, 13 mmol) in THF (22 mL) was added 1N NaOH (22 mL) followed by $Boc_2O$ (3.02 mL, 13.0 mmol). The biphasic mixture was stirred overnight at 50° C. Additional $Boc_2O$ (3.02 mL, 13.0 mmol) was added, and the reaction mixture was stirred overnight. The reaction mixture was partitioned between EtOAc and water, and the organic phase was dried over $MgSO_4$, filtered and concentrated. The residue was purified via flash chromatography to furnish tert-butyl benzyl(4-(4-bromophenyl)-3-oxobicyclo[2.2.2]octan-1-yl)carbamate (3.0 g, 6.2 mmol, 48%), $^1H$ NMR (400 MHz, $CDCl_3$) δ 7.43 (d, J=8.6 Hz, 2H), 7.37-7.30 (m, 2H), 7.30-7.22 (m, 1H), 7.20 (d, J=7.3 Hz, 2H), 7.04-6.93 (m, 2H), 4.63 (s, 2H), 3.06 (s, 2H), 2.37-2.07 (m, 6H), 2.05-1.92 (m, 2H), 1.47 (s, 9H). MS (ESI) m/z 430.0 (M+H-tBu).

Step C. tert-Butyl (S)-benzyl(4-(4-bromophenyl)-3-hydroxybicyclo[2.2.2]octan-1-yl)carbamate

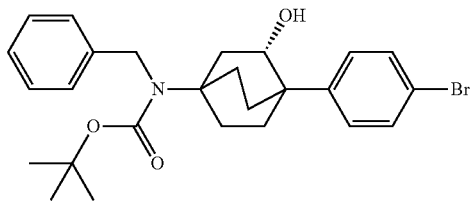 [SMILES: CC(C)(C)OC(=O)N(Cc1ccccc1)C12CCC(c3ccc(Br)cc3)(CC1)[C@@H](O)C2]

To a solution of the intermediate ketone of Step B (2.0 g, 4.1 mmol) in EtOH (41 mL) at 0° C. was added NaBH₄ (0.16 g, 4.1 mmol), and the reaction mixture was stirred for 1 hour. The reaction mixture was diluted with water, and the resultant precipitate was filtered and dried under vacuum overnight to furnish racemic tert-butyl benzyl(4-(4-bromophenyl)-3-hydroxybicyclo[2.2.2]octan-1-yl)carbamate (1.6 g, 80%), $^1$H NMR (400 MHz, CDCl₃) δ 7.43 (d, J=8.6 Hz, 2H), 7.34-7.28 (m, 2H), 7.24-7.15 (m, 5H), 4.59 (s, 2H), 4.13-4.04 (m, 1H), 2.73 (ddd, J=13.1, 9.5, 3.1 Hz, 1H), 2.40-2.29 (m, 1H), 2.25-2.12 (m, 2H), 2.10-1.98 (m, 2H), 1.94 (dt, J=13.4, 3.1 Hz, 1H), 1.91-1.83 (m, 1H), 1.77-1.62 (m, 2H), 1.44 (s, 9H), 1.23 (d, J=2.6 Hz, 1H). MS (ESI) m/z 386.1/388.1 (M+H-BOC). The enantiomers were separated by Chiral SFC (Chiralpak OJ-H eluted with 15% MeOH/85% CO at 150 bar and 40° C.) to provide tert-butyl (S)-benzyl (4-(4-bromophenyl)-3-hydroxybicyclo[2.2.2]octan-1-yl) carbamate and tert-butyl (R)-benzyl(4-(4-bromophenyl)-3-hydroxybicyclo[2.2.2]octan-1-yl)carbamate in >99.5% ee.

Intermediate 8. tert-Butyl (S)-benzyl(4-(4-bromophenyl)-3-hydroxybicyclo[2.2.2]octan-1-yl)carbamate was dissolved in DCM (40 mL) and TFA (8 mL) and stirred for 1 h. The reaction mixture was concentrated, and the residue taken up in 200 mL of EtOH and 10% Pd—C (580 mg) was added. The mixture was stirred under 55 psi hydrogen gas overnight. The catalyst was removed by filtration through Celite®. The filtrate was evaporated to provide the title compound, which was used without further purification. MS (ESI): 217.9 (M+H).

Intermediate 9. (1R, 2R, 4R)-4-amino-2-benzylcyclopentanol, HCl

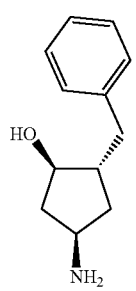 [SMILES: N[C@@H]1C[C@@H](Cc2ccccc2)[C@H](O)C1]

Step A. cis-tert-Butyl-6-oxabicyclo[3.1.0]hexan-3-ylcarbamate

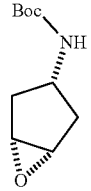

Solid NaHCO₃ (2.06 g, 24.6 mmol) and m-CPBA (4.04 g, 16.4 mmol) were added in portions to a solution of tert-butyl cyclopent-3-en-1-ylcarbamate (2.50 g, 13.6 mmol) in DCM (68 mL) under nitrogen with stirring at 0° C. The turbid solution became clear. The reaction mixture was left stirring at rt for 3 days. Aqueous 10% Na₂SO₃ (50 mL) was added, and the two layers were separated. The aqueous layer was extracted 3× with DCM, and the combined organic layers were washed with 10% aq. Na₂SO₃, saturated aq. NaHCO₃ and water. The combined organics were dried over Na₂SO₄, filtered and evaporated. The product was the purified by silica gel chromatography to provide the racemic cis-epoxide (1.97 g, 72.4%)$^1$H NMR (500 MHz, CDCl₃) δ 4.98 (br d, J=8.5 Hz, 1H), 4.25-4.10 (m, 1H), 3.57 (s, 2H), 2.10-2.01 (m, 2H), 2.00-1.93 (m, 2H), 1.44 (s, 9H). The trans-epoxide was also isolated as a minor product, trans-tert-butyl-6-oxabicyclo[3.1.0]hexan-3-ylcarbamate (0.461 g, 17%). $^1$H NMR (500 MHz, CDCl₃) δ 4.38 (br s, 1H), 3.82 (br s, 1H), 3.50 (s, 2H), 2.52 (dd, J=14.0, 7.7 Hz, 2H), 1.54-1.48 (m, 2H), 1.46 (s, 9H).

Step B. tert-butyl ((1R,3R,4R)-3-benzyl-4-hydroxycyclopentyl)carbamate

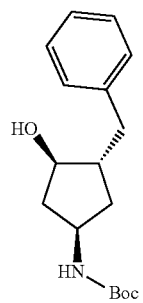

To a solution of the epoxide from Step A (1.97 g, 9.89 mmol) in THF (49 mL) was added a 2M solution of benzylmagnesium chloride in THF (9.89 mL, 19.8 mmol) dropwise at 0° C. The reaction mixture was gradually warmed up to rt and stirred overnight. The reaction mixture was quenched with sat'd aq. NH₄Cl at 0° C., diluted with water and then extracted with EtOAc (3×). The combined organics were dried over Na₂SO₄ and concentrated. The product was purified by silica gel chromatography to provide the racemate (0.649 g, 22.5%). MS (ESI): m/z 292.0 (M+H). Chiral SFC separation (chiralpak IC eluted with 10% MeOH/90% CO at 150 bar, and 40° C.) provided the single enantiomers, tert-butyl ((1R,3R,4R)-3-benzyl-4-hydroxycyclopentyl)-carbamate and tert-butyl ((1S,3S,4S)-3-benzyl-4-hydroxycyclopentyl)carbamate in >99% ee.

Intermediate 9. To a solution of tert-butyl ((1R,3R,4R)-3-benzyl-4-hydroxycyclopentyl)-carbamate from Step B (255 mg, 0.875 mmol) in dioxane (1 mL) was added a solution of 4N HCl in dioxane (2.19 mL, 8.75 mmol). The reaction mixture was stirred at rt for 5 h. The solvents were removed, and the residue was triturated with Et$_2$O to give Intermediate 9 as a white solid. MS (ESI): m/z 192.0 (M+H).

Intermediate 10. trans-4-Benzylpyrrolidin-3-ol, HCl, Enantiomer B

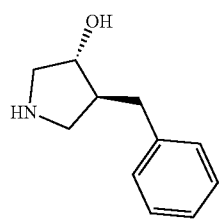 [SMILES: O[C@H]1CNC[C@@H]1Cc1ccccc1]

Step A. trans-tert-Butyl 3-benzyl-4-hydroxypyrrolidine-1-carboxylate, Enantiomer B

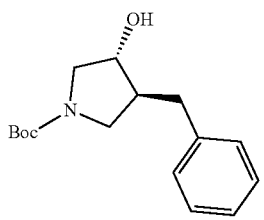 [SMILES: CC(C)(C)OC(=O)N1C[C@H](Cc2ccccc2)[C@@H](O)C1]

To a solution of tert-butyl 6-oxa-3-azabicyclo[3.1.0]hexane-3-carboxylate (1.00 g, 5.40 mmol) in THF (27 mL) was added a 2M solution of benzylmagnesium chloride in THF (6.75 mL, 13.5 mmol) dropwise at 0° C. The reaction mixture was gradually warmed up to rt and stirred overnight. The reaction mixture was quenched with aq. sat'd. NH$_4$Cl at 0° C., then extracted with EtOAc (3×). The combined organics were dried over Na$_2$SO$_4$, filtered and concentrated. Purification by silica gel chromatography provided the trans products as a racemic mixture (1.37 g, 91%). MS (ESI): m/z 278.1 (M+H). Chiral separation (chiralpak AD eluted with 10% MeOH/90% CO at 150 bar, and 40° C.) provided the single enantiomers, (3S,4R)-tert-butyl 3-benzyl-4-hydroxypyrrolidine-1-carboxylate and (3R,4S)-tert-butyl 3-benzyl-4-hydroxypyrrolidine-1-carboxylate in >99% ee. Absolute stereochemistry of the enantiomers was not determined.

Intermediate 10. To a solution of the second eluting enantiomer of Step A (100 mg, 0.361 mmol) in dioxane (1 mL) was added 4 N HCl in dioxane (0.90 mL, 3.6 mmol). The reaction mixture was stirred at rt for 5 h. The solvents were removed to give Intermediate 10 as a white solid. MS (ESI): m/z 178.1 (M+H).

Example 1. 7-(4-phenyl-1-(1-((1,2,3,4-tetrahydroisoquinolin-6-yl)methyl)-1H-pyrazol-4-yl)butyl)-3H-[1,2,3]triazolo[4,5-b]pyridin-5-amine, 2 TFA

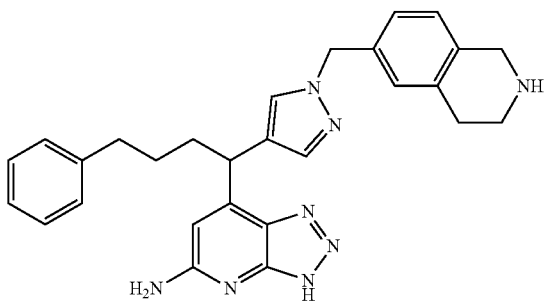 [SMILES: Nc1cc(C(CCCc2ccccc2)c2cnn(Cc3ccc4c(c3)CCNC4)c2)c2nn[nH]c2n1]

1A. tert-Butyl 6-(hydroxymethyl)-3,4-dihydroisoquinoline-2(1H)-carboxylate

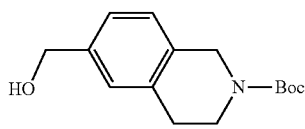

A mixture of 2-(tert-butoxycarbonyl)-1,2,3,4-tetrahydroisoquinoline-6-carboxylic acid (0.40 g, 1.4 mmol), and NMM (0.238 mL, 2.16 mmol) in THF (14.4 mL) was treated with IBCF (0.227 mL, 1.73 mmol)) at 0° C., and the reaction mixture was stirred for 5 minutes. A solution of NaBH$_4$ (0.218 g, 5.77 mmol) dissolved in 5 mL of water was then added portionwise. The reaction mixture was allowed to warm to rt and was stirred for 2 h. The reaction mixture was quenched with saturated aq. ammonium chloride, and extracted 3× with EtOAc. The combined extracts were washed with brine, dried with Na$_2$SO$_4$, filtered and concentrated to yield 1A as a yellow oil which was used in the next step without further purification. MS (ESI) m/z 263.9 (M+H) 207.9 (M-tBu).

1B. tert-Butyl 6-((4-((3-trityl-5-(tritylamino)-3H-[1,2,3]triazolo[4,5-b]pyridin-7-yl)methyl)-1H-pyrazol-1-yl)methyl)-3,4-dihydroisoquinoline-2(1H)-carboxylate

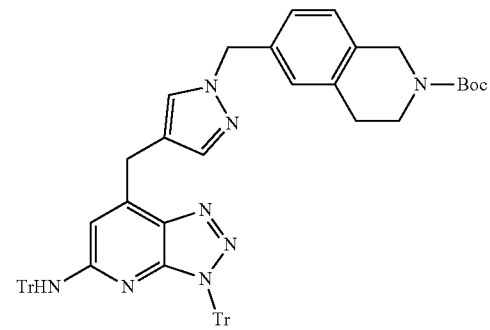

Intermediate 3 (185 mg, 0.264 mmol) and 1A (139 mg, 0.529 mmol) were dissolved in toluene (0.6 mL). Tris(n-butyl)phosphine (0.099 mL, 0.40 mmol) was added followed by TMAD (68.3 mg, 0.397 mmol), and the reaction mixture was stirred at rt overnight. The reaction mixture was filtered, and the filtrate was concentrated. The crude was purified by silica gel chromatography to yield 1B as a yellow solid (170 mg, 68.0%). MS (ESI) m/z 945.1 (M+H).

1C. tert-butyl 6-((4-(4-phenyl-1-(3-trityl-5-(tritylamino)-3H-[1,2,3]triazolo[4,5-b]pyridin-7-yl)butyl)-1H-pyrazol-1-yl)methyl)-3,4-dihydroisoquinoline-2(1H)-carboxylate

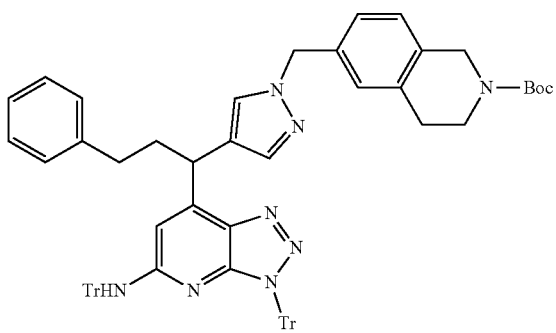

1B (170 mg, 0.180 mmol) was dissolved in DMF (5 mL). The solution was deoxygenated by evacuating and backfilling with Ar 3× and then cooled to 0° C. KOtBu (0.540 mL, 0.540 mmol) was added followed by (3-bromopropyl)benzene (0.055 mL, 0.36 mmol). Deoxygenation was repeated, and the reaction mixture was stirred at rt for 2 h. The reaction mixture was quenched with saturated aq. ammonium chloride, then extracted 3× with EtOAc. The combined organics were washed with brine, dried with $Na_2SO_4$, filtered and concentrated to yield 1C which was used in the next step without purification. MS (ESI) m/z 821.2 (M-trityl+H).

Example 1. 1C (191 mg, 0.180 mmol) was dissolved in a mixture of TFA (5 mL)/DCM (5 mL). Triethylsilane (0.143 mL, 0.898 mmol) was added, and the reaction mixture was stirred at rt for 1 h and concentrated. The product was purified by prep RP-HPLC to provide the title compound as the bis-TFA salt (12.9 mg, 10.2%) MS (ESI): m/z 479.4 (M+H). $^1$H NMR (500 MHz, $CD_3OD$) δ 7.66 (s, 1H), 7.49 (s, 1H), 7.21-7.26 (m, J=7.40 Hz, 2H), 7.07-7.19 (m, 5H), 7.00-7.04 (m, 1H), 6.57-6.62 (m, 1H), 5.27 (s, 2H), 4.43 (t, J=7.70 Hz, 1H), 4.33 (s, 2H), 3.47 (t, J=6.33 Hz, 2H), 3.03 (t, J=6.33 Hz, 2H), 2.58-2.73 (m, 2H), 2.24-2.37 (m, 1H), 2.10-2.22 (m, 1H), 1.54-1.72 (m, 2H). HPLC retention time: 1.22 min (Method C).

The following examples were prepared using the procedures described for Ex. 1 by replacing the 3-phenylpropyl bromide in step 1C with the indicated alkyl halide.

Example 2. 7-{1-[1-(1,2,3,4-tetrahydroisoquinolin-6-ylmethyl)-1H-pyrazol-4-yl]butyl}-3H-[1,2,3]triazolo[4,5-b]pyridin-5-amine, 2TFA

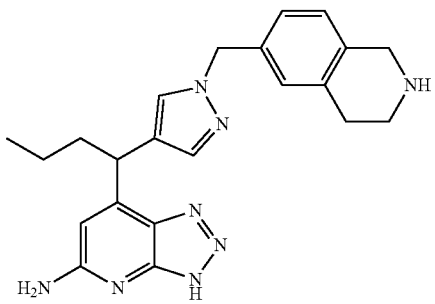 [SMILES: CCCC(c1cnn(Cc2ccc3c(c2)CCNC3)c1)c1cc(N)nc2[nH]nnc12]

Prepared with propyl iodide. MS (ESI): m/z 403.3 (M+H). $^1$H NMR (500 MHz, DMSO-$d_6$) δ 9.01 (br. s., 2H), 7.97 (s, 1H), 7.71 (s, 1H), 7.42 (s, 1H), 7.01-7.20 (m, 3H), 6.42 (br. s., 1H), 5.22 (s, 2H), 4.18-4.33 (m, 3H), 3.31-3.42 (m, J=5.50 Hz, 2H), 2.93 (t, J=6.19 Hz, 2H), 1.90-2.22 (m, 2H), 1.11-1.34 (m, 2H), 0.89 (t, J=7.29 Hz, 3H). HPLC retention time=1.04 min (Method C).

Example 3. 7-{1-[1-(1,2,3,4-tetrahydroisoquinolin-6-ylmethyl)-1H-pyrazol-4-yl]ethyl}-3H-[1,2,3]triazolo[4,5-b]pyridin-5-amine, 2TFA

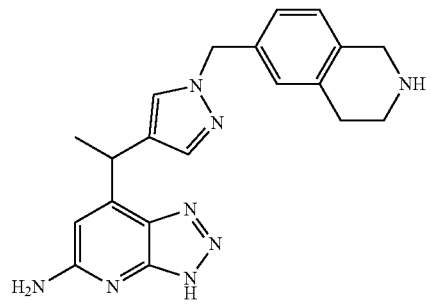 [SMILES: CC(c1cnn(Cc2ccc3c(c2)CCNC3)c1)c1cc(N)nc2[nH]nnc12]

Prepared with methyl iodide. MS (ESI) m/z (M+H)=375.25. $^1$H NMR (500 MHz, $CD_3OD$) δ 7.70 (s, 1H), 7.52 (s, 1H), 7.20 (s, 2H), 7.11 (s, 1H), 6.56-6.67 (m, 1H), 5.30 (s, 2H), 4.56-4.68 (m, 1H), 4.35 (s, 2H), 3.46-3.57 (m, 2H), 3.06-3.15 (m, 2H), 1.79 (d, J=7.15 Hz, 3H). HPLC retention time: 0.95 min (Method C).

Example 4. 7-(3-(benzyloxy)-1-(((1,2,3,4-tetrahydroisoquinolin-6-yl)methyl)-1H-pyrazol-4-yl)propyl)-3H-[1,2,3]triazolo[4,5-b]pyridin-5-amine, 2TFA

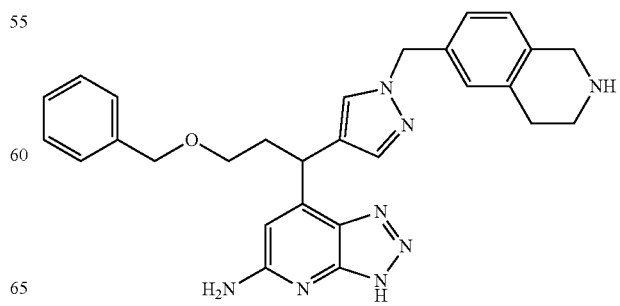

Prepared with (2-bromoethoxymethyl)benzene. MS (ESI): m/z 495.3 (M+H). $^1$H NMR (500 MHz, DMSO-$d_6$) δ 7.67 (s, 1H), 7.40 (s, 1H), 7.19-7.35 (m, 5H), 6.94 (s, 2H), 6.90 (s, 1H), 6.52 (s, 2H), 6.39 (s, 1H), 5.15 (s, 2H), 4.44 (t, J=7.84 Hz, 1H), 4.39 (s, 2H), 3.81 (s, 3H), 2.86-2.96 (m, 3H), 2.74 (s, 1H), 2.62 (t, J=5.78 Hz, 2H), 2.16-2.41 (m, J=6.60 Hz, 2H), 1.91 (s, 2H). HPLC retention time: 1.15 min (Method C).

Example 5. 7-{4,4-diphenyl-1-[1-(1,2,3,4-tetrahydroisoquinolin-6-ylmethyl)-1H-pyrazol-4-yl]butyl}-3H-[1,2,3]triazolo[4,5-b]pyridin-5-amine, 2 TFA

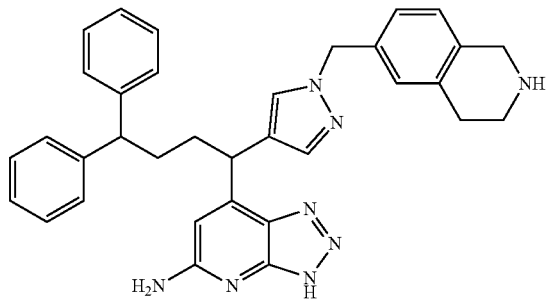 [SMILES: Nc1cc(C(CCC(c2ccccc2)c2ccccc2)c2cnn(Cc3ccc4c(c3)CCNC4)c2)c2nn[nH]c2n1]

Prepared with (3-bromopropane-1,1-diyl)dibenzene. MS (ESI): m/z 555.35 (M+H). $^1$H NMR (500 MHz, DMSO-$d_6$) δ 8.96 (br. s., 2H), 7.67 (s, 1H), 7.37 (s, 1H), 7.18-7.29 (m, 8H), 7.10-7.18 (m, 3H), 7.04-7.10 (m, 1H), 7.01 (s, 1H), 6.29-6.41 (m, 1H), 5.20 (s, 2H), 4.26-4.35 (m, 1H), 4.22 (br. s., 2H), 3.94-4.00 (m, J=6.30, 6.30 Hz, 1H), 3.92 (s, 1H), 3.28-3.41 (m, 2H), 2.84-2.90 (m, J=5.60, 5.60 Hz, 2H), 1.97 (br. s., 4H). HPLC retention time: 1.39 min (Method C).

Example 6. 7-{4-cyclohexyl-1-[1-(1,2,3,4-tetrahydroisoquinolin-6-ylmethyl)-1H-pyrazol-4-yl]butyl}-3H-[1,2,3]triazolo[4,5-b]pyridin-5-amine, 2TFA

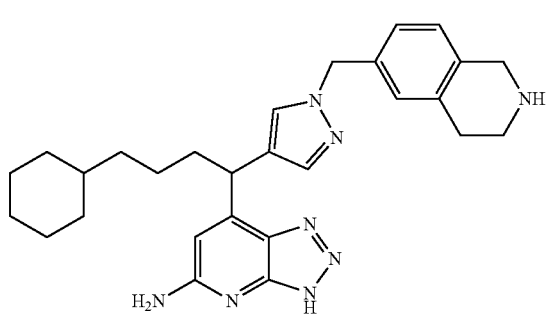 [SMILES: Nc1cc(C(CCCC2CCCCC2)c2cnn(Cc3ccc4c(c3)CCNC4)c2)c2nn[nH]c2n1]

Prepared with 3-bromopropyl)cyclohexane. MS (ESI): m/z 485.4 (M+H). $^1$H NMR (500 MHz, DMSO-$d_6$) δ 7.68 (s, 1H), 7.40 (s, 1H), 6.84-7.07 (m, 4H), 6.50 (br. s., 2H), 6.36 (s, 1H), 5.17 (s, 2H), 4.25 (s, 1H), 3.86 (m, 2H), 2.93-3.02 (m, 2H), 2.60-2.70 (m, 2H), 2.09-2.23 (m, 1H), 1.94-2.07 (m, 1H), 1.50-1.73 (m, 8H), 1.32-1.48 (m, 4H), 0.68-0.84 (m, 2H). HPLC retention time: 1.48 min (Method C).

Example 7. 7-[4-(naphthalen-2-yl)-1-[1-(1,2,3,4-tetrahydroisoquinolin-6-ylmethyl)-1H-pyrazol-4-yl]butyl]-3H-[1,2,3]triazolo[4,5-b]pyridin-5-amine, 2TFA

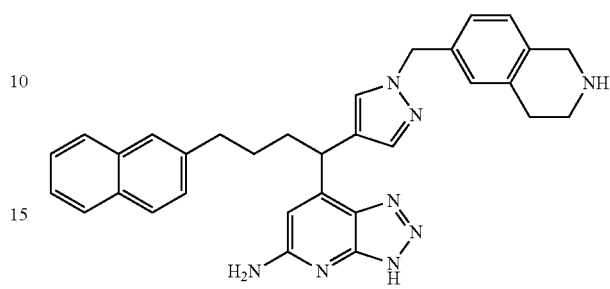

Prepared with 2-(3-bromopropyl)naphthalene. MS (ESI): m/z 529.3 (M+H). $^1$H NMR (500 MHz, DMSO-$d_6$) δ 8.95 (br. s., 2H), 7.97 (s, 1H), 7.77-7.89 (m, 3H), 7.57-7.73 (m, 2H), 7.39-7.51 (m, 3H), 7.27-7.35 (m, J=8.30 Hz, 1H), 7.14 (br. s., 1H), 7.06-7.09 (m, 1H), 6.34-6.48 (m, 1H), 5.21 (s, 2H), 4.35 (br. s., 1H), 4.22 (br. s., 2H), 3.33 (br. s., 2H), 2.85-2.90 (m, 2H), 2.79 (t, J=7.15 Hz, 2H), 1.98-2.34 (m, 2H), 1.54-1.75 (m, J=7.20 Hz, 2H), 1.33-1.50 (m, 1H), 1.21-1.30 (m, 1H). HPLC retention time: 1.30 min (Method C).

Example 8. 7-[4-(2,3-dihydro-1H-inden-1-yl)-1-[1-(1,2,3,4-tetrahydroisoquinolin-6-ylmethyl)-1H-pyrazol-4-yl]butyl]-3H-[1,2,3]triazolo[4,5-b]pyridin-5-amine, 2TFA

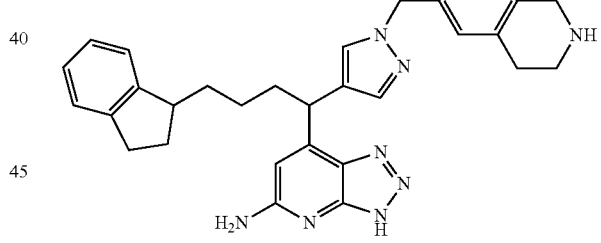

8A. 1-(3-bromopropyl)-2,3-dihydro-1H-indene

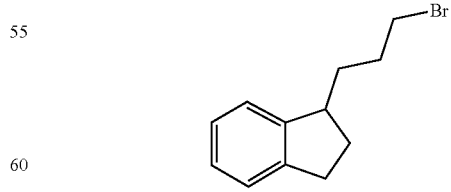

1H-indene (0.5 g, 4.3 mmol) was dissolved in 50% aq. NaOH (10 mL)/40% Methanolic Triton B (1 mL) at 0° C. 1,3-Dibromopropane (0.46 mL, 4.3 mmol) was added, and the reaction mixture was allowed to warm to rt and was stirred overnight. The reaction mixture was diluted with EtOAc and water. The aq. phase was extracted 3× with EtOAc. The combined organic phases were washed with brine, dried with Na₂SO₄, filtered and concentrated. The product was purified by silica gel chromatography to provide 3-(3-bromopropyl)-1H-indene as a yellow oil (47 mg, 4.6%). ¹H NMR (500 MHz, CDCl₃) δ 7.45-7.49 (m, 1H), 7.36-7.40 (m, 1H), 7.28-7.34 (m, 3H), 7.18-7.24 (m, 1H), 6.23-6.30 (m, 1H), 3.46-3.54 (m, 2H), 3.32-3.37 (m, 2H), 2.67-2.79 (m, 2H), 2.16-2.32 (m, 2H). The indene product (43 mg, 0.18 mmol) was dissolved in MeOH (10 mL). 10% Pd—C (5.0 mg, 0.047 mmol) was added, and reaction flask was evacuated and backfilled with nitrogen, then stirred overnight under a H₂ balloon at rt. The catalyst was removed by filtration and washed with MeOH. Filtrate was evaporated to provide indane 8A as a clear oil (40 mg, 92%). ¹H NMR (500 MHz, CDCl₃) δ 7.16 (d, J=3.30 Hz, 4H), 3.40-3.51 (m, 1H), 3.09-3.18 (m, 1H), 2.89-2.98 (m, 1H), 2.76-2.88 (m, 1H), 2.12-2.35 (m, 1H), 1.92-2.07 (m, 2H), 1.63-1.74 (m, 1H), 1.53-1.62 (m, 1H), 1.19-1.32 (m, 1H).

Example 8. The title compound was prepared using the procedures described for Ex. 1 substituting 8A for the 3-phenylpropyl bromide in step 1B. MS (ESI): m/z 519.4 (M+H) ¹H NMR (500 MHz, DMSO-d₆) δ 9.03 (br. s., 2H), 7.74 (s, 1H), 7.45 (s, 1H), 7.18 (br. s., 2H), 7.06-7.13 (m, 5H), 6.39-6.49 (m, 1H), 5.23 (br. s., 2H), 4.28-4.36 (m, 1H), 4.24 (br. s., 2H), 2.93 (br. s., 3H), 2.76-2.86 (m, 1H), 2.63-2.74 (m, 1H), 1.97-2.42 (m, 4H), 1.71-1.92 (m, 1H), 1.36 (br. s., 4H). HPLC retention time: 1.43 min (Method C).

Example 9. 7-[4-(Naphthalen-1-yl)-1-[1-(1,2,3,4-tetrahydroisoquinolin-6-ylmethyl)-1H-pyrazol-4-yl]butyl]-3H-[1,2,3]triazolo[4,5-b]pyridin-5-amine, 2TFA

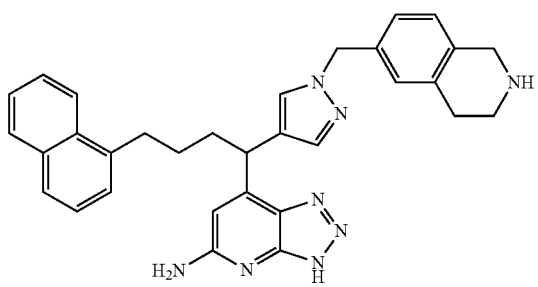 [SMILES: Nc1cc(C(CCCc2cccc3ccccc23)c2cnn(Cc3ccc4c(c3)CCNC4)c2)c2nn[nH]c2n1]

Prepared with 1-(3-bromopropyl)naphthalene. MS (ESI): m/z 530.7 (M+H). ¹H NMR (500 MHz, DMSO-d₆) δ 7.16-7.24 (m, 1H), 7.00-7.13 (m, 2H), 6.87-6.94 (m, 1H), 6.81-6.84 (m, 1H), 6.68-6.71 (m, 1H), 6.43-6.66 (m, 5H), 6.21-6.33 (m, 2H), 6.11-6.16 (m, 1H), 5.67-5.76 (m, 1H), 4.43 (s, 2H), 3.64-3.74 (m, 1H), 3.39 (s, 2H), 2.28-2.38 (m, 2H), 2.21 (s, 2H), 2.04-2.10 (m, 2H), 1.38-1.69 (m, 2H), 0.90-1.02 (m, 2H). HPLC retention time: 1.38 min (Method C).

Example 10. 7-[3-(Oxan-4-yl)-1-[1-(1,2,3,4-tetrahydroisoquinolin-6-ylmethyl)-1H-pyrazol-4-yl]propyl]-3H-[1,2,3]triazolo[4,5-b]pyridin-5-amine, 2TFA

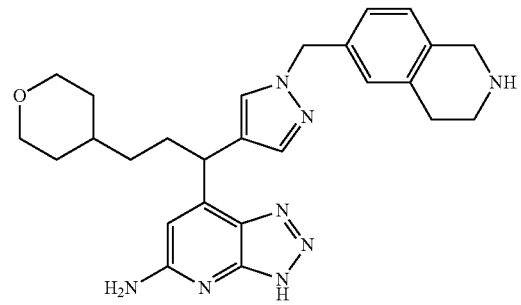 [SMILES: Nc1cc(C(CCC2CCOCC2)c2cnn(Cc3ccc4c(c3)CCNC4)c2)c2nn[nH]c2n1]

Prepared with 4-(2-bromoethyl)tetrahydro-2H-pyran. MS (ESI): m/z 473.3 (M+H). ¹H NMR (500 MHz, DMSO-d₆) δ 7.69 (s, 1H), 7.41 (s, 1H), 6.96 (s, 2H), 6.91 (s, 1H), 6.54 (s, 2H), 6.35 (s, 1H), 5.17 (s, 2H), 4.22 (t, J=7.6 Hz, 1H), 3.81-3.75 (m, 3H), 3.23 (t, J=11.4 Hz, 2H), 2.95 (t, J=5.6 Hz, 2H), 2.64 (t, J=5.5 Hz, 2H), 2.27-2.17 (m, 1H), 2.11-2.00 (m, 1H), 1.59-1.41 (m, 3H), 1.28-1.15 (m, 1H), 1.15-0.99 (m, 3H)-one of the methylenes of the tetrahydropyran ring is obscured by the solvent water peak. HPLC retention time: 0.95 min (Method C).

Example 11: 7-{3-Phenoxy-1-[1-(1,2,3,4-tetrahydroisoquinolin-6-ylmethyl)-1H-pyrazol-4-yl]propyl}-3H-[1,2,3]triazolo[4,5-b]pyridin-5-amine, 2TFA

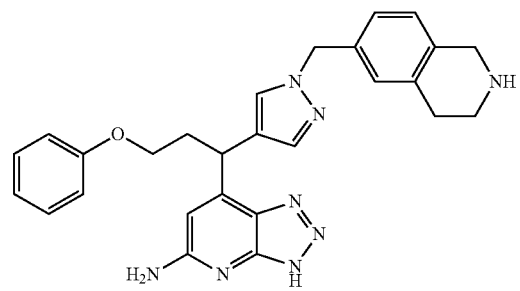 [SMILES: Nc1cc(C(CCOc2ccccc2)c2cnn(Cc3ccc4c(c3)CCNC4)c2)c2nn[nH]c2n1]

Prepared with (2-bromoethoxy)benzene. MS (ESI): m/z 481.3 (M+H). ¹H NMR (500 MHz, CD₃OD) δ 7.75 (s, 1H), 7.56 (s, 1H), 7.17-7.26 (m, 2H), 7.11-7.15 (m, 1H), 7.05-7.09 (m, 1H), 7.02 (s, 1H), 6.84-6.92 (m, 1H), 6.72-6.81 (m, 3H), 5.26 (s, 2H), 4.64-4.74 (m, 1H), 4.30 (s, 2H), 3.91-4.05 (m, 2H), 3.39-3.52 (m, J=6.30, 6.30 Hz, 2H), 2.97-3.06 (m, 2H), 2.73-2.83 (m, 1H), 2.51-2.67 (m, 1H). HPLC Retention time: 1.06 min (Method C).

Example 12. 7-{4-Phenyl-1-[1-(pyridin-3-ylmethyl)-1H-pyrazol-4-yl]butyl}-3H-[1,2,3]triazolo[4,5-b]pyridin-5-amine, 2 TFA

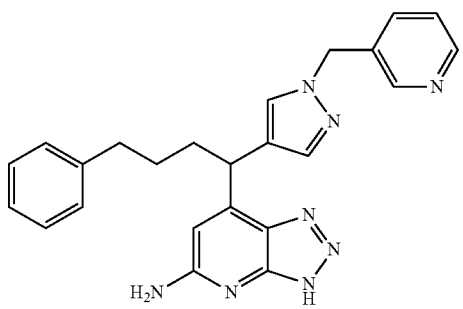 [SMILES: Nc1cc(C(CCCc2ccccc2)c2cnn(Cc3cccnc3)c2)c2nn[nH]c2n1]

Example 12 was prepared from Intermediate 3 as described for Ex. 1 substituting pyridin-3ylmethanol for 1A in step 1B. MS (ESI): m/z 424.9 (M+H). $^1$H NMR (500 MHz, CD$_3$OD) δ 8.69 (d, J=4.95 Hz, 1H), 8.60 (s, 1H), 8.09-8.18 (m, J=8.00 Hz, 1H), 7.77-7.85 (m, 2H), 7.57 (s, 1H), 7.20-7.31 (m, 2H), 7.08-7.19 (m, 3H), 6.78 (s, 1H), 5.50 (s, 2H), 4.47 (t, J=7.70 Hz, 1H), 2.68 (t, J=7.29 Hz, 2H), 2.26-2.40 (m, 1H), 2.13-2.25 (m, 1H), 1.53-1.81 (m, J=5.80 Hz, 2H). HPLC retention time: 4.46 min (Method C).

Example 13. 7-[4-Phenyl-1-(1-{[3-(piperidin-4-yl)phenyl]methyl}-1H-pyrazol-4-yl)butyl]-3H-[1,2,3]triazolo[4,5-b]pyridin-5-amine, 2 TFA

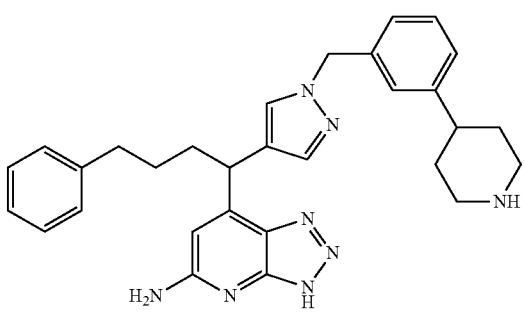 [SMILES: Nc1cc(C(CCCc2ccccc2)c2cnn(Cc3cccc(C4CCNCC4)c3)c2)c2nn[nH]c2n1]

13A. tert-Butyl 4-(3-(Hydroxymethyl)phenyl)piperidine-1-carboxylate

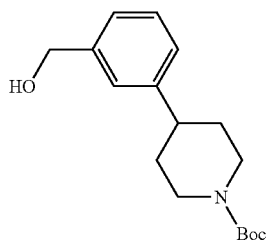

A solution of 3-(piperidin-4-yl)benzoic acid (480 mg, 2.34 mmol) and H$_2$SO$_4$ (0.10 mL, 1.9 mmol) in MeOH (10 mL) was stirred at reflux for 72 h. After evaporation of the solvent, the residue was taken up in 1N NaOH and extracted 3× with ethyl acetate. The combined extracts were dried over Na$_2$SO$_4$, filtered and evaporated to give methyl 3-(piperidin-4-yl)benzoate (0.47 g, 91%) as a colorless oil. MS (ESI): m/z 219.9 (M+H). The oil was redissolved in THF (5 mL) and treated with DIEA (0.930 mL, 5.32 mmol) and Boc anhydride (535 mg, 2.45 mmol). The reaction mixture was stirred at rt overnight.

The reaction mixture was washed with brine and dried over Na$_2$SO$_4$. The solvent was removed, and the residue purified by silica gel chromatography to provide tert-butyl 4-(3-(methoxycarbonyl)phenyl)piperidine-1-carboxylate (0.60 g, 88%) as a colorless oil. MS (ESI): m/z 319.9 (M+H) 263.9 (M+H-tBu). The ester (533 mg, 1.67 mmol) was then dissolved in THF (8.3 mL) and treated dropwise with 2M LiBH$_4$ in THF (1.67 mL, 3.34 mmol) at 0° C. under inert atmosphere. The resulting pale yellow solution was stirred for ~1 h at 0° C. then overnight at rt. Another 2M LiBH$_4$ in THF (1 mL, 1 mmol) was added, followed by stirring at rt for 1 h then reflux for 2.5 h. The reaction mixture was cooled to 0° C. and quenched with 1M HCl to pH 1. After stirring for 30 min, the pH was adjusted with solid K$_2$CO$_3$ to 9-10, and the mixture was extracted 2× with EtOAc. The combined extracts were washed with brine, dried over Na$_2$SO$_4$, filtered and evaporated to give the title alcohol 13A (509 mg, 105%) as a colorless oil, after separation from unreacted ester by flash chromatography. MS (ESI): m/z 236.0 (M+H-tBu).

Example 13. Example 13 was prepared from Intermediate 3 as described for Ex. 1 substituting alcohol 13A for 1A in step 1B. MS (ESI): m/z 506.9 (M+H). $^1$H NMR (500 MHz, DMSO-d$_6$) δ 7.72 (s, 1H), 7.41 (s, 1H), 7.27-7.21 (m, 4H), 7.12 (d, J=7.2 Hz, 3H), 7.00 (d, J=7.4 Hz, 1H), 6.97 (br. s., 1H), 6.51 (br. s., 2H), 6.37 (s, 1H), 5.24 (s, 2H), 4.31 (t, J=7.6 Hz, 1H), 3.10 (d, J=11.0 Hz, 2H), 2.66 (t, J=11.8 Hz, 2H), 2.63-2.55 (m, 3H), 2.19 (d, J=6.9 Hz, 1H), 2.08 (d, J=8.3 Hz, 1H), 1.66 (d, J=12.7 Hz, 2H), 1.55-1.44 (m, 4H). HPLC retention time: 1.27 min (Method C).

Example 14. 7-[1-(1-Benzyl-1H-pyrazol-4-yl)-4-(1,2,3,4-tetrahydroisoquinolin-1-yl)butyl]-3H-[1,2,3]triazolo[4,5-b]pyridin-5-amine, 2TFA

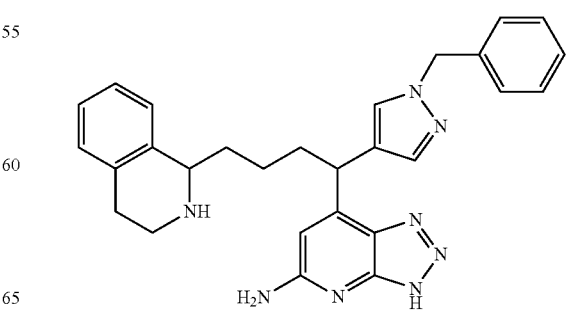

14A. tert-Butyl 1-(3-bromopropyl)-3,4-dihydroiso-quinoline-2(1H)-carboxylate

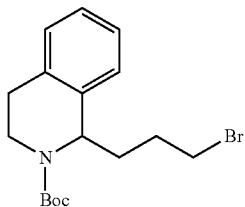 [SMILES: CC(C)(C)OC(=O)N1CCc2ccccc2C1CCCBr]

A mixture of 1,2,3,4-tetrahydroisoquinoline (0.472 mL, 3.75 mmol), Boc₂O (0.872 mL, 3.75 mmol) and TEA (0.576 mL, 4.13 mmol) in THF (20 mL) was stirred overnight at rt. The reaction mixture was concentrated, and the product was purified by silica gel chromatography to provide tert-butyl 3,4-dihydroisoquinoline-2(1H)-carboxylate (519 mg, 59.3%), as a clear oil. MS (ESI): m/z 234.0 (M+H). The Boc-protected intermediate (300 mg, 1.29 mmol) was dissolved in anhydrous THF (5 mL) under Ar at −78° C. A solution of nBuLi (1.6M in hexanes, 0.723 mL, 1.16 mmol) was added dropwise, and the reaction mixture was stirred at −78° C. for 0.5 hours. A solution of 1,3-dibromopropane (519 mg, 2.57 mmol) in anhydrous THF (1 mL) was then added at once, and the reaction mixture was stirred for an additional 1 h at −78° C., then quenched with saturated aq. ammonium chloride and extracted 3× with EtOAc. The combined organics were washed with brine, dried with Na₂SO₄, filtered and concentrated. Purification by silica gel chromatography provided 14A (180 mg, 39.5%), as a clear oil. MS (ESI): m/z 355.8 (M+H).

Example 14. Example 14 was prepared from Intermediate 3 as described for Ex. 1 substituting benzyl alcohol for 1A in step 1B and 14A for (3-bromopropyl)benzene in step 1C. MS (ESI): m/z 479.4 (M+H). ¹H NMR (500 MHz, CD₃OD) δ 7.66-7.69 (m, 1H), 7.56 (s, 1H), 7.13-7.44 (m, 9H), 6.51 (s, 1H), 5.30 (s, 2H), 4.53-4.66 (m, 1H), 4.47-4.54 (m, 1H), 4.39-4.46 (m, 1H), 3.42-3.57 (m, 1H), 3.26-3.33 (m, 1H), 3.04-3.19 (m, 2H), 2.36-2.48 (m, 1H), 2.15-2.33 (m, 2H), 1.89-2.09 (m, 1H), 1.38-1.69 (m, 2H). HPLC retention time: 1.08 min (Method C).

Example 15. 7-[3-(Benzylamino)-1-(1-methyl-1H-pyrazol-4-yl)propyl]-3H-[1,2,3]triazolo[4,5-b]pyridin-5-amine, 2 TFA

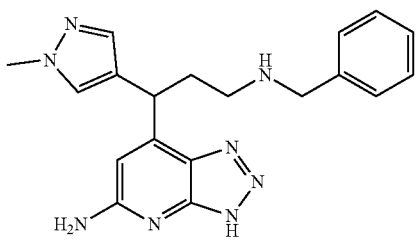 [SMILES: Cn1cc(C(CCNCc2ccccc2)c2cc(N)nc3[nH]nnc23)cn1]

15A. tert-Butyl benzyl(2-oxoethyl)carbamate

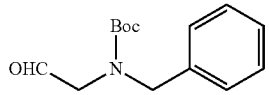 [SMILES: CC(C)(C)OC(=O)N(CC=O)Cc1ccccc1]

Boc₂O (7.68 mL, 33.1 mmol) was added to a cooled solution of 2-(benzylamino)ethanol (5.00 g, 33.1 mmol) in DCM (132 mL), and the reaction mixture was warmed to rt and stirred for 1 h. Dess-Martin Periodinane (DMP) (14.0 g, 33.1 mmol) was added to the reaction mixture and stirring at rt was continued for an additional 30 min. The reaction mixture was quenched with a 1:1 mixture of sat. aq. NaHCO₃: 10% aqueous sodium thiosulfate. The mixture was concentrated, and product isolated by silica gel chromatography to provide 15A as a clear, colorless oil. (7.10 g, 86%). ¹H NMR (500 MHz, CDCl₃) δ 9.64-9.35 (m, 1H), 7.52-7.13 (m, 5H), 4.66-4.43 (m, 2H), 4.05-3.70 (m, 2H), 1.51 (br d, J=13.2 Hz, 9H).

15B. tert-Butyl benzyl(3,3-dibromoallyl)carbamate

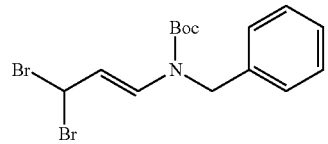 [SMILES: CC(C)(C)OC(=O)N(/C=C/C(Br)Br)Cc1ccccc1]

CBr₄ (1.33 g, 4.01 mmol) was added to a solution of 15A (1.00 g, 4.01 mmol) and triphenylphosphine (1.05 g, 4.01 mmol) at 0° C., and the reaction mixture was stirred overnight, warming to rt. The reaction mixture was concentrated and product was purified by silica gel chromatography to provide 15B as a clear, colorless oil (1.20 g, 73.8%). ¹H NMR (400 MHz, CDCl₃) δ 7.46-7.09 (m, 5H), 6.59-6.22 (m, 1H), 4.44 (br s, 2H), 4.05-3.54 (m, 1H), 4.05-3.54 (m, 1H), 1.56-1.41 (m, 9H).

15C. (E)-tert-Butyl benzyl(3-bromo-3-(3-trityl-5-(tritylamino)-3H-[1,2,3]triazolo[4,5-b]pyridin-7-yl)allyl)carbamate

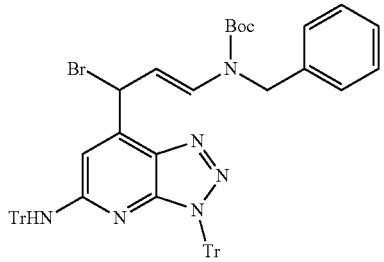

A mixture of Intermediate 1 (200 mg, 0.29 mmol), 5,5,5',5'-tetramethyl-2,2'-bi(1,3,2-dioxaborinane) (71.1 mg, 0.315 mmol), KOAc (42.1 mg, 0.429 mmol), Pd₂(dba)₃ (13.1 mg, 0.014 mmol), and tricyclohexylphosphonium tetrafluoroborate (10 mg, 0.029 mmol) were added to a pressure-rated vial that was evacuated and back-filled with argon 3×. Thoroughly degassed dioxane (954 μL) was added to the vial, and the reaction mixture was stirred at 100° C. for 2 hours. The mixture was cooled to rt, and (Ph₃P)₄Pd (33 mg, 0.029 mmol) was added, followed by a solution of K₂CO₃ (118 mg, 0.857 mmol) in degassed water (714 μL). A solution of 15B (116 mg, 0.286 mmol) in degassed THF (714 μL) was then added, and the reaction mixture was heated to 80° C. for 2 h. The product was the purified by silica gel chromatography to provide 15C. (160 mg, 56.4%). MS (ESI): m/z 943.3 (M+H).

15D. (E)-tert-Butyl benzyl(3-(1-methyl-1H-pyrazol-4-yl)-3-(3-trityl-5-(tritylamino)-3H-[1,2,3]triazolo[4,5-b]pyridin-7-yl)allyl)carbamate

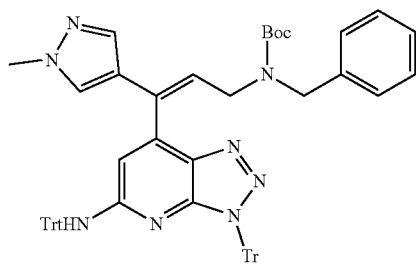

To a mixture of 15C (80 mg, 0.085 mmol), 1-methyl-4-(4,4,5,5-tetramethyl-1,3,2-dioxaborolan-2-yl)-1H-pyrazole (26.4 mg, 0.127 mmol), Cs₂CO₃ (83.0 mg, 0.254 mmol) and PdCl₂(dppf)-CH₂Cl₂ adduct (6.92 mg, 8.47 μmol) was added degassed dioxane (1.5 mL). The above rxn mix was then degassed 3× and heated to 90° C. for 2 h. The crude product 15D was used in the next step without purification. MS (ESI): m/z 945.0 (M+H).

Example 15. TFA (1 mL) was added to a solution of 15D (80 mg, 0.085 mmol) in DCM (4 mL). After 10 minutes, triethylsilane (0.014 mL, 0.085 mmol) was added. An additional aliquot of TFA (2 mL) was added and stirring was continued for an additional 1 h at rt. The reaction mixture was concentrated and residue taken up in ethanol (15 mL). 10% Pd/C (8.86 mg, 8.32 μmol) was added, and the mixture was degassed then stirred under 20 psi of hydrogen overnight. The reaction mixture was filtered through Celite,® and the filtrate was evaporated. The crude product was purified by RP-HPLC to provide the title compound. MS (ESI): m/z 363.2 (M+H). ¹H NMR (500 MHz, DMSO-d₆) δ 7.53 (s, 1H), 7.33 (s, 1H), 7.25 (d, J=4.4 Hz, 4H), 7.18 (dq, J=8.5, 4.2 Hz, 1H), 6.48 (s, 2H), 6.34 (s, 1H), 4.48-4.35 (m, 1H), 3.74 (s, 3H), 3.63 (s, 2H), 2.46-2.39 (m, 2H), 2.33 (td, J=13.5, 7.4 Hz, 1H), 2.26-2.12 (m, 1H). HPLC retention time: 0.89 min (Method C).

Example 16. 7-[1-(1-Benzyl-1H-pyrazol-4-yl)-3-[(4-phenylcyclohexyl)amino]propyl]-3H-[1,2,3]triazolo[4,5-b]pyridin-5-amine, 2TFA

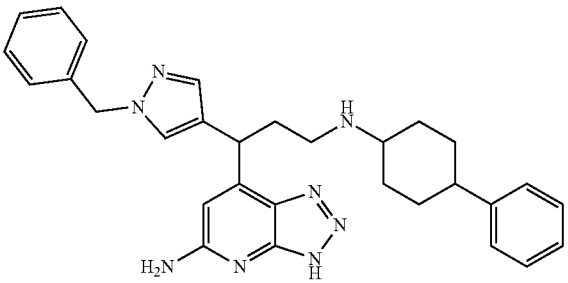 [SMILES: Nc1cc(C(CCNC2CCC(c3ccccc3)CC2)c2cnn(Cc3ccccc3)c2)c2nn[nH]c2n1]

16A. (E)-3-(1-Benzyl-1H-pyrazol-4-yl)-3-(3-trityl-5-(tritylamino)-3H-[1,2,3]triazolo[4,5-b]pyridin-7-yl)prop-2-en-1-ol

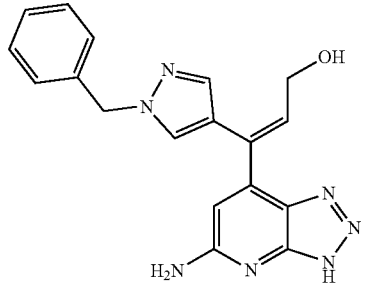 [SMILES: Nc1cc(/C(=C/CO)c2cnn(Cc3ccccc3)c2)c2nn[nH]c2n1]

A mixture of Intermediate 2 (127 mg, 0.158 mmol), 1-benzyl-4-(4,4,5,5-tetramethyl-1,3,2-dioxaborolan-2-yl)-1H-pyrazole (54.0 mg, 0.190 mmol), K₂CO₃ (109 mg, 0.792 mmol) and PdCl₂(dppf)-CH₂Cl₂ adduct (12.9 mg, 0.016 mmol) was dissolved in 1:1 THF/water in a pressure-rated vial. The vial was evacuated and backfilled 3× with Ar, then heated behind a blast shield at 80° C. for 2 hours. The reaction mixture was diluted with water and EtOAc. The aq. phase was extracted 3× with EtOAc. The combined organic phases were washed with brine, dried with Na₂SO₄, filtered and concentrated. The product was the purified by silica gel chromatography to provide 16A. (97 mg, 74%), as a yellow oil. MS (ESI): m/z 832.5 (M+H).

16B. (E)-3-(1-Benzyl-1H-pyrazol-4-yl)-3-(3-trityl-5-(tritylamino)-3H-[1,2,3]triazolo[4,5-b]pyridin-7-yl)acrylaldehyde

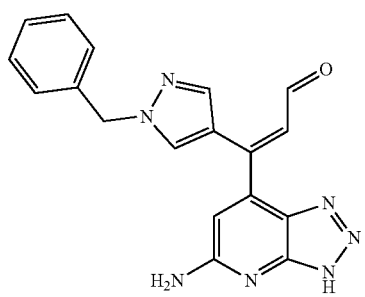 [SMILES: Nc1cc(/C(=C/C=O)c2cnn(Cc3ccccc3)c2)c2nn[nH]c2n1]

16A (97 mg, 0.12 mmol) was dissolved in CHCl₃ (5 mL). MnO₂ (81 mg, 0.93 mmol) was added, and reaction mixture stirred at rt under Ar overnight. The reaction mixture was filtered through Celite®. The filtrate was concentrated to yield aldehyde 16B as a yellow solid which was taken forward to the next step without further purification. MS (ESI): m/z 830.4 (M+H).

16C. (E)-7-(1-(1-benzyl-1H-pyrazol-4-yl)-3-((4-phenylcyclohexyl)amino)prop-1-en-1-yl)-N,3-ditrityl-3H-[1,2,3]triazolo[4,5-b]pyridin-5-amine

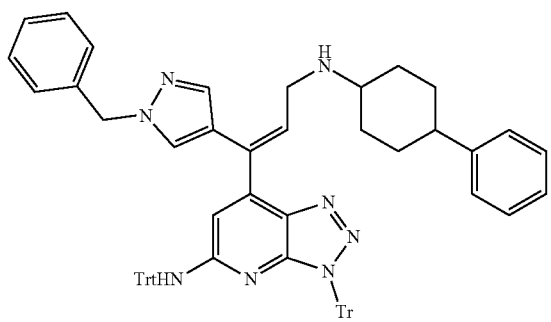

To a solution of 16B (97 mg, 0.12 mmol) and TEA (0.098 mL, 0.70 mmol) in EtOH (5 mL) was added 4-phenylcyclohexanamine (62 mg, 0.35 mmol). The mixture was heated to 60° C. for 2 hours, then allowed to cool to rt. THF (5 mL) and NaBH₄ (24.3 mg, 0.643 mmol) were added, and the reaction mixture was stirred at rt under Ar for 1 h. The reaction mixture was diluted with 1M NaOH and EtOAc. The aq. phase was extracted 2× with EtOAc. The combined organics were washed with brine, dried with Na₂SO₄, filtered and concentrated to yield 16C as a yellow oil which was taken on to the next step. MS (ESI) m/z 989.6 (M+H).

Example 16. TFA (10 mL) was added to a solution of 16C (116 mg, 0.117 mmol) in DCM (10 mL). Triethylsilane (0.094 mL, 0.59 mmol) was added, and the reaction mixture was stirred at rt under Ar, then concentrated. The residue was dissolved in a 10:1 mixture of EtOH/EtOAc (5.5 mL). Pt₂O (5.3 mg, 0.023 mmol) was added, and the reaction mixture was evacuated and backfilled with N₂ 3×, then stirred at rt under 1 atm of H₂ overnight. Catalyst was removed by filtration, and the filtrate was evaporated. Purification by prep RP-HPLC provided Example 16 (1.1 mg, 1.8%). MS (ESI): m/z 507.3 (M+H). ¹H NMR (500 MHz, CD₄OD) δ 7.75 (s, 1H), 7.61 (s, 1H), 7.16-7.38 (m, 10H), 6.49 (s, 1H), 5.30-5.33 (m, 2H), 4.50-4.57 (m, 1H), 3.08-3.15 (m, 1H), 3.02 (s, 2H), 2.65-2.82 (m, 1H), 2.46-2.61 (m, 1H), 1.96-2.19 (m, 2H), 1.76-1.93 (m, 5H), 1.41-1.66 (m, 2H). HPLC retention time: 1.42 min (Method C).

Example 17. 7-[1-(1-Benzyl-1H-pyrazol-4-yl)-3-[(2,3-dihydro-1H-inden-1-yl)amino]propyl]-3H-[1,2,3]triazolo[4,5-b]pyridin-5-amine, 2TFA

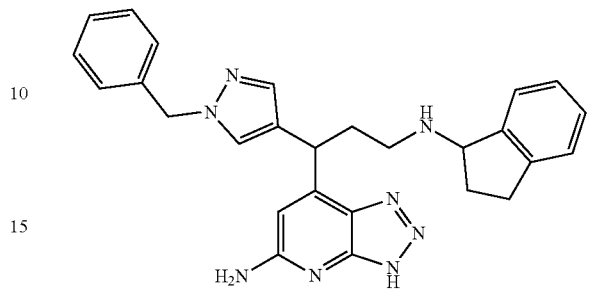

Example 17 was prepared from 16B as described for Ex. 16 substituting 2,3-dihydro-1H-inden-1-amine for 4-phenylcyclohexanamine in step 16C. MS (ESI): m/z 465.3 (M+H). ¹H NMR (500 MHz, DMSO-d₆) δ 7.68-7.77 (m, J=8.80 Hz, 1H), 7.41-7.47 (m, J=8.80 Hz, 1H), 7.07-7.36 (m, 10H), 6.52 (br. s., 2H), 6.38-6.42 (m, J=2.50 Hz, 1H), 5.24-5.28 (m, 2H), 4.47 (d, J=7.70 Hz, 1H), 4.07 (s, 1H), 2.81-2.90 (m, 1H), 2.62-2.73 (m, 2H), 2.55 (d, J=6.88 Hz, 1H), 2.13-2.45 (m, 3H), 1.56-1.68 (m, 1H). HPLC retention time: 1.19 min (Method C).

Example 18. 7-[1-(1-Benzyl-1H-pyrazol-4-yl)-3-{[(1r,4r)-4-phenylcyclohexyl]-amino}propyl]-3H-[1,2,3]triazolo 4,5-b pyridin-5-amine, 2TFA

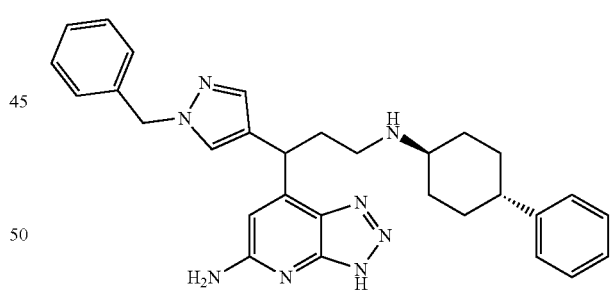

Example 18 was prepared from 16B as described for Ex. 16 substituting trans-4-phenylcyclohexanamine, HCl for 4-phenylcyclohexanamine in step 16C. MS (ESI): m/z 507.1 (M+H). ¹H NMR (500 MHz, CD₃OD) δ 7.79 (s, 1H), 7.65 (s, 1H), 7.27-7.38 (m, 1H), 7.16-7.26 (m, 1H), 6.69 (s, 1H), 5.33 (s, 2H), 4.52-4.61 (m, 1H), 3.13-3.22 (m, 1H), 3.05-3.12 (m, J=8.10, 8.10 Hz, 2H), 2.67-2.79 (m, 1H), 2.50-2.62 (m, 2H), 2.12-2.22 (m, 2H), 1.95-2.04 (m, 2H), 1.42-1.69 (m, 4H). HPLC retention time: 5.59 min (Method A).

Example 19. 7-(1-{1-[(4-Chlorophenyl)methyl]-1H-pyrazol-4-yl}-3-{[trans-4-phenylcyclohexyl]amino}propyl)-3H-[1,2,3]triazolo[4,5-b]pyridin-5-amine, 2TFA

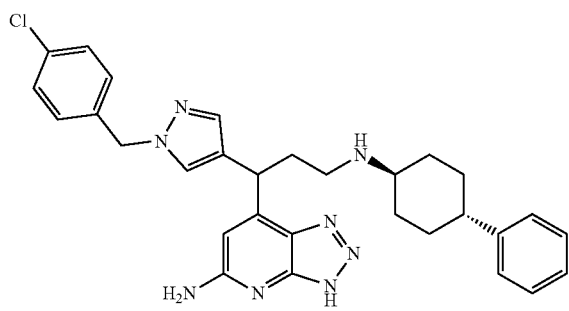 [SMILES: Nc1cc(C(CCN[C@H]2CC[C@H](c3ccccc3)CC2)c2cnn(Cc3ccc(Cl)cc3)c2)c2nn[nH]c2n1]

19A. 1-(4-Chlorobenzyl)-4-(4,4,5,5-tetramethyl-1,3,2-dioxaborolan-2-yl)-1H-pyrazole

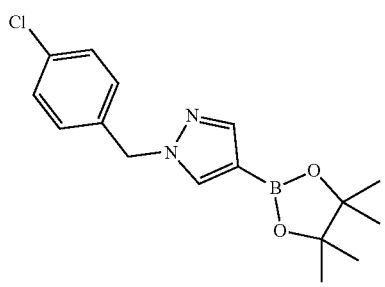 [SMILES: CC1(C)OB(c2cnn(Cc3ccc(Cl)cc3)c2)OC1(C)C]

4-(4,4,5,5-Tetramethyl-1,3,2-dioxaborolan-2-yl)-1H-pyrazole (400 mg, 2.06 mmol) and (4-chlorophenyl)methanol (294 mg, 2.06 mmol) were dissolved in toluene (10 mL). Tris(butyl)phosphine (0.772 mL, 3.09 mmol) was added, followed by TMAD (532 mg, 3.09 mmol), and the reaction mixture was stirred at rt overnight under Ar. The reaction mixture was filtered, and the solids were washed with toluene. The filtrate was evaporated, and the product was purified by silica gel chromatography to provide pyrazole boronate 19A (300 mg, 45.7%), as a clear oil. MS (ESI): m/z 318.7 (M+H).

Example 19 was prepared from 19A and Intermediate 2 using the procedures described for the preparation of Ex. 16 substituting 19A for 1-benzyl-4-(4,4,5,5-tetramethyl-1,3,2-dioxaborolan-2-yl)-1H-pyrazole in step 16A. MS (ESI): m/z 541.3 (M+H). $^1$H NMR (500 MHz, CD$_3$OD) δ 7.79 (s, 1H), 7.64 (s, 1H), 7.35 (d, J=8.25 Hz, 2H), 7.13-7.31 (m, 7H), 6.60-6.61 (m, 1H), 6.53-6.65 (m, 1H), 5.31 (s, 2H), 4.51-4.58 (m, 1H), 3.13-3.22 (m, 1H), 3.04-3.12 (m, 2H), 2.69-2.76 (m, 1H), 2.46-2.62 (m, 2H), 2.11-2.22 (m, 2H), 1.96-2.04 (m, 2H), 1.40-1.67 (m, 4H). HPLC retention time: 1.44 min (Method C).

Example 20. 7-[1-(1-Cyclobutyl-1H-pyrazol-4-yl)-3-{[(1r,4r)-4-phenylcyclohexyl]amino}propyl]-3H-[1,2,3]triazolo[4,5-b]pyridin-5-amine, 2TFA

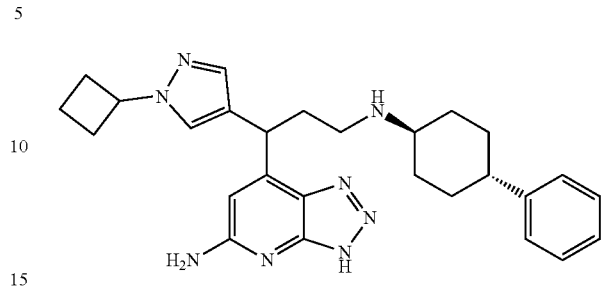

20A. 1-Cyclobutyl-4-(4,4,5,5-tetramethyl-1,3,2-dioxaborolan-2-yl)-1H-pyrazole

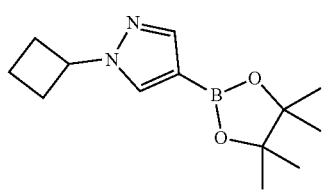 [SMILES: CC1(C)OB(c2cnn(C3CCC3)c2)OC1(C)C]

4-(4,4,5,5-Tetramethyl-1,3,2-dioxaborolan-2-yl)-1H-pyrazole (300 mg, 1.55 mmol) was dissolved in DMF (5 mL) at 0° C. under Ar. NaH (60% in oil, 40.8 mg, 1.70 mmol) was added portionwise, and the reaction mixture was then stirred for 20 minutes at rt. A solution of bromocyclobutane (209 mg, 1.55 mmol) in 1 mL of DMF was added, and stirring was continued 2 h at rt. The reaction mixture was quenched with saturated aq. NH$_4$Cl, and then extracted 3× with EtOAc, washed with brine, dried with Na$_2$SO$_4$, filtered and concentrated. The product was purified by silica gel chromatography to provide pyrazole boronate 20A (40 mg, 5.21%). MS (ESI): m/z 249.0 (M+H).

Example 20 was prepared from 20A and Intermediate 2 using the procedures described for the preparation of Ex. 16 substituting 20A for 1-benzyl-4-(4,4,5,5-tetramethyl-1,3,2-dioxaborolan-2-yl)-1H-pyrazole in step 16A.

Example 21. 7-{1-[1-(Cyclobutylmethyl)-1H-pyrazol-4-yl]-3-{[(1r,4r)-4-phenylcyclohexyl]amino}propyl}-3H-[1,2,3]triazolo[4,5-b]pyridin-5-amine, 2TFA

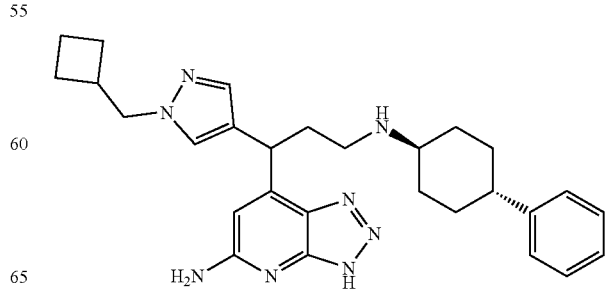

21A. 1-(Cyclobutylmethyl)-4-(4,4,5,5-tetramethyl-1,3,2-dioxaborolan-2-yl)-1H-pyrazole

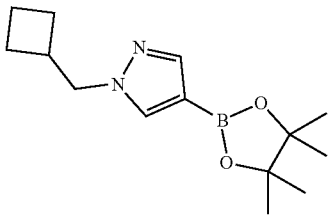 [SMILES: CC1(C)OB(c2cnn(CC3CCC3)c2)OC1(C)C]

21A was prepared in 65% by Mitsunobu condensation of cyclobutylmethanol with 4-(4,4,5,5-tetramethyl-1,3,2-dioxaborolan-2-yl)-1H-pyrazole using the procedure described above for the synthesis of 19A. MS (ESI): m/z 262.9 (M+H).

21B. 7-((Z)-1-(1-(cyclobutylmethyl)-1H-pyrazol-4-yl)-3-(((1r,4r)-4-phenylcyclohexyl)amino)prop-1-en-1-yl)-N,3-ditrityl-3H-[1,2,3]triazolo[4,5-b]pyridin-5-amine

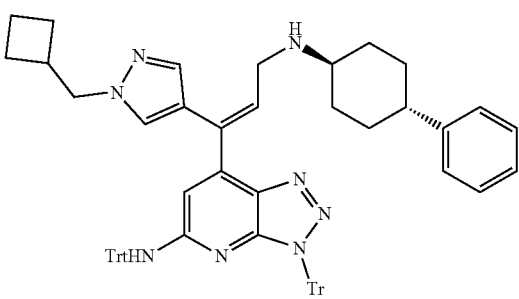

21B was prepared from 21A, Intermediate 2 and Intermediate 4 following the methods described in procedures 16A, 16B and 16C. MS (ESI): m/z 967.4 (M+H).

Example 21. 21B was dissolved in MeOH (5 mL) and THF (1 mL) and nickel(II) chloride (5 eq.) was added. The reaction flask was evacuated and backfilled with Ar 3×, then NaBH$_4$ (8 eq.) was added at 0° C. under a stream of Ar. The reaction mixture was stirred for 1 hour at 0° C., then quenched with ammonium chloride and diluted with aq. NaOH and EtOAc. The aq. phase was extracted 3× with EtOAc. The combined organics were washed with brine, dried with Na$_2$SO$_4$, filtered and concentrated to yield 7-(1-(1-(cyclobutylmethyl)-1H-pyrazol-4-yl)-3-(((1 r,4r)-4-phenylcyclohexyl)amino)propyl)-N,3-ditrityl-3H-[1,2,3]triazolo[4,5-b]pyridin-5-amine, as a yellow oil. MS (ESI): m/z 969.4 (M+H). Deprotection of the trityl groups with TFA/triethylsilane as previously described provided the title compound. MS (ESI): m/z 485.2 (M+H). $^1$H NMR (500 MHz, DMSO-d$_6$) δ 7.68 (s, 1H), 7.47 (s, 1H), 7.15-7.33 (m, 5H), 6.58-6.70 (m, 1H), 3.99-4.14 (m, J=7.00 Hz, 2H), 3.48-3.63 (m, 2H), 3.33-3.45 (m, 2H), 3.00-3.18 (m, 2H), 2.84-2.95 (m, 2H), 0.80-2.15 (m, 14H). HPLC retention time: 1.34 min (Method C).

Example 22. 7-[1-(1H-Pyrazol-4-yl)-3-{[trans-4-phenylcyclohexyl]amino}propyl]-3H-[1,2,3]triazolo[4,5-b]pyridin-5-amine, 2 TFA

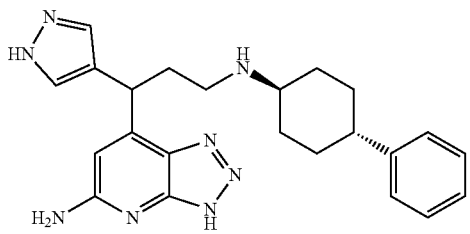 [SMILES: Nc1cc(C(CCN[C@H]2CC[C@H](c3ccccc3)CC2)c2cn[nH]c2)c2nn[nH]c2n1]

22A. (Z)-tert-butyl 4-(3-oxo-1-(3-trityl-5-(tritylamino)-3H-[1,2,3]triazolo[4,5-b]pyridin-7-yl)prop-1-en-1-yl)-1H-pyrazole-1-carboxylate

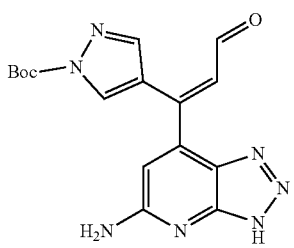 [SMILES: CC(C)(C)OC(=O)n1cc(/C(=C\C=O)c2cc(N)nc3[nH]nnc23)cn1]

22A was prepared in two steps from tert-butyl 4-(4,4,5,5-tetramethyl-1,3,2-dioxaborolan-2-yl)-1H-pyrazole-1-carboxylate and Intermediate 2 via Suzuki coupling and subsequent MnO$_2$ oxidation, following the methods described for 16A and 16B. MS (ESI): m/z 840.2 (M+H).

22B. 7-((Z)-3-((trans-4-Phenylcyclohexyl)amino)-1-(1H-pyrazol-4-yl)prop-1-en-1-yl)-N,3-ditrityl-3H-[1,2,3]triazolo[4,5-b]pyridin-5-amine

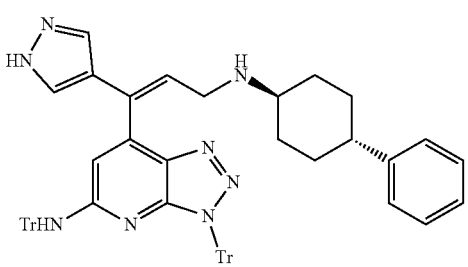

22B was prepared from 22A using the method described for 16C. MS (ESI): m/z 899.4 (M+H).

Example 22 was prepared from 22B in two steps by reduction with NiCl$_2$/NaBH$_4$ followed by deprotection with TFA/triethylsilane using the methods described for Ex. 21. MS (ESI)z: 417.3 m/z (M+H). HPLC retention time: 1.06 min (Method C).

Example 23. 7-[1-(1-Cyclopentyl-1H-pyrazol-4-yl)-3-{[trans-4-phenylcyclohexyl]amino}propyl]-3H-[1,2,3]triazolo[4,5-b]pyridin-5-amine, 2TFA

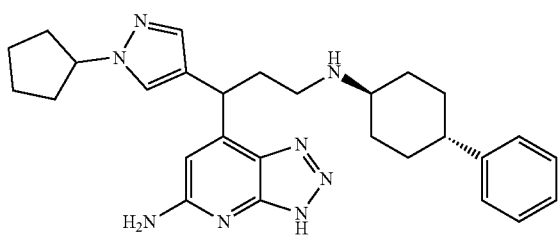 [SMILES: Nc1cc(C(CCN[C@H]2CC[C@H](c3ccccc3)CC2)c2cnn(C3CCCC3)c2)c2nn[nH]c2n1]

23A. 1-Cyclopentyl-4-(4,4,5,5-tetramethyl-1,3,2-dioxaborolan-2-yl)-1H-pyrazole

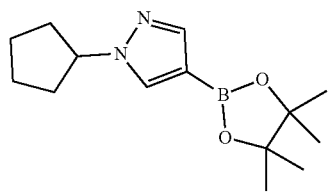 [SMILES: CC1(C)OB(c2cnn(C3CCCC3)c2)OC1(C)C]

23A was prepared using the method described for 20A substituting bromocyclopentane for bromocyclobutane. MS (ESI): m/z 263.0 (M+H).

Example 23 was prepared from 23A, Intermediate 2 and Intermediate 4 following the methods described in procedures 16A, 16B, 16C followed by reduction and deprotection as described for the conversion of 21B into Ex. 21. MS (ESI): m/z 485.3 (M+H). $^1$H NMR (500 MHz, DMSO-$d_6$) δ 7.70 (s, 1H), 7.47 (s, 1H), 7.13-7.33 (m, 5H), 6.27-6.44 (m, 1H), 4.55-4.72 (m, J=7.20, 7.20 Hz, 1H), 4.28-4.46 (m, J=7.70, 7.70 Hz, 1H), 3.04-3.17 (m, 1H), 2.83-2.96 (m, 2H), 2.40-2.49 (m, 4H), 1.98-2.22 (m, 4H), 1.80-1.92 (m, 4H), 1.71-1.80 (m, 2H), 1.57-1.67 (m, 2H), 1.26-1.54 (m, 4H). HPLC retention time: 1.34 min (Method C).

Example 24. 7-{1-[1-(Naphthalen-1-ylmethyl)-1H-pyrazol-4-yl]-3-{[trans-4-phenylcyclohexyl]amino}propyl}-3H-[1,2,3]triazolo[4,5-b]pyridin-5-amine, 2TFA

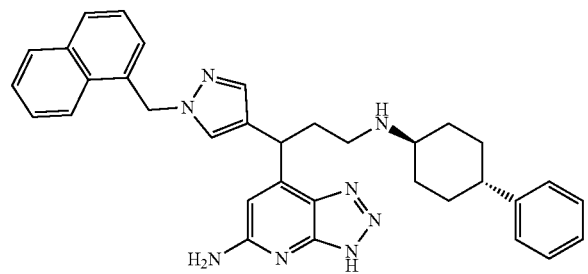 [SMILES: Nc1cc(C(CCN[C@H]2CC[C@H](c3ccccc3)CC2)c2cnn(Cc3cccc4ccccc34)c2)c2nn[nH]c2n1]

24A. 1-(Naphthalen-1-ylmethyl)-4-(4,4,5,5-tetramethyl-1,3,2-dioxaborolan-2-yl)-1H-pyrazole

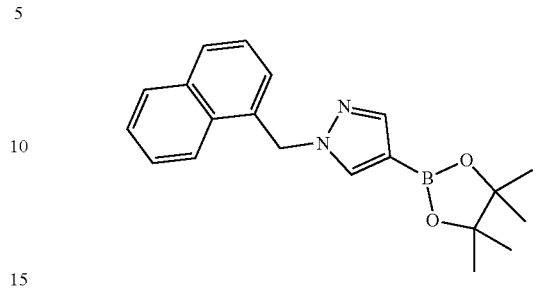

24A was prepared using the method described for 19A substituting naphthalen-1-ylmethanol for (4-chlorophenyl)methanol. MS (ESI): m/z 334.0 (M+H).

Example 24 was prepared from 24A using the steps described for the synthesis of Ex. 23 from 23A. MS (ESI): m/z 557.4 (M+H). $^1$H NMR (500 MHz, CD$_3$OD) δ 7.99-8.06 (m, 1H), 7.86-7.96 (m, 2H), 7.62-7.68 (m, 2H), 7.44-7.58 (m, 3H), 7.27-7.38 (m, 3H), 7.15-7.25 (m, 3H), 6.40-6.59 (m, 1H), 5.75-5.88 (m, 2H), 4.42-4.54 (m, 1H), 3.04-3.18 (m, 1H), 2.88-3.01 (m, 2H), 2.59-2.69 (m, 1H), 2.42-2.57 (m, 2H), 1.85-2.13 (m, 4H), 1.48-1.48 (m, 1H), 1.36-1.63 (m, 4H). HPLC retention time: 1.53 min (Method C).

Example 25. 7-[1-(1-{[3-(Difluoromethoxy)phenyl]methyl}-1H-pyrazol-4-yl)-3-{[trans-4-phenylcyclohexyl]amino}propyl]-3H-[1,2,3]triazolo[4,5-b]pyridin-5-amine, 2TFA

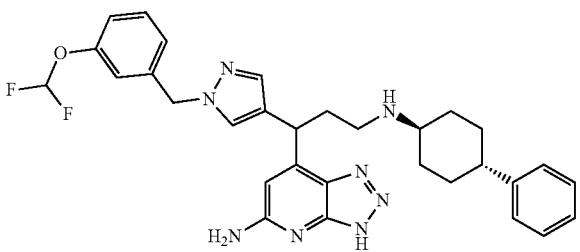 [SMILES: Nc1cc(C(CCN[C@H]2CC[C@H](c3ccccc3)CC2)c2cnn(Cc3cccc(OC(F)F)c3)c2)c2nn[nH]c2n1]

Example 25 was prepared as described for Ex. 24 substituting (3-(difluoromethoxy)phenyl)methanol for naphthalen-1-ylmethanol in step 24A. MS (ESI): m/z 573.4 (M+H). $^1$H NMR (500 MHz, CD$_3$OD) δ 7.79-7.83 (m, 1H), 7.63-7.69 (m, 1H), 7.35-7.43 (m, 1H), 7.16-7.32 (m, 5H), 7.04-7.13 (m, 2H), 6.94-6.98 (m, 1H), 6.61-6.95 (m, 1H), 6.52-6.58 (m, 1H), 5.35 (s, 2H), 4.48-4.58 (m, 1H), 3.01-3.21 (m, 3H), 2.69-2.79 (m, 1H), 2.46-2.63 (m, 2H), 2.11-2.25 (m, 2H), 1.94-2.06 (m, 2H), 1.42-1.68 (m, 4H). HPLC retention time: 1.46 min (Method C).

Example 26. 7-(1-{1-[(3,5-Difluorophenyl)methyl]-1H-pyrazol-4-yl}-3-{[trans-4-phenylcyclohexyl]amino}propyl)-3H-[1,2,3]triazolo[4,5-b]pyridin-5-amine, 2TFA

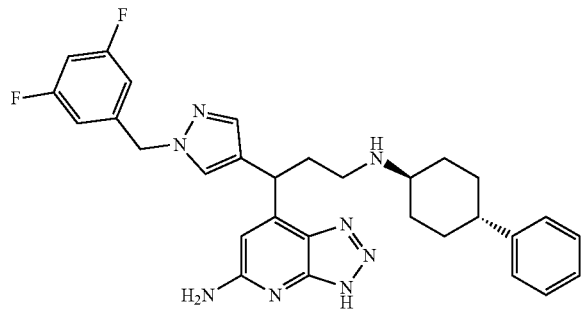 [SMILES: Nc1cc(C(CCN[C@H]2CC[C@H](c3ccccc3)CC2)c2cnn(Cc3cc(F)cc(F)c3)c2)c2nn[nH]c2n1]

Example 26 was prepared as described for Ex. 24 substituting (3,5-difluorophenyl)methanol for naphthalen-1-yl-methanol in step 24A. MS (ESI): m/z 543.3 (M+H). $^1$H NMR (500 MHz, DMSO-$d_6$) δ 8.33-8.58 (m, 2H), 7.83 (s, 1H), 7.56 (s, 1H), 7.27-7.32 (m, 2H), 7.22 (s, 4H), 6.79-6.90 (m, 2H), 6.28-6.45 (m, 1H), 5.33 (s, 2H), 4.33-4.49 (m, 1H), 2.73-3.16 (m, 4H), 2.34-2.66 (m, 2H), 1.97-2.10 (m, 2H), 1.79-1.90 (m, 2H), 1.31-1.58 (m, 4H). HPLC retention time: 1.43 min (QC ACN/TFA).

Example 27. 7-{1-[1-(3,3-Difluorocyclopentyl)-1H-pyrazol-4-yl]-3-{[trans-4-phenylcyclohexyl]amino}propyl}-3H-[1,2,3]triazolo[4,5-b]pyridin-5-amine, 2TFA

27A. 3-(4-Iodo-1H-pyrazol-1-yl)cyclopentanone

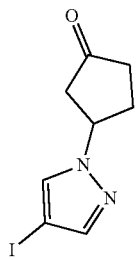 [SMILES: O=C1CCC(n2cc(I)cn2)C1]

4-iodo-1H-pyrazole (400 mg, 2.06 mmol), cyclopent-2-enone (254 mg, 3.09 mmol) and scandium(III) chloride (62.4 mg, 0.412 mmol) were added to anhydrous DCM (10 mL). The reaction mixture was stirred at rt under Ar for 4 hours, then concentrated to remove the solvent. The product was the purified by silica gel chromatography to provide 27A (0.55 g, 96%), as a clear oil. MS (ESI): m/z 277.0 (M+H).

27B. 1-(3,3-Difluorocyclopentyl)-4-iodo-1H-pyrazole

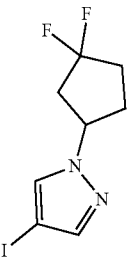

3-(4-iodo-1H-pyrazol-1-yl)cyclopentanone (545 mg, 1.97 mmol) was dissolved in anhydrous DCM (10 mL) at 0° C. DAST (0.782 mL, 5.92 mmol) was added dropwise, and the reaction mixture was allowed to warm to rt then stirred overnight under Ar. Reaction mixture was quenched with 1.5M KH$_2$PO$_4$ solution and extracted 3× with EtOAc. The combined organics were washed with brine, dried with sodium sulfate, filtered and concentrated. The product was purified by silica gel chromatography to provide 23B (223 mg, 0.748 mmol, 37.9%), as a clear oil. MS (ESI): m/z 299.0 (M+H).

27C. 1-(3,3-Difluorocyclopentyl)-4-(4,4,5,5-tetramethyl-1,3,2-dioxaborolan-2-yl)-1H-pyrazole

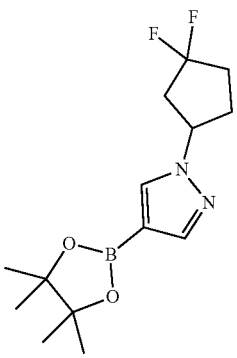 [SMILES: CC1(C)OB(c2cnn(C3CCC(F)(F)C3)c2)OC1(C)C]

27B (0.240 mL, 0.748 mmol) was dissolved in THF (5 mL) at 0° C. A solution of iPrMgCl (1.3 M in THF, 0.921 mL, 1.20 mmol) was added dropwise over 2 min, then the reaction mixture was stirred under Ar for 1 h. A solution of 2-methoxy-4,4,5,5-tetramethyl-1,3,2-dioxaborolane (296 mg, 1.87 mmol) in THF (2 mL) was added in one portion at 0° C., and the reaction mixture was stirred at rt for 1 h, then quenched with saturated aq. NH$_4$Cl. The reaction mixture was diluted with EtOAc and water. The aq. phase was extracted 3× with EtOAc. The combined organic phases were washed with brine, dried with Na$_2$SO$_4$, filtered and concentrated. The product was the purified by silica gel chromatography to provide 27C (70 mg, 31%), as a clear oil. MS (ESI): m/z 299.2 (M+H).

Example 27 was prepared from 27C using the steps outlined above for the synthesis of Ex. 23 from 23A. MS (ESI): m/z 521.3 (M−H)$^−$. $^1$H NMR (500 MHz, CD$_3$OD) δ 7.80 (s, 1H), 7.65 (s, 1H), 7.28 (d, J=7.43 Hz, 2H), 7.23 (d, J=1.38 Hz, 3H), 6.61-6.68 (m, 1H), 4.48-4.60 (m, 1H), 3.14-3.24 (m, 1H), 3.04-3.14 (m, 2H), 2.68 (s, 3H), 2.51-2.63 (m, 3H), 2.31-2.49 (m, 2H), 2.12-2.29 (m, 4H), 1.96-2.04 (m, 2H), 1.42-1.70 (m, 4H). HPLC retention time: 1.32 min (Method C).

Examples 28 and 29. 7-{1-[1-(2,2-Difluorocyclobutyl)-1H-pyrazol-4-yl]-3-{[trans-4-phenylcyclohexyl]amino}propyl}-3H-[1,2,3]triazolo[4,5-b]pyridin-5-amine, 2TFA and 7-(3-{[trans-4-phenylcyclohexyl]amino}-1-[1-(2,2,3-trifluorocyclobutyl)-1H-pyrazol-4-yl]propyl)-3H-[1,2,3]triazolo[4,5-b]pyridin-5-amine, 2TFA

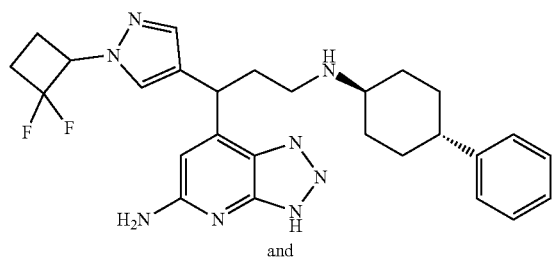

and

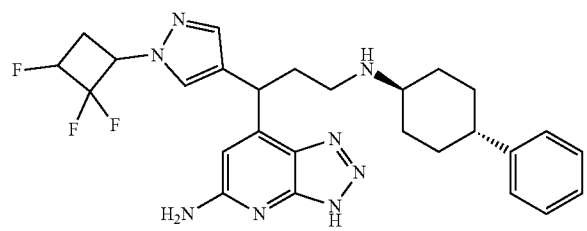

28A. 4-(4,4,5,5-Tetramethyl-1,3,2-dioxaborolan-2-yl)-1-(3,4,4-trifluorocyclobut-2-en-1-yl)-1H-pyrazole

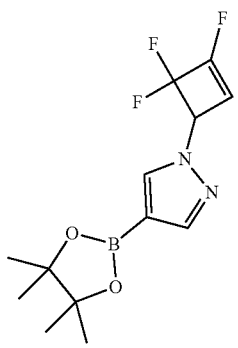 [SMILES: CC1(C)OB(c2cnn(C3C=C(F)C3(F)F)c2)OC1(C)C]

4-(4,4,5,5-Tetramethyl-1,3,2-dioxaborolan-2-yl)-1H-pyrazole (200 mg, 1.03 mmol) and 3-chloro-1,1,2,2-tetrafluorocyclobutane (251 mg, 1.55 mmol) were dissolved in DMF (5 mL). NaH (60% in oil, 41.2 mg, 1.03 mmol) was added carefully at 0° C., then the reaction mixture was allowed to warm to rt and stirred overnight. The reaction mixture was quenched with saturated aq. NH$_4$Cl, and diluted with EtOAc, then washed 3× with 10% aq. LiCl, and brine, dried with Na$_2$SO$_4$, filtered and concentrated. The product was purified by silica gel chromatography to provide 29A (30 mg, 9.7%) as a white solid. MS (ESI): m/z 301.1 (M+H).

Examples 28 and 29 were prepared from 28A, Intermediate 2 and Intermediate 4 following the methods described in procedures 16A, 16B, 16C followed by reduction and deprotection as described for the conversion of 15D into Ex. 15. Separation by prep RP-HPLC provided Example 28 MS (ESI): m/z 507.3 (M+H). $^1$H NMR (500 MHz, CD$_3$OD) δ7.85-7.89 (m, 1H), 7.66-7.70 (m, 1H), 7.13-7.34 (m, 6H), 6.47-6.55 (m, 1H), 5.18-5.32 (m, 1H), 4.48-4.61 (m, 1H), 3.03-3.27 (m, 3H), 2.37-2.64 (m, 5H), 2.12-2.25 (m, 2H), 1.96-2.07 (m, 2H), 1.44-1.71 (m, 4H), 1.32-1.42 (m, 2H). HPLC retention time: 1.25 min (Method C), and Example 29 MS (ESI): m/z 525.3 (M+H). $^1$H NMR (500 MHz, CD$_3$OD) δ 7.88-7.92 (m, 1H), 7.69-7.73 (m, 1H), 7.13-7.35 (m, 6H), 6.48-6.57 (m, 1H), 5.17-5.38 (m, 1H), 4.52-4.63 (m, 1H), 3.03-3.23 (m, 3H), 2.69-2.98 (m, 3H), 2.48-2.66 (m, 2H), 2.13-2.24 (m, 2H), 1.85-2.04 (m, 3H), 1.43-1.68 (m, 4H). HPLC retention time: 1.28 min (Method C).

Example 30. 7-(3-{[trans-4-Phenylcyclohexyl]amino}-1-[1-(3,3,3-trifluoropropyl)-1H-pyrazol-4-yl]propyl)-3H-[1,2,3]triazolo[4,5-b]pyridin-5-amine, 2TFA

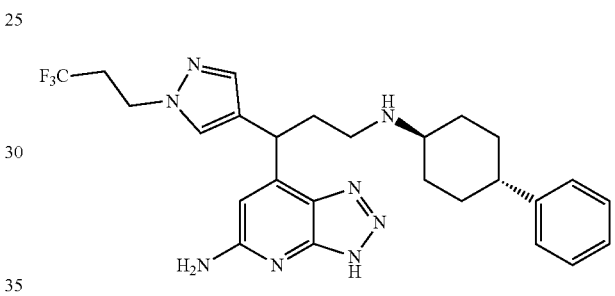

30A. 4-(4,4,5,5-Tetramethyl-1,3,2-dioxaborolan-2-yl)-1-(3,3,3-trifluoropropyl)-1H-pyrazole

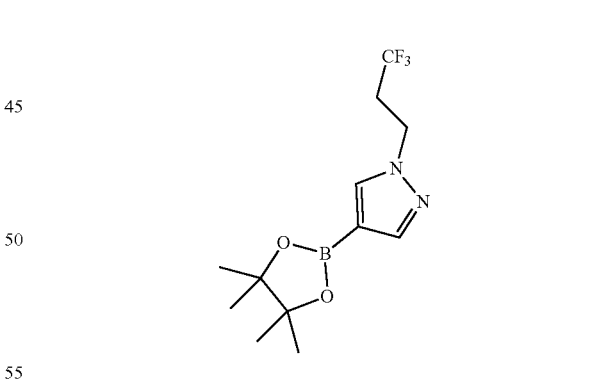

30A was prepared using the method described for 19A substituting 3,3,3-trifluoropropan-1-ol for (4-chlorophenyl)methanol. MS (ESI): m/z 291.2 (M+H).

Example 30 was prepared from 30A using the steps described for the synthesis of Ex. 23 from 23A. MS (ESI): m/z 513.3 (M+H). $^1$H NMR (500 MHz, CD$_3$OD) δ 7.74-7.77 (m, 1H), 7.62-7.65 (m, 1H), 7.25-7.35 (m, 1H), 7.13-7.24 (m, 1H), 6.44-6.55 (m, 1H), 4.49-4.56 (m, 1H), 4.37-4.45 (m, 1H), 3.02-3.22 (m, 3H), 2.68-2.84 (m, 3H), 2.47-2.62 (m, 2H), 2.11-2.24 (m, 2H), 1.88-2.00 (m, 2H), 1.41-1.67 (m, 4H). HPLC retention time: 1.28 min (Method C).

Example 31. 7-(3-{[trans-4-Phenylcyclohexyl]amino}-1-(1-{[3-(trifluoromethyl)phenyl]methyl}-1H-pyrazol-4-yl)propyl)-3H-[1,2,3]triazolo[4,5-b]pyridin-5-amine, 2TFA

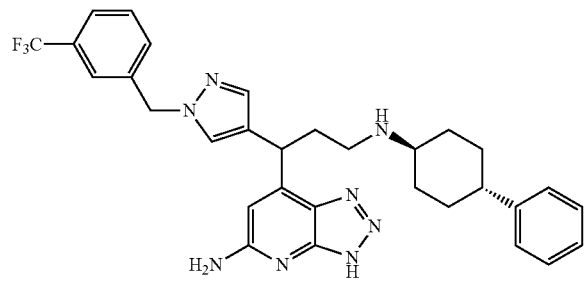 [SMILES: Nc1cc(C(CCN[C@H]2CC[C@H](c3ccccc3)CC2)c2cnn(Cc3cccc(C(F)(F)F)c3)c2)c2nn[nH]c2n1]

Example 31 was prepared as described for Example 30 substituting (3-(difluoromethoxy)phenyl)methanol for 3,3,3-trifluoropropan-1-ol in step 30A. MS (ESI): m/z 575.1 (M+H). $^1$H NMR (500 MHz, CD$_3$OD) δ 7.87 (s, 1H), 7.68 (s, 1H), 7.43-7.64 (m, 4H), 7.06-7.32 (m, 5H), 6.72 (s, 1H), 5.43 (s, 2H), 4.50-4.65 (m, 1H), 3.05-3.22 (m, 3H), 2.73-2.78 (m, 1H), 2.49-2.64 (m, 2H), 2.08-2.21 (m, 2H), 1.90-2.02 (m, 2H), 1.42-1.67 (m, 4H). HPLC retention time: 1.64 min (Method C).

Example 32. 7-[1-(1-Cyclopropyl-1H-pyrazol-4-yl)-3-{[trans-4-phenylcyclohexyl]amino}propyl]-3H-[1,2,3]triazolo[4,5-b]pyridin-5-amine, 2TFA

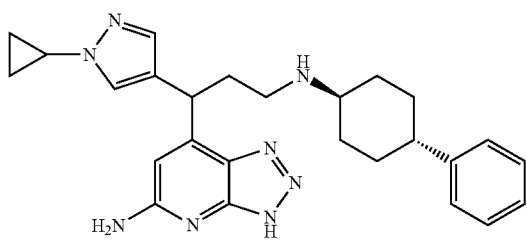 [SMILES: Nc1cc(C(CCN[C@H]2CC[C@H](c3ccccc3)CC2)c2cnn(C3CC3)c2)c2nn[nH]c2n1]

Example 32 was prepared using the steps outlined for the conversion of 23A into Example 23 substituting commercially available 1-cyclopropyl-4-(4,4,5,5-tetramethyl-1,3,2-dioxaborolan-2-yl)-1H-pyrazole for 23A. MS (ESI): m/z 457.4 (M+H). $^1$H NMR (500 MHz, CD$_3$OD) δ 7.79 (s, 1H), 7.58 (s, 1H), 7.28 (d, J=7.43 Hz, 2H), 7.14-7.24 (m, 3H), 6.66 (s, 1H), 4.49-4.60 (m, 1H), 3.59-3.68 (m, 1H), 3.14-3.25 (m, 1H), 3.10 (s, 2H), 2.72 (s, 1H), 2.49-2.64 (m, 1H), 2.13-2.27 (m, 2H), 1.95-2.07 (m, 2H), 1.46-1.72 (m, 5H), 0.98-1.14 (m, 4H) HPLC retention time: 1.32 min (Method D).

Examples 33A and 33B. 7(S)-[1-(1-{[3-(Difluoromethoxy)phenyl]methyl}-1H-pyrazol-4-yl)-3-{[trans-4-phenylcyclohexyl]amino}propyl]-3H-[1,2,3]triazolo[4,5-b]pyridin-5-amine, 2TFA and 7(R)-[1-(1-{[3-(Difluoromethoxy)phenyl]methyl}-1H-pyrazol-4-yl)-3-{[trans-4-phenylcyclohexyl]amino}propyl]-3H-[1,2,3]triazolo[4,5-b]pyridin-5-amine Chiral separation of racemic Example 25 (Chiralpak AD-H column eluted with 25% EtOH-0.1% DEA/75% CO$_2$ mobile phase) provided the single enantiomers 33A (first eluting peak) and 33B (second eluting peak). Each enantiomer was further purified by prep RP-HPLC to provide the pure enantiomers in >99% ee. Example 33A (S-enantiomer): MS (ESI): m/z 573.3 (M+H)$^1$H NMR (500 MHz, CD$_3$OD) δ 7.80 (s, 1H), 7.64 (s, 1H), 7.34 (t, J=8.0 Hz, 1H), 7.29-7.22 (m, 2H), 7.21-7.17 (m, 2H), 7.17-7.13 (m, 1H), 7.09-7.03 (m, 2H), 6.91 (br t, J=1.9 Hz, 1H), 6.67 (s, 1H), 5.32 (s, 2H), 4.55 (dd, J=8.3, 7.2 Hz, 1H), 3.20-3.10 (m, 1H), 3.06 (t, J=8.0 Hz, 2H), 2.77-2.61 (m, 1H), 2.61-2.45 (m, 2H), 2.19-2.09 (m, 2H), 2.00-1.92 (m, 2H), 1.65-1.52 (m, 2H), 1.52-1.40 (m, 2H). Analytical HPLC retention time: 5.81 min (Method A).

Example 33B (R-enantiomer): MS (ESI): m/z 573.4 (M+H). $^1$H NMR (500 MHz, CD$_3$OD) δ 7.83 (s, 1H), 7.66 (s, 1H), 7.36 (t, J=8.0 Hz, 1H), 7.31-7.23 (m, 2H), 7.22-7.19 (m, 2H), 7.19-7.14 (m, 1H), 7.11-7.05 (m, 2H), 6.93 (br t, J=1.9 Hz, 1H), 6.72 (s, 1H), 5.33 (s, 2H), 4.57 (dd, J=8.5, 6.9 Hz, 1H), 3.21-3.11 (m, 1H), 3.08 (t, J=8.1 Hz, 2H), 2.77-2.62 (m, 1H), 2.62-2.50 (m, 2H), 2.22-2.10 (m, 2H), 2.01-1.93 (m, 2H), 1.67-1.54 (m, 2H), 1.54-1.43 (m, 2H). Analytical HPLC retention time: 5.81 min (Method A). Absolute stereochemistry was assigned based on X-ray crystal structure of Example 33B co-crystallized with MPO.

Example 34. 7-[1-(Pyridin-3-yl)-3-{[trans-4-phenyl-cyclohexyl]amino}propyl]-3H-[1,2,3]triazolo[4,5-b]pyridin-5-amine, 2TFA

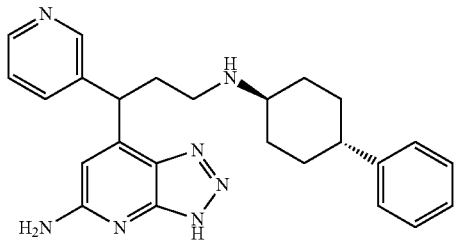 [SMILES: Nc1cc(C(CCN[C@H]2CC[C@H](c3ccccc3)CC2)c2cccnc2)c2nn[nH]c2n1]

34A. (Z)-3-(Pyridin-3-yl)-3-(3-trityl-5-(tritylamino)-3H-[1,2,3]triazolo[4,5-b]pyridin-7-yl)prop-2-en-1-ol

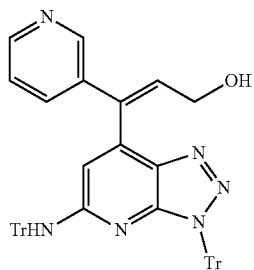

Intermediate 2 (200 mg, 0.249 mmol), pyridin-3-ylboronic acid (36.8 mg, 0.299 mmol), Cs$_2$CO$_3$ (244 mg, 0.748 mmol) and PdCl$_2$(dppf) (37 mg, 0.050 mmol) were dissolved in THF (1.8 mL)/water (1.8 mL) in a pressure-rated vial. The mixture was bubbled with Ar, then heated behind a blast shield at 80° C. overnight. The reaction mixture was diluted with EtOAc and water. The aq. phase was washed 3× with EtOAc, and the combined organic phases were washed with brine, dried with Na$_2$SO$_4$, filtered and concentrated. The product was the purified by silica gel chromatography to provide 34A (0.15 g, 80%) MS (ESI) 753.5 (M+H).

34B. (E)-3-(Pyridin-3-yl)-3-(3-trityl-5-(tritylamino)-3H-[1,2,3]triazolo[4,5-b]pyridin-7-yl)acrylaldehyde

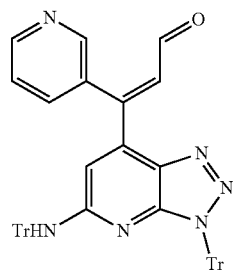

To a solution of 34A (151 mg, 0.200 mmol) dissolved in DCM (4.0 mL) was added MnO$_2$ (296 mg, 3.40 mmol), and the reaction mixture was stirred at rt under Ar for 48 h. Reaction mixture was filtered through a pad of Celite®, and the filtrate evaporated to give 34B as a yellow oil (155 mg, 103%) which was used without purification in the next step.

34C. 7-((Z)-3-((trans-4-Phenylcyclohexyl)amino)-1-(pyridin-3-yl)prop-1-en-1-yl)-N,3-ditrityl-3H-[1,2,3]triazolo[4,5-b]pyridin-5-amine

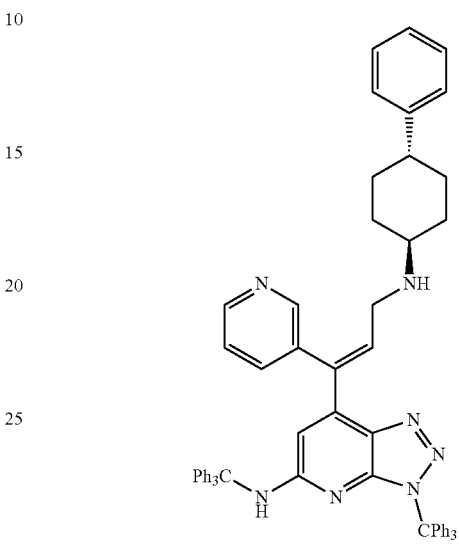

To a mixture of 34B (75 mg, 0.10 mmol) and Ti(OiPr)$_4$ (0.035 mL, 0.12 mmol) in EtOH (5.0 mL) was added Intermediate 4 (23.3 mg, 0.110 mmol), and the mixture was stirred at rt overnight. NaCNBH$_3$ (7.53 mg, 0.120 mmol) was added. Reaction mixture was stirred overnight, then diluted with EtOAc and 1N NaOH. The aq. phase was extracted 3× with EtOAc. The combined organics were dried over Na$_2$SO$_4$ and concentrated to give the crude product, 34C which was taken on to the next step without purification.

Example 34. TFA (1 mL) was added to a solution of 34C (90 mg, 0.099 mmol) in DCM (4 mL). After stirring at rt for 2 h, triethylsilane (0.016 mL, 0.099 mmol) was added, and the mixture was concentrated. The residue was triturated with hexane, then redissolved in a 10:1 mixture of EtOH and EtOAc and was stirred over 10% Pd/C (21 mg, 0.020 mmol) under a hydrogen balloon overnight. Fresh catalyst was added, and the mixture was again stirred overnight under 1 atm H$_2$. Catalyst was removed by filtration through a pad of Celite®, and the filtrate was evaporated. Purification by prep RP-HPLC provided the title compound. MS (ESI): m/z 428.3 (M+H). $^1$H NMR (500 MHz, CD$_3$OD) δ 8.70 (d, J=1.9 Hz, 1H), 8.45 (dd, J=4.7, 1.4 Hz, 1H), 8.03 (d, J=8.0 Hz, 1H), 7.43 (dd, J=7.8, 4.8 Hz, 1H), 7.32-7.08 (m, 5H), 6.51 (s, 1H), 4.60 (t, J=7.7 Hz, 1H), 3.09-2.96 (m, 3H), 2.89 (d, J=5.8 Hz, 1H), 2.66-2.57 (m, 1H), 2.56-2.48 (m, 1H), 2.12 (t, J=12.7 Hz, 2H), 1.95 (d, J=13.5 Hz, 2H), 1.60-1.51 (m, 2H), 1.50-1.40 (m, 2H). HPLC retention time: 1.01 min (Method C).

Example 35. 4-(1-{5-Amino-3H-[1,2,3]triazolo[4,5-b]pyridin-7-yl}-3-{[trans-4-phenylcyclohexyl]amino}propyl)-1,2-dihydropyridin-2-one, 2TFA

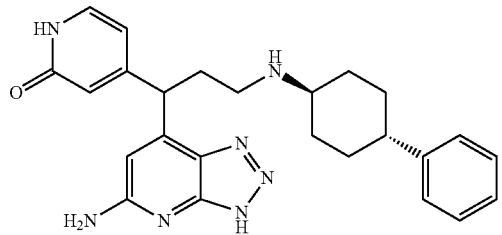 [SMILES: Nc1cc(C(CCN[C@H]2CC[C@H](c3ccccc3)CC2)c2cc[nH]c(=O)c2)c2nn[nH]c2n1]

35A. 7-((E)-1-(2-Methoxypyridin-4-yl)-3-((trans-4-phenylcyclohexyl)amino)prop-1-en-1-yl)-N,3-ditrityl-3H-[1,2,3]triazolo[4,5-b]pyridin-5-amine

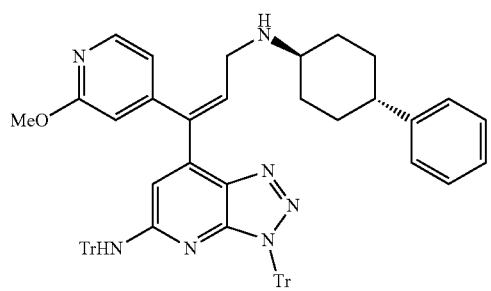

35A was prepared using the procedures described for 34C substituting (2-methoxypyridin-4-yl)boronic acid for pyridin-3-ylboronic acid in step 34A. MS (ESI): m/z 941.1 (M+H).

35B. 7-((E)-1-(2-Methoxypyridin-4-yl)-3-((trans-4-phenylcyclohexyl)amino)prop-1-en-1-yl)-3H-[1,2,3]triazolo[4,5-b]pyridin-5-amine, 3 TFA

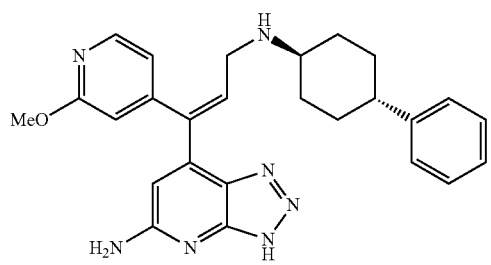 [SMILES: COc1cc(/C(=C\CN[C@H]2CC[C@H](c3ccccc3)CC2)c2cc(N)nc3[nH]nnc23)ccn1]

35A (70 mg, 0.075 mmol) was dissolved in MeOH (1.0 mL) and HCl (4M in dioxane) (1 mL, 4 mmol) was added. The reaction mixture was stirred at rt overnight, then evaporated and purified by prep RP-HPLC to provide 35B (18.4 mg, 30.9%) as a colorless solid. MS (ESI): 456.5 (M+H).

35C. 7-(1-(2-Methoxypyridin-4-yl)-3-((trans-4-phenylcyclohexyl)amino)propyl)-3H-[1,2,3]triazolo[4,5-b]pyridin-5-amine, 3TFA

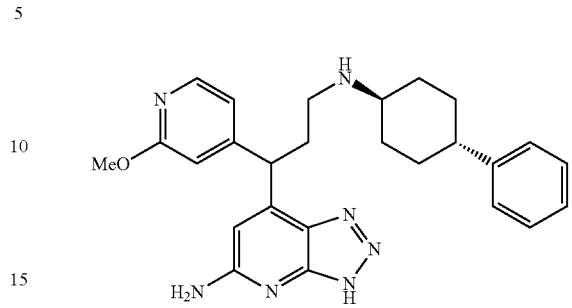

To a degassed solution of 35B (23 mg, 0.028 mmol) in EtOH (10 mL) was added 10% Pd/C (6.06 mg, 5.69 µmol). The reaction stirred under 55 psi $H_2$ for 48 h. Catalyst was removed by filtration through a pad of Celite® which was washed with MeOH. The filtrate was evaporated, and the product purified by prep RP-HPLC to provide 35C (10.1 mg, 44.4%). MS (ESI): m/z 458.5 (M+H).

Example 35. A mixture of 35C (10.1 mg, 0.013 mmol), MeOH (0.50 mL) and HCl (4M in dioxane) (3.00 mL, 12.0 mmol) was heated in a sealed tube with stirring at 100° C. for 1 h. The reaction mixture was cooled to ambient temperature, diluted with MeOH and evaporated. Purification by prep RP-HPLC provided the title compound (2.5 mg, 30%) MS (ESI): m/z 444.6 (M+H). $^1$H NMR (400 MHz, $CD_3OD$) δ 7.43 (d, J=6.8 Hz, 1H), 7.30-7.14 (m, 6H), 6.69 (d, J=1.5 Hz, 1H), 6.66 (s, 1H), 6.53 (dd, J=6.8, 1.8 Hz, 1H), 4.46 (t, J=7.7 Hz, 1H), 3.22-3.02 (m, 3H), 2.87-2.75 (m, 1H), 2.66-2.50 (m, 2H), 2.18 (d, J=5.5 Hz, 2H), 1.98 (dd, J=10.3, 2.6 Hz, 2H), 1.66-1.45 (m, 5H). Analytical HPLC retention time: 6.68 min (Method A).

Example 36. 7-[1-(1H-Pyrazol-3-yl)-3-{[trans-4-phenylcyclohexyl]amino}propyl]-3H-[1,2,3]triazolo[4,5-b]pyridin-5-amine, 2TFA

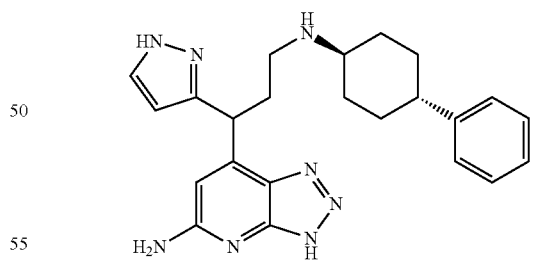

Example 36 was prepared using the steps outlined for the conversion of 23A into Example 23 substituting commercially available 1-(tetrahydro-2H-pyran-2-yl)-3-(4,4,5,5-tetramethyl-1,3,2-dioxaborolan-2-yl)-1H-pyrazole for 23A. MS (ESI): m/z 418.2 (M+H). $^1$H NMR (500 MHz, $CD_3OD$) δ 7.67-7.72 (m, 1H), 7.11-7.32 (m, 6H), 6.43-6.47 (m, 1H), 6.37-6.40 (m, 1H), 4.74-4.81 (m, 1H), 3.08-3.22 (m, 4H), 2.69-2.73 (m, 1H), 2.49-2.62 (m, 1H), 2.14-2.27 (m, 2H), 1.96-2.05 (m, 2H), 1.47-1.71 (m, 4H), 1.17-1.43 (m, 1H). HPLC retention time: 1.09 min (Method C).

Example 37. 3-{[4-(1-{5-Amino-3H-[1,2,3]triazolo[4,5-b]pyridin-7-yl}-3-({4-phenylbicyclo[2.2.2]octan-1-yl}amino)propyl)-1H-pyrazol-1-yl]methyl}phenol, 2TFA

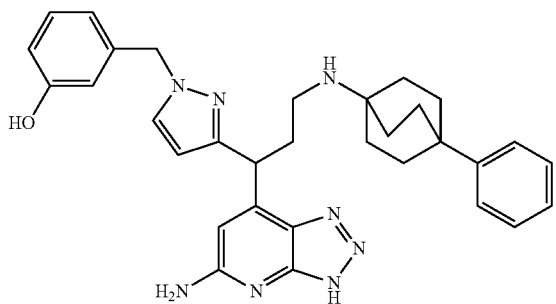 [SMILES: Nc1cc(C(CCNC23CCC(c4ccccc4)(CC2)CC3)c2ccn(Cc3cccc(O)c3)n2)c2nn[nH]c2n1]

37A. (Z)-7-(3-((4-Phenylbicyclo[2.2.2]octan-1-yl)amino)-1-(1-(3-(((triisopropylsilyl)oxy)benzyl)-1H-pyrazol-4-yl)prop-1-en-1-yl)-N,3-ditrityl-3H-[1,2,3]triazolo[4,5-b]pyridin-5-amine

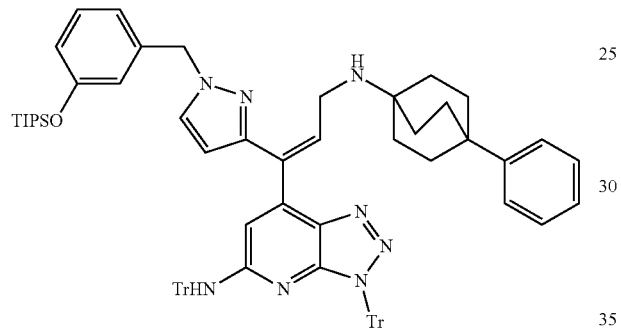

Intermediate 5 (104 mg, 0.439 mmol) was added to a solution of Intermediate 7 (400 mg, 0.399 mmol) in THF (4 mL), and the mixture was stirred at rt for 10 min. Na(OAc)$_3$BH (101 mg, 0.479 mmol) was added in one portion, and the reaction mixture was stirred at rt overnight. The reaction mixture was partitioned between EtOAc and brine, and the aqueous layer extracted 2× with EtOAc. The combined extracts were washed with brine and dried over Na$_2$SO$_4$, filtered and evaporated. The product was the purified by silica gel chromatography to provide 37A (273 mg, 57.6%) as a grey solid. MS (ESI): m/z 1187.5 (M+H).

37B. (Z)-3-((4-(3-((4-Phenylbicyclo[2.2.2]octan-1-yl)amino)-1-(3-trityl-5-(tritylamino)-3H-[1,2,3]triazolo[4,5-b]pyridin-7-yl)prop-1-en-1-yl)-1H-pyrazol-1-yl)methyl)phenol

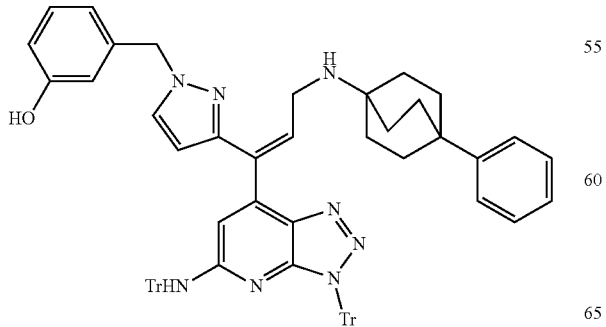

37A (32 mg, 0.027 mmol) was dissolved in THF (1.2 mL), and a 1M solution of TBAF in THF (0.081 mL, 0.081 mmol) was added. The reaction mixture was stirred at rt for 1 h. The reaction mixture was diluted with saturated aq. NaHCO$_3$ and extracted with EtOAc. Extract was dried over Na$_2$SO$_4$, filtered and evaporated to give 37B (23 mg, 83%) as a white solid. MS (ESI): m/z 1032.4 (M+H).

Example 37 was prepared from 37B using the procedures described for the conversion of 16C into Ex. 16. MS (ESI): m/z 549.2 (M+H)). $^1$H NMR (500 MHz, CD$_3$OD) δ 7.88 (s, 1H), 7.68 (s, 1H), 7.24-7.12 (m, 4H), 7.08-7.00 (m, 2H), 6.64-6.55 (m, 3H), 6.48 (br s, 1H), 5.14 (s, 2H), 4.52-4.44 (m, 1H), 2.85 (m, 2H), 2.54-2.48 (m, 1H), 2.43 (m, 1H), 1.89 (m, 6H), 1.77 (m, 6H).

Example 38. (2R)-4-[(3-{5-Amino-3H-[1,2,3]triazolo[4,5-b]pyridin-7-yl}-3-{1-[2-(3-hydroxyphenyl)ethyl]-1H-pyrazol-4-yl}propyl)amino]-1-phenylbicyclo[2.2.2]octan-2-ol, 2TFA

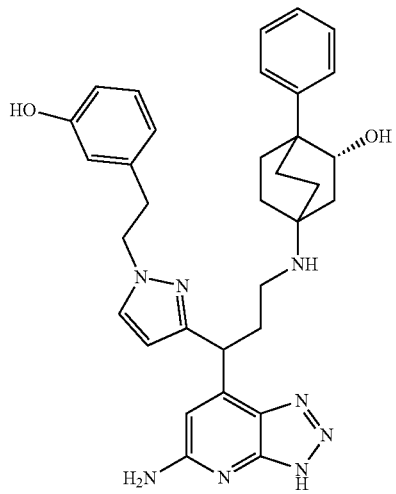 [SMILES: Nc1cc(C(CCNC23CCC(c4ccccc4)(CC2)[C@H](O)C3)c2ccn(CCc3cccc(O)c3)n2)c2nn[nH]c2n1]

38A. 4-(4,4,5,5-Tetramethyl-1,3,2-dioxaborolan-2-yl)-1-(3-((triisopropylsilyl)oxy)-phenethyl)-1H-pyrazole

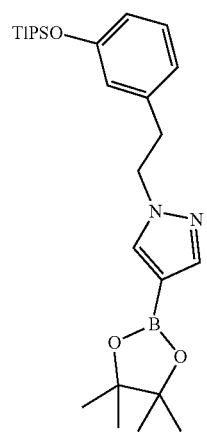

38A was prepared according to the procedures described for Intermediate 6 by substituting methyl 2-(3-hydroxyphenyl)-acetate for methyl 3-hydroxybenzoate in Step A. MS (ESI): m/z 471.2 (M+H).

38B. (Z)-3-(1-(3-((Triisopropylsilyl)oxy)phenethyl)-1H-pyrazol-4-yl)-3-(3-trityl-5-(tritylamino)-3H-[1,2,3]triazolo[4,5-b]pyridin-7-yl)prop-2-en-1-ol

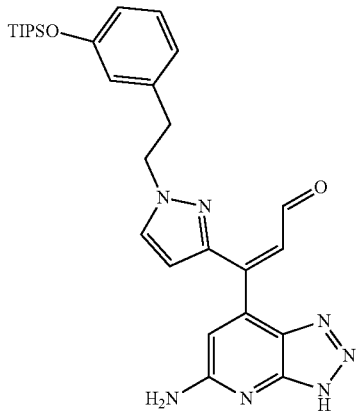

38B was prepared as described for Intermediate 7 substituting 38A for Intermediate 6 in Step A. MS (ESI): m/z 1018.6 (M+H).

Example 38 was prepared from 38B following the steps outlined for Ex. 37 substituting 38B for Intermediate 7 and Intermediate 8 for Intermediate 5 in Step A. MS (ESI): m/z 579.3 (M+H). $^1$H NMR (500 MHz, DMSO-$d_6$) δ 8.53 (br s, 2H), 7.57 (br s, 1H), 7.48 (br s, 1H), 7.32 (br s, 2H), 7.28 (br s, 2H), 7.16 (br s, 1H), 7.00 (br s, 1H), 6.65-6.55 (m, 2H), 6.51 (br s, 1H), 6.36 (br s, 1H), 4.41 (br s, 1H), 4.24 (br s, 2H), 4.12 (br d, J=8.0 Hz, 1H), 3.91 (br s, 1H), 2.96 (br s, 2H), 2.80 (br s, 2H), 2.55 (br s, 1H), 2.31 (br s, 1H), 2.19 (br s, 1H), 1.89 (br s, 1H), 1.84-1.67 (m, 4H), 1.65-1.52 (m, 3H). 2-98% B. (A: H$_2$O+0.05% TFA; B: CH3CN+0.05% TFA)). HPLC retention time: 1.18 min (Method D).

Example 39. (2R)-4-[(3-{5-Amino-3H-[1,2,3]triazolo[4,5-b]pyridin-7-yl}-3-{1-[(3-hydroxyphenyl)methyl]-1H-pyrazol-4-yl}propyl)(2-methoxyethyl)amino]-1-phenylbicyclo[2.2.2]octan-2-ol, 2TFA

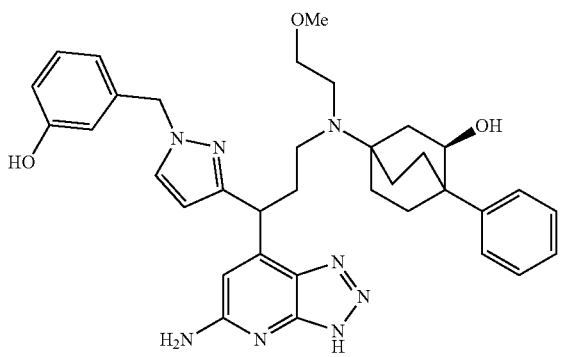 [SMILES: COCCN(CCC(c1ccn(Cc2cccc(O)c2)n1)c1cc(N)nc2[nH]nnc12)C12CCC(c3ccccc3)(CC1)[C@H](O)C2]

39A. (R,Z)-1-Phenyl-4-((3-(1-(3-((triisopropylsilyl)oxy)benzyl)-1H-pyrazol-4-yl)-3-(3-trityl-5-(tritylamino)-3H-[1,2,3]triazolo[4,5-b]pyridin-7-yl)allyl)amino)bicyclo[2.2.2]octan-2-ol

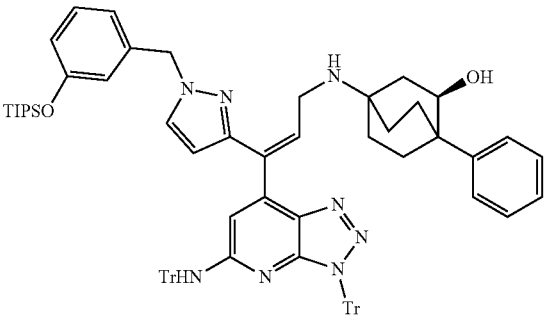

39A was prepared from following the procedure described for 37A substituting Intermediate 8 for Intermediate 5. MS (ESI): m/z 1203.7 (M+H).

39B. (R,Z)-4-((2-Methoxyethyl)(3-(1-(3-((triisopropylsilyl)oxy)benzyl)-1H-pyrazol-4-yl)-3-(3-trityl-5-(tritylamino)-3H-[1,2,3]triazolo[4,5-b]pyridin-7-yl)allyl)amino)-1-phenylbicyclo[2.2.2]octan-2-ol

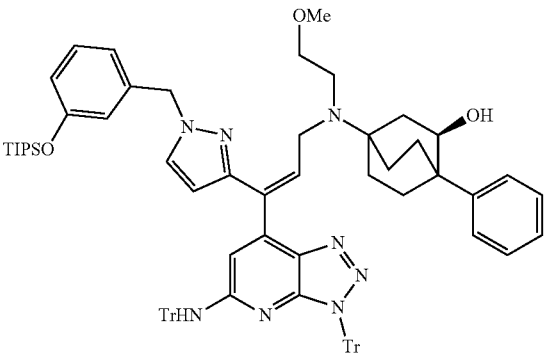

To a solution of 39A (68 mg, 0.056 mmol) in acetonitrile (188 µl) was added K$_2$CO$_3$ (11 mg, 0.079 mmol), KI (0.938 mg, 5.65 µmol) and 1-bromo-2-methoxyethane (7.9 mg, 0.056 mmol). The reaction mixture was stirred at rt for 1 h, then heated to 80° C. in a sealed tube overnight. Additional 1-bromo-2-methoxyethane (39.3 mg, 280 mmol) was added to the reaction mixture, which was again heated overnight at 80° C. The reaction mixture was cooled to rt, filtered and concentrated to provide the crude product 39B (containing some unreacted SM), which was taken forward without purification. MS (ESI): m/z 1262. (M+H).

Example 39 was prepared from 39B by treatment with TBAF to remove the TIPS group following the procedure used for 37B, followed by acid deprotection of the trityl groups and reduction of the double bond as described for the conversion of 16C to Ex. 16. MS (ESI): m/z 623.4 (M+H)). $^1$H NMR (500 MHz, CD$_3$OD) δ 7.88 (s, 1H), 7.68 (s, 1H), 7.24-7.12 (m, 4H), 7.08-7.00 (m, 2H), 6.64-6.55 (m, 3H), 6.48 (br s, 1H), 5.14 (s, 2H), 4.52-4.44 (m, 1H), 2.85 (m, 2H), 2.54-2.48 (m, 1H), 2.43 (m, 1H), 1.89 (m, 6H), 1.77 (m, 6H).

Example 40. 2-[(3-{5-Amino-3H-[1,2,3]triazolo[4,5-b]pyridin-7-yl}-3-{1-[(3-hydroxyphenyl)methyl]-1H-pyrazol-4-yl}propyl) [(3R)-3-hydroxy-4-phenylbicyclo[2.2.2]octan-1-yl]amino]acetamide, 2TFA

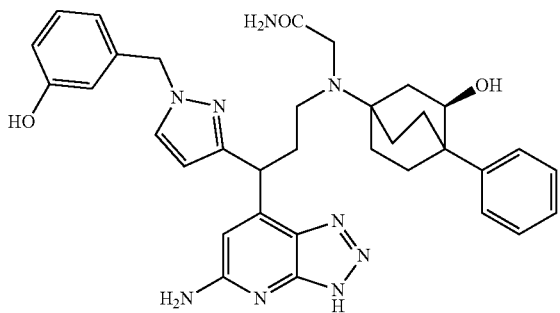 [SMILES: NC(=O)CN(CCC(c1ccn(Cc2cccc(O)c2)n1)c1cc(N)nc2[nH]nnc12)C12CCC(c3ccccc3)(CC1)[C@H](O)C2]

Example 40 was prepared from 39A in a similar manner as described for Ex. 39 substituting 2-bromoacetamide for 1-bromo-2-methoxyethane in step 39B. MS (ESI): m/z 622.2 (M+H). $^1$H NMR (500 MHz, CD$_3$OD) δ 7.82-7.74 (m, 1H), 7.63 (s, 1H), 7.37-7.26 (m, 4H), 7.22-7.16 (m, 1H), 7.14 (t, J=7.8 Hz, 1H), 6.77-6.67 (m, 3H), 6.60 (d, J=1.9 Hz, 1H), 5.24 (s, 2H), 4.54 (br t, J=7.4 Hz, 1H), 4.28 (br d, J=8.3 Hz, 1H), 2.78-2.56 (m, 2H), 2.55-2.44 (m, 1H), 2.44-2.33 (m, 1H), 2.14-1.97 (m, 3H), 1.97-1.88 (m, 3H), 1.87-1.81 (m, 1H), 1.80-1.68 (m, 2H). Three alkyl protons obscured by the solvent peaks. HPLC retention time: 4.83 min (Method A).

Example 41. 3-{[4-(1-{5-Amino-3H-[1,2,3]triazolo[4,5-b]pyridin-7-yl}-3-[(2-hydroxyethyl)({4-phenylbicyclo[2.2.2]octan-1-yl})amino]propyl)-1H-pyrazol-1-yl]methyl}phenol, 2TFA

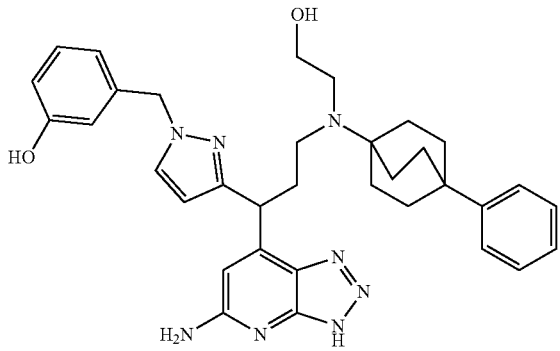 [SMILES: Nc1cc(C(CCN(CCO)C23CCC(c4ccccc4)(CC2)CC3)c2ccn(Cc3cccc(O)c3)n2)c2nn[nH]c2n1]

41A. (Z)-7-(3-((2-((tert-Butyldimethylsilyl)oxy)ethyl)(4-phenylbicyclo[2.2.2]octan-1-yl)amino)-1-(1-(3-((triisopropylsilyl)oxy)benzyl)-1H-pyrazol-4-yl)prop-1-en-1-yl)-N,3-ditrityl-3H-[1,2,3]triazolo[4,5-b]pyridin-5-amine

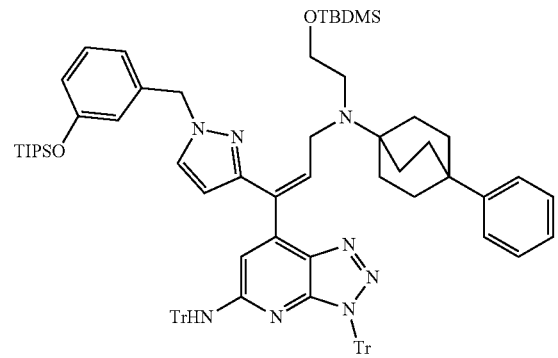

To a solution of 37A (150 mg, 0.13 mmol) in acetonitrile (1.3 mL) was added K$_2$CO$_3$ (44 mg, 0.32 mmol), KI (2.1 mg, 0.013 mmol) and (2-bromoethoxy)(tert-butyl)dimethylsilane (45 mg, 0.19 mmol). The reaction mixture was heated to reflux in a sealed vessel overnight. Additional (2-bromoethoxy)(tert-butyl)dimethylsilane (45 mg, 0.19 mmol) was added to the reaction which was then heated for another 6 h. The reaction mixture was filtered, and the filtrate was concentrate. The product was the purified by silica gel chromatography to provide 41A (98 mg, 58%). MS (ESI): m/z 1346.5 (M+H).

Example 41 was prepared from 41A as described for the conversion of 39B into Ex. 39. MS (ESI): 593.2 (M+H)). $^1$H NMR (500 MHz, CD$_3$OD) δ 7.88 (s, 1H), 7.53 (br s, 1H), 7.20-7.17 (m, 4H), 7.08-6.98 (m, 2H), 6.64-6.54 (m, 3H), 6.50 (br s, 1H), 5.14 (s, 2H), 4.39 (m, 1H), 3.70 (m, 2H), 3.55-3.31 (m, 2H), 3.00 (m, 2H), 2.86-2.77 (m, 1H), 2.67 (m, 1H), 1.89 (m, 12H). HPLC retention time: 1.32 min (Method C).

Example 42. 3-{[4-(1-{5-Amino-3H-[1,2,3]triazolo[4,5-b]pyridin-7-yl}-3-{[(1R,3R,4R)-3-benzyl-4-hydroxycyclopentyl]amino}propyl)-1H-pyrazol-1-yl]methyl}phenol, 2TFA

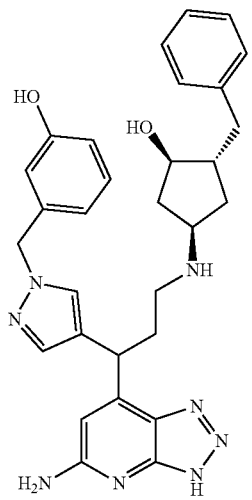 [SMILES: Nc1cc(C(CCN[C@@H]2C[C@@H](Cc3ccccc3)[C@H](O)C2)c2cnn(Cc3cccc(O)c3)c2)c2nn[nH]c2n1]

42A. (1R,2R,4R)-2-Benzyl-4-(((Z)-3-(1-(3-((triisopropylsilyl)oxy)benzyl)-1H-pyrazol-4-yl)-3-(3-trityl-5-(tritylamino)-3H-[1,2,3]triazolo[4,5-b]pyridin-7-yl)allyl)amino)cyclopentanol

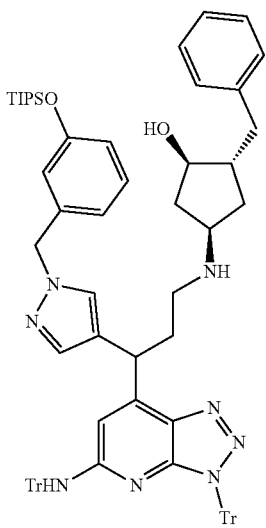

To a solution of Intermediate 7 (0.2 g, 0.2 mmol) in a mixture of THF (2 mL) and EtOH (2 mL) was added TEA (0.25 mL, 1.8 mmol) and Intermediate 9 (0.136 g, 0.599 mmol), and the mixture was heated to 60° C. overnight. The solution was allowed to cool, and NaBH$_4$ (38 mg, 1.0 mmol) was added in one portion. The reaction mixture was stirred at rt for 3 h, then partitioned between EtOAc and brine. The aqueous layer was extracted 2× with EtOAc. The combined extracts were washed with brine and dried over Na$_2$SO$_4$, filtered and evaporated. The product was the purified by silica gel chromatography to provide 42A (125 mg, 53.2%) as a grey solid. MS (ESI): m/z 1178.6 (M+H).

Example 42 was prepared from 42A as described for the conversion of 39B into Ex. 39. MS (ESI): m/z 539.3 (M+H). $^1$H NMR (500 MHz, DMSO-d$_6$) δ 7.68 (br s, 1H), 7.45 (br s, 1H), 7.28 (br s, 2H), 7.17 (br s, 3H), 7.08 (br s, 1H), 6.66 (br d, J=7.3 Hz, 1H), 6.57 (br s, 4H), 6.34 (br s, 1H), 5.16 (br s, 2H), 4.35 (br s, 1H), 3.62 (br s, 1H), 2.84 (br d, J=13.1 Hz, 1H), 2.64 (br s, 2H), 2.55 (br s, 1H), 2.44 (br s, 1H), 2.39-2.23 (m, 2H), 2.16 (br s, 1H), 2.08 (br s, 1H), 1.64-1.44 (m, 2H), 1.40 (br s, 1H). HPLC retention time: 1.10 min (Method C).

Example 43. (3R,4S)-1-(3-{5-Amino-3H-[1,2,3]triazolo[4,5-b]pyridin-7-yl}-3-{1-[(3-hydroxyphenyl)methyl]-1H-pyrazol-4-yl)}propyl)-4-benzylpyrrolidin-3-ol, 2TFA

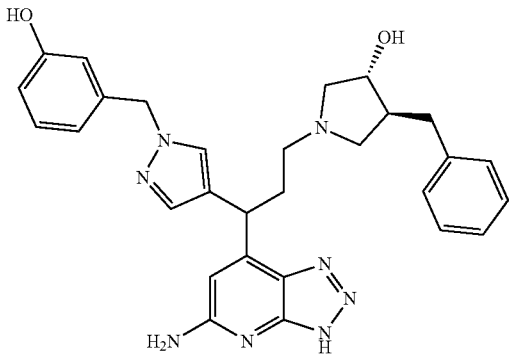 [SMILES: Nc1cc(C(CCN2C[C@H](Cc3ccccc3)[C@@H](O)C2)c2cnn(Cc3cccc(O)c3)c2)c2nn[nH]c2n1]

43A. (3R,4S)-4-benzyl-1-((Z)-3-(1-(3-((triisopropylsilyl)oxy)benzyl)-1H-pyrazol-4-yl)-3-(3-trityl-5-(tritylamino)-3H-[1,2,3]triazolo[4,5-b]pyridin-7-yl)allyl)pyrrolidin-3-ol

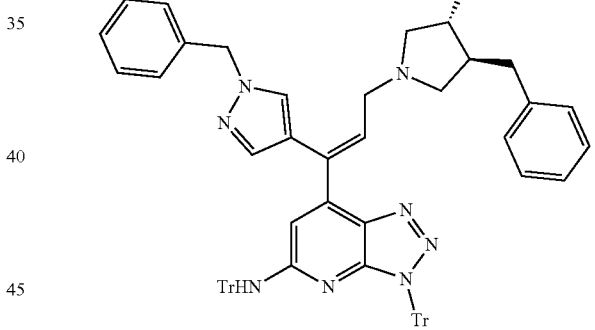

43A was prepared from Intermediate 10 and Intermediate 7 using the procedure described for 37A. MS (ESI): 1163.6 (M+H).

Example 43 was prepared from 43A as described for the conversion of 39B into Ex. 39. MS (ESI): m/z 525.3 (M+H). $^1$H NMR (500 MHz, CD$_3$OD) δ 7.77 (s, 1H), 7.62 (s, 1H), 7.37-7.28 (m, 2H), 7.26-7.19 (m, 3H), 7.14 (t, J=7.8 Hz, 1H), 6.78-6.66 (m, 3H), 6.61 (s, 1H), 5.23 (s, 2H), 4.50 (br t, J=7.7 Hz, 1H), 4.23 (br s, 1H), 3.80 (s, 2H), 3.52 (br s, 1H), 3.22 (br s, 1H), 3.29-3.13 (m, 1H), 2.97-2.79 (m, 2H), 2.75 (br s, 1H), 2.67 (s, 1H), 2.64-2.50 (m, 2H). HPLC retention time: 1.10 min (Method C).

The following additional examples in Table 2 were similarly prepared using procedures described above for examples 1-43.

TABLE 2

| Ex. No. | Compound | NMR | (M + H) |
|---|---|---|---|
| 44 | 7-[1-(5-fluoropyridin-3-yl)-3-{[1r,4r]-4-phenylcyclohexyl]amino}propyl]-3H-[1,2,3]triazolo[4,5-b]pyridin-5-amine | 1H NMR (500 MHz, CD$_3$OD) δ 8.59 (s, 1H), 8.42 (d, J = 2.5 Hz, 1H), 7.91 (d, J = 9.6 Hz, 1H), 7.33-7.14 (m, 5H), 6.61 (s, 1H), 4.65 (t, J = 7.8 Hz, 1H), 3.21-3.13 (m, 1H), 3.11-3.02 (m, 1H), 3.00-2.90 (m 1H) 2.66 (s 1H) 2.59-2.47 (m, 1H), 2.28-2.12 (m, 2H), 2.05-1.93 (m, 2H), 1.68-1.43 (m, 4H), 1.40-1.28 (m, 1H). | 446.2 |
| 45 | 7-[1-(6-fluoropyridin-3-yl)-3-{[1r,4r]-4-phenylcyclohexyl]amino}propyl]-3H-[1,2,3]triazolo[4,5-b]pyridin-5-amine | 1H NMR (500 MHz, CD$_3$OD) δ 8.38 (d, J = 2.2 Hz, 1H), 8.20-8.10 (m, 1H), 7.32-7.24 (m, 2H), 7.23-7.15 (m, 3H), 7.10 (dd, J = 8.5, 2.5 Hz, 1H), 6.58 (s, 1H), 4.61 (t, J = 7.8 Hz, 1H), 3.22-3.12 (m, 1H), 3.10-3.02 (m, 2H), 2.99-2.89 (m, 1H), 2.72-2.61 (m, 1H), 2.61-2.50 (m, 1H), 2.23-2.11 (m, 2H), 1.98 (d, J = 9.1 Hz, 2H), 1.67-1.46 (m, 4H). | 446.3 |
| 46 | 3-{[4-(1-{5-amino-3H-[1,2,3]triazolo[4,5-b]pyridin-7-yl}-3-(benzylamino)propyl)-1H-pyrazol-1-yl]methyl}phenol | 1H NMR (500 MHz CD$_3$OD) δ 7.70 (s, 1H), 7.58 (s, 1H), 7.42 (s, 5H), 7.13 (t, J = 8.0 Hz, 1H), 6.73-6.64 (m, 2H), 6.59 (s, 1H), 6.55 (s, 1H), 5.21 (s, 2H), 4.51 (t, J = 7.8 Hz, 1H), 4.16 (s, 2H), 3.05 (td, J = 10.1, 5.6 Hz, 2H), 2.75-2.66 (m, 1H), 2.65 (s, 1H), 2.59-2.46 (m, 1H). | 455.2 |
| 47 | 3-{[4-(1-{5-amino-3H-[1,2,3]triazolo[4,5-b]pyridin-7-yl}propyl)-1H-pyrazol-1-yl]methyl}phenol | 1H NMR (500 MHz, CD$_3$OD) δ 7.69 (s, 1H), 7.54 (s, 1H), 7.12 (t, J = 7.8 Hz, 1H), 6.79 (s, 1H), 6.69 (dd, J = 8.1, 1.8 Hz, 1H), 6.64 (d, J = 8.0 Hz, 1H), 6.58 (s, 1H), 5.22 (s, 2H), 4.34 (t, J =7.7 Hz, 1H), 2.28 (s, 1H), 2.17 (s, 1H), 0.98 (t, J = 7.4 Hz, 3H). | 350.1 |

TABLE 2-continued

| Ex. No. | Compound | NMR | (M + H) |
|---|---|---|---|
| 48 | 3-{[4-(1-{5-amino-3H-[1,2,3]triazolo[4,5-b]pyridin-7-yl}-3-({[3-(hydroxymethyl)phenyl)]methyl}amino)propyl)-1H-pyrazol-1-yl]methyl}phenol | 1H NMR (500 MHz, CD₃OD) δ 7.67 (s, 1H), 7.54 (s, 1H), 7.42-7.31 (m, 3H), 7.28 (d, J = 3.6 Hz, 1H), 7.13 (t, J = 7.8 Hz, 1H), 6.69 (dd, J = 16.0, 8.0 Hz, 2H), 6.58 (s, 1H), 6.45 (s, 1H), 5.21 (s, 2H), 4.61 (s, 2H), 4.49 (t, J = 7.7 Hz, 1H), 4.05 (s, 2H), 2.97-2.87 (m, 2H), 2.64-2.57 (m, 1H), 2.55-2.43 (m, 1H). | 485.1 |
| 49 | 3-{[4-(1-{5-amino-3H-[1,2,3]triazolo[4,5-b]pyridin-7-yl}-3-{[(3-hydroxyphenyl)methyl)]amino}propyl)-1H-pyrazol-1-yl]methyl}phenol | 1H NMR (500 MHz, CD₃OD) δ 7.71 (s, 1H), 7.57 (s, 1H), 7.22 (t, J = 8.1 Hz, 1H), 7.13 (t, J = 7.8 Hz, 1H), 6.90-6.79 (m, 3H), 6.69 (dd, J = 15.8, 7.6 Hz, 2H), 6.59 (s, 1H), 6.54 (s, 1H), 5.22 (s, 2H), 4.50 (t, J = 7.7 Hz, 1H), 4.07 (s, 2H), 3.09-3.00 (m, 2H), 2.71-2.65 (m, 1H), 2.59-2.48 (m, 1H). | 471.1 |
| 50 | 3-{2-[4-(1-{5-amino-3H-[1,2,3]triazolo[4,5-b]pyridin-7-yl}-3-({4-phenylbicyclo[2.2.2]octan-1-yl}amino)propyl)-1H-pyrazol-1-yl]ethyl}phenol | ¹H NMR (500 MHz, METHANOL-d₄) δ 7.55 (s, 1H), 7.39 (br s, 1H), 7.33-7.21 (m, 4H), 7.15 (br s, 1H), 6.98 (s, 1H), 6.59 (br s, 1H), 6.51 (br d, J = 7.2 Hz, 1H), 6.46 (br s, 1H), 6.37-6.30 (m, 1H), 4.48 (br s, 1H), 4.33 (br s, 2H), 3.08-2.99 (m, 2H), 2.89 (br s, 2H), 2.55 (br s, 1H), 2.43 (br s, 1H), 2.04-1.92 (m, 6H), 1.90-1.68 (m, 6H). | 563.4 |

| Ex. No. | Compound | NMR | (M + H) |
|---|---|---|---|
| 51 | 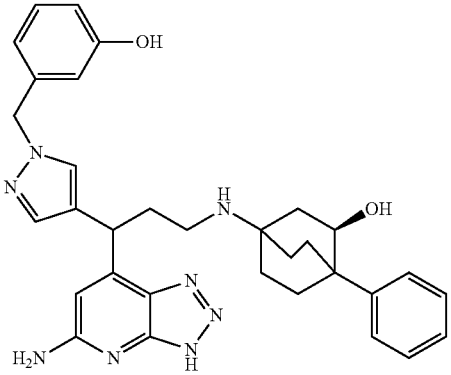<br>(2R)-4-[(3-{5-amino-3H-[1,2,3]triazolo[4,5-b]pyridin-7-yl}-3-{1-[(3-hydroxyphenyl)methyl]-1H-pyrazol-4-yl}propyl)amino]-1-phenylbicyclo[2.2.2]octan-2-ol | 1H NMR (500 MHz, CD$_3$OD) δ 7.77 (s, 1H), 7.62 (s, 1H), 7.39-7.33 (m, 2H), 7.32-7.26 (m, 2H), 7.22-7.16 (m, 1H), 7.16-7.10 (m, 1H), 6.76-6.66 (m, 3H), 6.58 (s, 1H), 5.25 (s, 2H), 4.58 (dd, J = 9.4, 6.1 Hz, 1H), 4.28 (br d, J = 8.8 Hz, 1H), 3.09-2.89 (m, 2H), 2.72-2.61 (m, 1H), 2.56-2.43 (m, 2H), 2.31 (dtd, J = 12.9, 9.9, 3.3 Hz, 1H), 2.08-1.98 (m, 1H), 1.96-1.87 (m, 2H), 1.87-1.77 (m, 2H), 1.77-1.63 (m, 3H). | 565.4 |
| 52 | 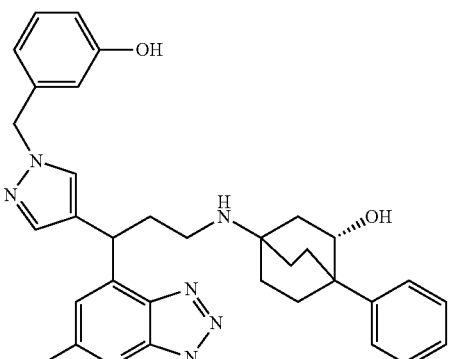<br>(2S)-4-[(3-{5-amino-3H-[1,2,3]triazolo[4,5-b]pyridin-7-yl}-3-{1-[(3-hydroxyphenyl)methyl]-1H-pyrazol-4-yl}propyl)amino]-1-phenylbicyclo[2.2.2]octan-2-ol | 1H NMR (500 MHz, CD$_3$OD) δ 7.77 (s, 1H), 7.62 (s, 1H), 7.38-7.33 (m, 2H), 7.32-7.26 (m, 2H), 7.21-7.16 (m, 1H), 7.14 (t, J = 7.8 Hz, 1H), 6.74-6.66 (m, 3H), 6.58 (s, 1H), 5.25 (s, 2H), 4.58 (dd, J = 9.4, 6.1 Hz, 1H), 4.28 (br d, J = 9.1 Hz, 1H), 3.09-2.87 (m, 2H), 2.71-2.58 (m, 1H), 2.56-2.43 (m, 2H), 2.31 (dtd, J = 12.9, 9.6, 3.3 Hz, 1H), 2.10-1.97 (m, 1H), 1.96-1.87 (m, 2H), 1.86-1.78 (m, 2H), 1.77-1.70 (m, 2H), 1.70-1.64 (m, 1H). | 565.3 |

TABLE 2-continued

| Ex. No. | Compound | NMR | (M + H) |
|---|---|---|---|
| 53 | 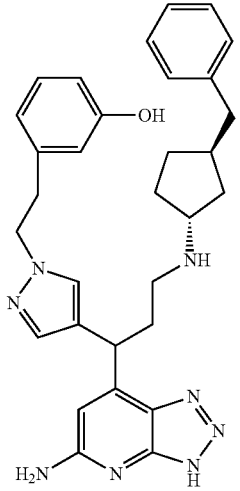<br>3-{2-[4-(1-{5-amino-3H-[1,2,3]triazolo[4,5-b]pyridin-7-yl}-3-{[(1R,3S)-3-benzylcyclopentyl]amino}propyl)-1H-pyrazol-1-yl]ethyl}phenol | 1H NMR (500 MHz, CD$_3$OD) δ 7.55 (s, 1H), 7.35 (s, 1H), 7.29-7.22 (m, 2H), 7.20-7.10 (m, 3H), 6.96 (t, J = 7.8 Hz, 1H), 6.56 (dd, J = 7.6, 2.1 Hz, 1H), 6.49 (d, J = 7.4 Hz, 1H), 6.45-6.36 (m, 2H), 4.42 (dd, J = 9.1, 6.3 Hz, 1H), 4.31 (t, J = 6.7 Hz, 2H), 3.67-3.55 (m, 1H), 3.01 (t, J = 6.7 Hz, 2H), 2.96-2.86 (m, 2H), 2.72-2.65 (m, 1H), 2.64-2.51 (m, 2H), 2.47-2.32 (m, 2H), 2.25-2.10 (m, 1H), 1.93-1.86 (m, 1H), 1.82-1.66 (m, 2H), 1.62-1.48 (m, 1H), 1.43-1.32 (m, 1H). | 537.3 |
| 54 | 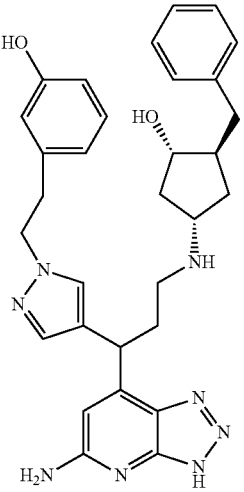<br>3-{2-[4-(1-{5-amino-3H-[1,2,3]triazolo[4,5-b]pyridin-7-yl}-3-{[(1S,3S,4S)-3-benzylcyclopentyl]amino}propyl)-1H-pyrazol-1-yl]ethyl}phenol | 1H NMR (500 MHz, CD$_3$OD) δ 7.55 (s, 1H), 7.35 (s, 1H), 7.29-7.22 (m, 2H), 7.20-7.10 (m, 3H), 6.96 (t, J = 7.8 Hz, 1H), 6.56 (dd, J = 7.6, 2.1 Hz, 1H), 6.49 (d, J = 7.4 Hz, 1H), 6.45-6.36 (m, 2H), 4.42 (dd, J = 9.1, 6.3 Hz, 1H), 4.31 (t, J = 6.7 Hz, 2H), 3.67-3.55 (m, 1H), 3.01 (t, J = 6.7 Hz, 2H), 2.96-2.86 (m, 2H), 2.72-2.65 (m, 1H), 2.64-2.51 (m, 2H), 2.47-2.32 (m, 2H), 2.25-2.10 (m, 1H), 1.93-1.86 (m, 1H), 1.82-1.66 (m, 2H), 1.62-1.48 (m, 1H), 1.43-1.32 (m, 1H). | 553.3 |

TABLE 2-continued

| Ex. No. | Compound | NMR | (M + H) |
|---|---|---|---|
| 55 | 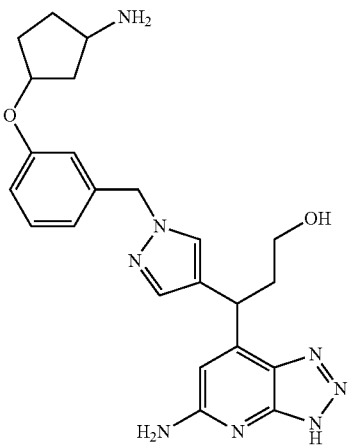 3-{5-amino-3H-[1,2,3]triazolo[4,5-b]pyridin-7-yl}-3-[1-({3-[(3-aminocyclopentyl)oxy]phenyl}methyl)-1H-pyrazol-4-yl]propan-1-ol | 1H NMR (500 MHz, DMSO-$d_6$) δ 7.71 (s, 1H), 7.41 (s, 1H), 7.19 (t, J = 7.93 Hz, 1H), 6.74 (br dd, J = 7.93, 13.73 Hz, 2H), 6.54 (s, 1H), 6.45-6.51 (m, 1H), 6.38 (s, 1H), 5.20 (s, 2H), 4.58 (br s, 1H), 4.39 (br t, J = 7.48 Hz, 1H), 3.26-3.37 (m, 3H), 2.31-2.39 (m, 1H), 2.25-2.31 (m, 1H), 2.15-2.25 (m, 1H), 1.82 (br s, 2H), 1.54 (br d, J = 7.63 Hz, 1H), 1.39-1.47 (m, 1H). | 449.1 |

What is claimed is:

1. A compound of Formula (I):

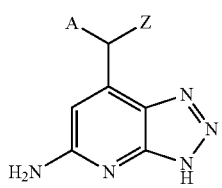

(I)

wherein:

Z is ethyl, propyl, 3-phenylpropyl, 2-benzyloxyethyl, 3,3-diphenylpropyl, 3-cyclohexylpropyl, 1-naphthylpropyl, 2-naphthylpropyl, 1-indanylpropyl, 2-(tetrahydro-2H-pyran-4-yl)ethyl, 2-phenoxyethyl, 3-(1,2,3,4-tetrahydroisoquinolin-1-yl)propyl, 2-benzylaminoethyl,

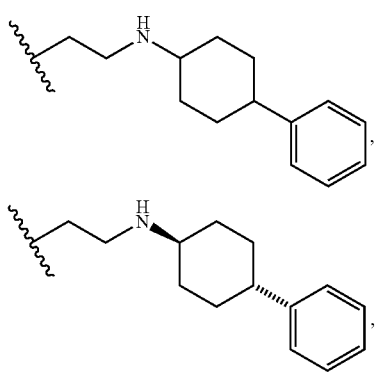

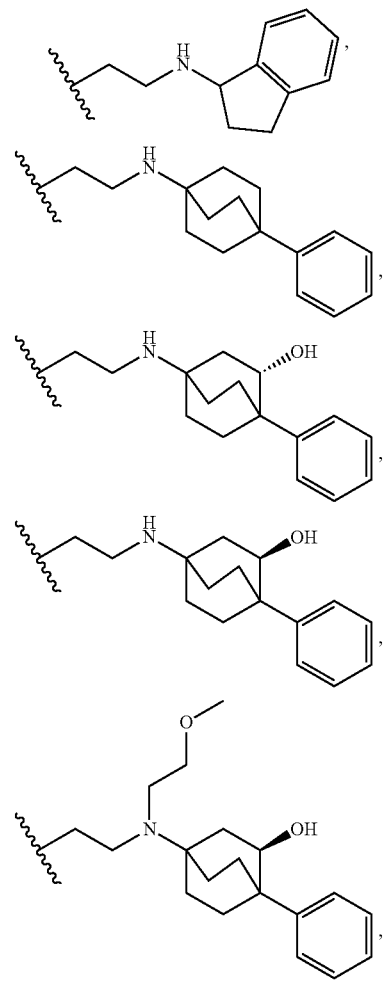

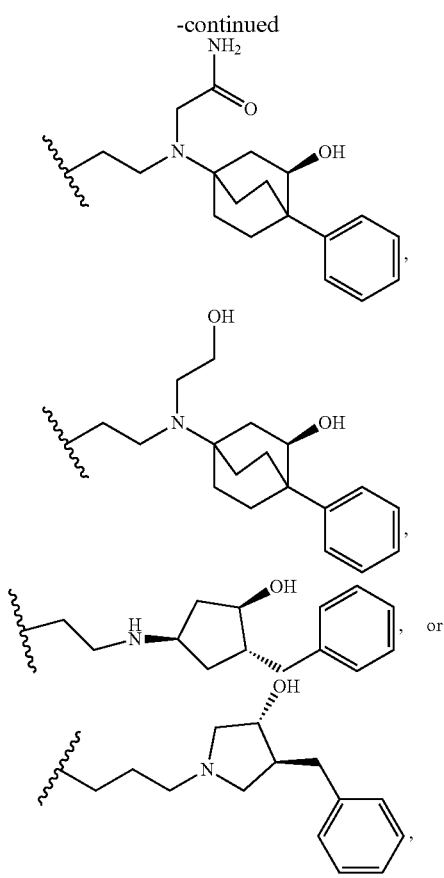

any of which is substituted with 0-3 $R^2$ groups;

$R^2$ is, independently at each occurrence, one or more halogen, hydroxy, cyano, hydroxy $C_1$-$C_6$ alkyl, halo $C_1$-$C_6$ alkyl, $C_1$-$C_6$ alkyl, —$C_{3-6}$ cycloalkyl, aryl, aryloxy, aryl $C_1$-$C_6$ alkyl-, or CONR$^x$R$^y$;

said —$C_{3-6}$ cycloalkyl substituted with 0-3 $R^a$, aryl substituted with 0-4 $R^a$, and 5- to 10-membered heterocycle comprising carbon atoms and 1-4 heteroatoms selected from N, O, and S; wherein said heterocycle is substituted with 0-3 $R^a$;

$R^a$ is, independently at each occurrence, OH, CN, —CONH$_2$, halogen, $C_{1-4}$ alkyl, $C_{1-4}$ alkoxy, $C_{1-4}$ haloalkyl, or $C_{1-4}$ haloalkoxy;

$R^x$ is hydrogen or $C_{1-4}$ alkyl;

$R^y$ is hydrogen or $C_{1-4}$ alkyl;

A is pyrazole, triazole, pyridine or dihydropyridinone optionally substituted with $R^1$;

$R^1$ is hydrogen, halogen, $C_1$-$C_6$ alkyl, $C_1$-$C_6$ alkoxy, aryl $C_1$-$C_6$ alkyl-, halo $C_1$-$C_6$ alkyl-, heterocyclyl $C_1$-$C_6$ alkyl- or $C_3$-$C_8$ cycloalkyl, any of which is substituted with 0-4 $R^3$ groups;

$R^3$ is, independently at each occurrence, one or more halogen, hydroxy, cyano, hydroxy $C_1$-$C_4$ alkyl, halo $C_1$-$C_4$ alkyl, halo $C_1$-$C_4$ alkoxy, $C_3$-$C_6$ cycloalkyl, aryl, aryloxy, aryl $C_1$-$C_4$ alkyl-, —COO—$C_1$-$C_4$ alkyl, CONR$^x$R$^y$, —CO-heterocyclyl, —SO$_2$-aryl or SO$_2$-heteroaryl;

or a pharmaceutically acceptable salt, a stereoisomer, a tautomer, or a solvate thereof.

2. The compound according to claim 1 of Formula (II)

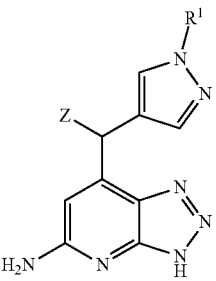

(II)

wherein

Z is ethyl, propyl, 3-phenylpropyl, 2-benzyloxyethyl, 3,3-diphenylpropyl, 3-cyclohexylpropyl, 1-naphthylpropyl, 2-naphthylpropyl, 1-indanylpropyl, 2-(tetrahydro-2H-pyran-4-yl)ethyl, 2-phenoxyethyl, 3-(1,2,3,4-tetrahydroisoquinolin-1-yl)propyl, 2-benzylaminoethyl,

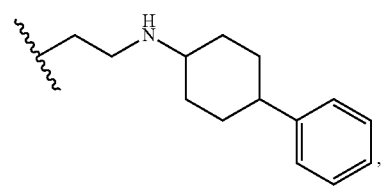

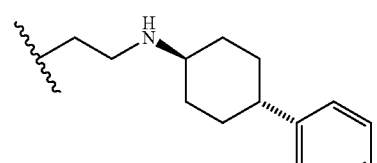

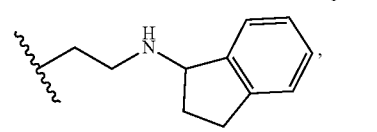

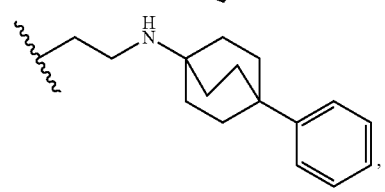

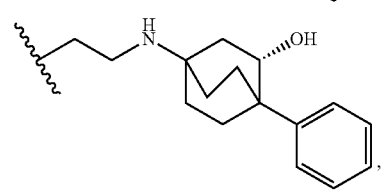

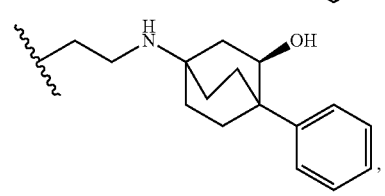

-continued

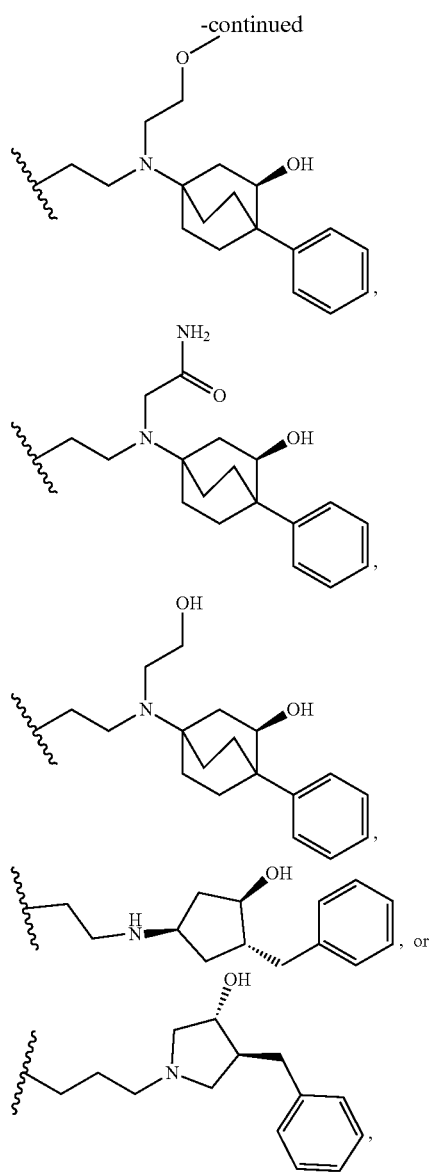

any of which is substituted with 0-3 R² groups;

R² is, independently at each occurrence, one or more halogen, hydroxy, cyano, hydroxy $C_1$-$C_6$ alkyl, halo $C_1$-$C_6$ alkyl, $C_1$-$C_6$ alkyl, —$C_{3-6}$ cycloalkyl, aryl, aryloxy, aryl $C_1$-$C_6$ alkyl-, or CONR$^x$R$^y$;

said —$C_{3-6}$ cycloalkyl substituted with 0-3 R$^a$, aryl substituted with 0-4 R$^a$, and 5- to 10-membered heterocycle comprising carbon atoms and 1-4 heteroatoms selected from N, O, and S; wherein said heterocycle is substituted with 0-3 R$^a$;

R$^a$ is, independently at each occurrence, OH, CN, —CONH$_2$, halogen, $C_{1-4}$ alkyl, $C_{1-4}$ alkoxy, $C_{1-4}$ haloalkyl, or $C_{1-4}$ haloalkoxy;

R$^x$ is hydrogen or $C_{1-4}$ alkyl;
R$^y$ is hydrogen or $C_{1-4}$ alkyl;
R$^1$ is hydrogen, $C_1$-$C_6$ alkyl, $C_1$-$C_6$ alkoxy, aryl $C_1$-$C_6$ alkyl-, halo $C_1$-$C_6$ alkyl-, heterocyclyl $C_1$-$C_6$ alkyl- or $C_3$-$C_8$ cycloalkyl, any of which is substituted with 0-4 R$^3$ groups;

R$^3$ is, independently at each occurrence, one or more halogen, hydroxy, cyano, hydroxy $C_1$-$C_4$ alkyl, halo $C_1$-$C_4$ alkyl, halo $C_1$-$C_4$ alkoxy, $C_3$-$C_6$ cycloalkyl, aryl, aryloxy, aryl $C_1$-$C_4$ alkyl-, —COO—$C_1$-$C_4$ alkyl, CONR$^x$R$^y$, —CO-heterocyclyl, —SO$_2$-aryl or SO$_2$-heteroaryl;

or a pharmaceutically acceptable salt, a stereoisomer, a tautomer, or a solvate thereof.

3. The compound according to claim 2 wherein:

Z is ethyl, propyl, 3-phenylpropyl, 2-benzyloxyethyl, 3,3-diphenylpropyl, 3-cyclohexylpropyl, 1-naphthylpropyl, 2-naphthylpropyl, 1-indanylpropyl, 2-(tetrahydro-2H-pyran-4-yl)ethyl, 2-phenoxyethyl, 3-(1,2,3,4-tetrahydroisoquinolin-1-yl)propyl, 2-benzylaminoethyl,

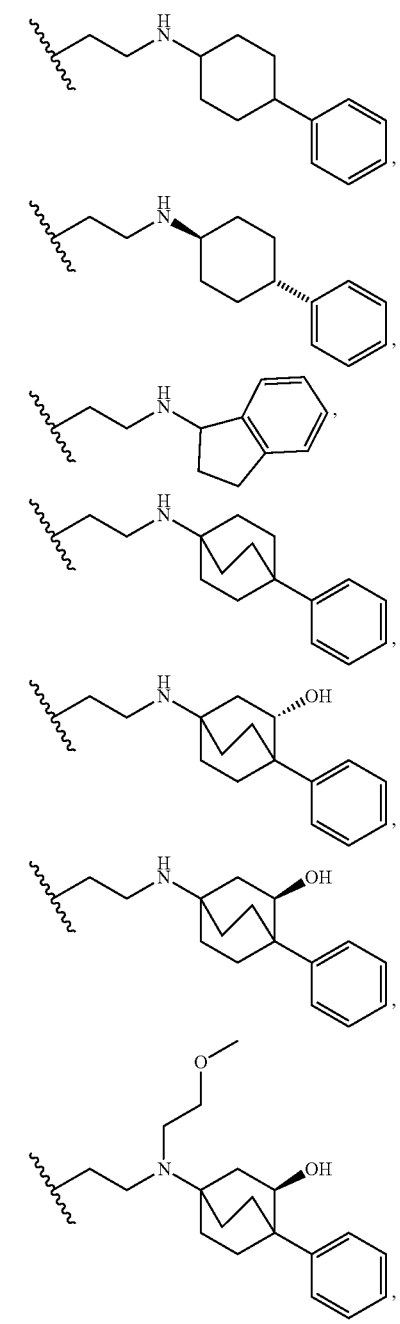

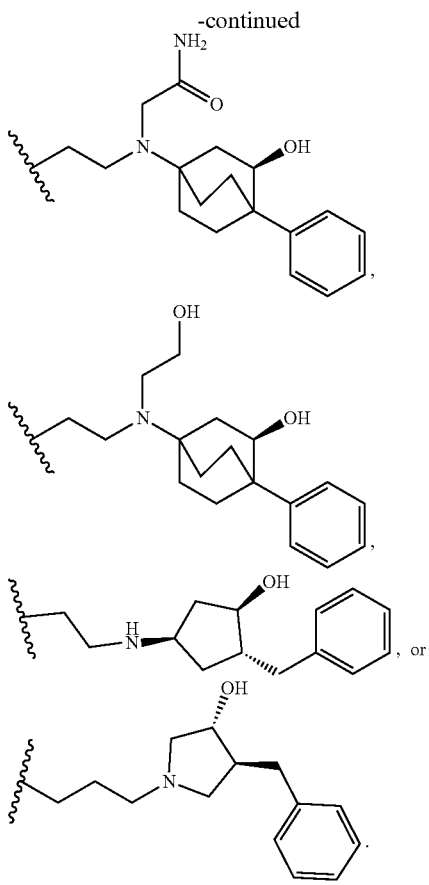

R[1] is H, benzyl, 4-chlorobenzyl, 3-difluoromethoxybenzyl, 3,5-difluorobenzyl, 3-trifluoromethylbenzyl, 3-hydroxybenzyl, 3-hydroxyphenethyl, 3-(4-piperidinyl)benzyl, 1-naphthylmethyl, 3-pyridinylmethyl, 3-2-oxo-1,2-dihydropyridin-4-yl, cyclopropyl, cyclobutyl, cyclobutylmethyl, cyclopentyl, 3,3-difluorocyclopentyl, 2,2-difluorocyclobutyl, 2,2,3-trifluorocyclobutyl, 3,3,3-trifluoropropyl, 3-pyridylmethyl, or 1,2,3,4-tetrahydroisoquinolin-6-yl)methyl;

or a pharmaceutically acceptable salt, a stereoisomer, a tautomer, or a solvate thereof.

4. A compound which is
7-(4-phenyl-1-(1-(((1,2,3,4-tetrahydroisoquinolin-6-yl)methyl)-1H-pyrazol-4-yl)butyl)-3H-[1,2,3]triazolo[4,5-b]pyridin-5-amine, 2 TFA, 7-{1-[1-(1,2,3,4-tetrahydroisoquinolin-6-ylmethyl)-1H-pyrazol-4-yl]butyl}-3H-[1,2,3]triazolo[4,5-b]pyridin-5-amine, 2TFA, 7-(3-(benzyloxy)-1-(1-(((1,2,3,4-tetrahydroisoquinolin-6-yl)methyl)-1H-pyrazol-4-yl)propyl)-3H-[1,2,3]triazolo[4,5-b]pyridin-5-amine, 2TFA, 7-{4,4-diphenyl-1-[1-(1,2,3,4-tetrahydroisoquinolin-6-ylmethyl)-1H-pyrazol-4-yl]butyl}-3H-[1,2,3]triazolo[4,5-b]pyridin-5-amine, 2 TFA, 7-{4-cyclohexyl-1-[1-(1,2,3,4-tetrahydroisoquinolin-6-ylmethyl)-1H-pyrazol-4-yl]butyl}-3H-[1,2,3]triazolo[4,5-b]pyridin-5-amine, 2TFA, 7-[4-(naphthalen-2-yl)-1-[1-(1,2,3,4-tetrahydroisoquinolin-6-ylmethyl)-1H-pyrazol-4-yl]butyl]-3H-[1,2,3]triazolo[4,5-b]pyridin-5-amine, 2TFA, 7-[4-(2,3-dihydro-1H-inden-1-yl)-1-[1-(1,2,3,4-tetrahydroisoquinolin-6-ylmethyl)-1H-pyrazol-4-yl]butyl]-3H-[1,2,3]triazolo[4,5-b]pyridin-5-amine, 2TFA, 7-[4-(Naphthalen-1-yl)-1-[1-(1,2,3,4-tetrahydroisoquinolin-6-ylmethyl)-1H-pyrazol-4-yl]butyl]-3H-[1,2,3]triazolo[4,5-b)]pyridin-5-amine, 2TFA, 7-[3-(Oxan-4-yl)-1-[1-(1,2,3,4-tetrahydroisoquinolin-6-ylmethyl)-1H-pyrazol-4-yl]propyl]-3H-[1,2,3]triazolo[4,5-b]pyridin-5-amine, 2TFA, 7-{3-Phenoxy-1-[1-(1,2,3,4-tetrahydroisoquinolin-6-ylmethyl)-1H-pyrazol-4-yl]propyl}-3H-[1,2,3]triazolo[4,5-b]pyridin-5-amine, 2TFA, 7-{4-Phenyl-1-[1-(pyridin-3-ylmethyl)-1H-pyrazol-4-yl]butyl}-3H-[1,2,3]triazolo[4,5-b]pyridin-5-amine, 2 TFA, 7-[4-Phenyl-1-(1-{[3-(piperidin-4-yl)phenyl]methyl}-1H-pyrazol-4-yl)butyl]-3H-[1,2,3]triazolo[4,5-b]pyridin-5-amine, 2 TFA, 7-[1-(1-Benzyl-1H-pyrazol-4-yl)-4-(1,2,3,4-tetrahydroisoquinolin-1-yl)butyl]-3H-[1,2,3]triazolo[4,5-b]pyridin-5-amine, 2TFA, 7-[3-(Benzylamino)-1-(1-methyl-1H-pyrazol-4-yl)propyl]-3H-[1,2,3]triazolo[4,5-b]pyridin-5-amine, 2 TFA, 7-[1-(1-Benzyl-1H-pyrazol-4-yl)-3-[(4-phenylcyclohexyl)amino]propyl]-3H-[1,2,3]triazolo[4,5-b]pyridin-5-amine, 2TFA, 7-[1-(1-Benzyl-1H-pyrazol-4-yl)-3-[(2,3-dihydro-1H-inden-1-yl)amino]propyl]-3H-[1,2,3]triazolo[4,5-b]pyridin-5-amine, 2TFA, 7-[1-(1-Benzyl-1H-pyrazol-4-yl)-3-1{[trans-4-phenylcyclohexyl]-amino}propyl]-3H-[1,2,3]triazolo[4,5-b]pyridin-5-amine, 2TFA, 7-(1-{1-[(4-Chlorophenyl)methyl]-1H-pyrazol-4-yl}-3-{[trans-4-phenylcyclohexyl]amino}propyl)-3H-[1,2,3]triazolo[4,5-b]pyridin-5-amine, 2TFA, 7-[1-(1-Cyclobutyl-1H-pyrazol-4-yl)-3-{[trans-4-phenylcyclohexyl]amino}propyl]-3H-[1,2,3]triazolo[4,5-b]pyridin-5-amine, 2TFA, 7-{1-[1-(Cyclobutylmethyl)-1H-pyrazol-4-yl]-3-{[trans-4-phenylcyclohexyl]amino}propyl}-3H-[1,2,3]triazolo[4,5-b]pyridin-5-amine, 2TFA, 7-[1-(1H-Pyrazol-4-yl)-3-{[trans-4-phenylcyclohexyl]amino}propyl]-3H-[1,2,3]triazolo[4,5-b]pyridin-5-amine, 2 TFA, 7-[1-(1-Cyclopentyl-1H-pyrazol-4-yl)-3-{[trans-4-phenylcyclohexyl]amino}propyl]-3H-[1,2,3]triazolo[4,5-b]pyridin-5-amine, 2TFA, 7-{1-[1-(Naphthalen-1-ylmethyl)-1H-pyrazol-4-yl]-3-{[trans-4-phenylcyclohexyl]amino}propyl}-3H-[1,2,3]triazolo[4,5-b]pyridin-5-amine, 2TFA, 7-[1-(1-{[3-(Difluoromethoxy)phenyl]methyl}-1H-pyrazol-4-yl)-3-{[trans-4-phenylcyclohexyl]amino}propyl]-3H-[1,2,3]triazolo[4,5-b]pyridin-5-amine, 2TFA, 7-(1-{1-[(3,5-Difluorophenyl)methyl]-1H-pyrazol-4-yl}-3-{[trans-4-phenylcyclohexyl]amino}propyl)-3H-[1,2,3]triazolo[4,5-b]pyridin-5-amine, 2TFA, 7-{1-[1-(3,3-Difluorocyclopentyl)-1H-pyrazol-4-yl]-3-{[trans-4-phenylcyclohexyl]amino}propyl}-3H-[1,2,3]triazolo[4,5-b]pyridin-5-amine, 2TFA, 7-{1-[1-(2,2-Difluorocyclobutyl)-1H-pyrazol-4-yl]-3-{[trans-4-phenylcyclohexyl]amino}propyl}-3H-[1,2,3]triazolo[4,5-b]pyridin-5-amine, 2TFA, 7-(3-{[trans-4-Phenylcyclohexyl]amino}-1-[1-(2,2,3-trifluorocyclobutyl)-1H-pyrazol-4-yl]propyl)-3H-[1,2,3]triazolo[4,5-b]pyridin-5-amine, 2TFA, 7-(3-{[trans-4-Phenylcyclohexyl]amino}-1-[1-(3,3,3-trifluoropropyl)-1H-pyrazol-4-yl]propyl)-3H-[1,2,3]triazolo[4,5-b]pyridin-5-amine, 2TFA, 7-(3-{[trans-4-Phenylcyclohexyl]amino}-1-(1-{[3-(trifluoromethyl)phenyl]methyl}-1H-pyrazol-4-yl)propyl)-3H-[1,2,3]triazolo[4,5-b]pyridin-5-amine, 2TFA, 7-[1-(1-Cyclopropyl-1H-pyrazol-4-yl)-3-{[trans-4-phenylcyclohexyl]amino}propyl]-3H-[1,2,3]triazolo[4,5-b]pyridin-5-amine, 2TFA, 7(S)-[1-(1-{[3-(Difluoromethoxy)phenyl]methyl}-1H-pyrazol-4-yl)-3-{[trans-4-phenylcyclohexyl]amino}propyl]-3H-[1,2,3]triazolo[4,5-b]pyridin-5-amine, 2TFA, 7(R)-[1-(1-{[3-(Difluoromethoxy)phenyl]methyl}-1H-pyrazol-4-yl)-3-{[trans-4-phenylcyclohexyl]amino}propyl]-3H-[1,2,3]triazolo[4,5-b]pyridin-5-amine, 2TFA, 7-[1-(Pyridin-3-yl)-3-{[trans-4-phenylcyclohexyl]amino}propyl]-3H-[1,2,3]triazolo[4,5-b]pyridin-5-amine, 2TFA, 4-(1-{5-Amino-3H-[1,2,3]triazolo[4,5-b]pyridin-7-yl}-3-{[trans-4-phenylcyclohexyl]amino}propyl)-1,2-dihydropyridin-2-one, 2TFA, 7-[1-(1H-Pyrazol-3-yl)-3-{[trans-4-phenylcyclohexyl]amino}propyl]-3H-[1,2,3]triazolo[4,5-b]pyridin-5-amine, 2TFA, 3-{[4-(1-{5-Amino-3H-[1,2,3]triazolo[4,5-b]pyridin-7-yl}-3-({4-phenylbicyclo[2.2.2]octan-1-yl}amino)propyl)-1H-pyrazol-1-yl]methyl}phenol, 2TFA, (2R)-4-[(3-{5-Amino-3H-[1,2,3]triazolo[4,5-b]pyridin-7-yl}-3-{1-[2-(3-hydroxyphenyl)ethyl]-1H-pyrazol-4-yl}propyl)amino]-1-phenylbicyclo[2.2.2]octan-2-ol, 2TFA, (2R)-4-[(3-{5-Amino-3H-[1,2,3]triazolo[4,5-b]pyridin-7-yl}-3-{1-[(3-hydroxyphenyl)methyl]-1H-pyrazol-4-yl}propyl)(2-methoxyethyl)amino]-1-phenylbicyclo[2.2.2]octan-2-ol, 2TFA, 2-[(3-{5-Amino-3H-[1,2,3]triazolo[4,5-b]pyridin-7-yl}-3-{1-[(3-hydroxyphenyl)methyl]-1H-pyrazol-4-yl}propyl)[(3R)-3-hydroxy-4-phenyl-bicyclo[2.2.2]octan-1-yl]amino]acetamide, 2TFA, 3-{[4-(1-{5-Amino-3H-[1,2,3]triazolo[4,5-b]pyridin-7-yl}-3-[(2-hydroxyethyl)({4-phenylbicyclo[2.2.2]octan-1-yl})amino]propyl)-1H-pyrazol-1-yl]methyl}phenol, 2TFA, 3-{[4-(1-{5-Amino-3H-[1,2,3]triazolo[4,5-b]pyridin-7-yl}-3-{[(1R,3R,4R)-3-benzyl-4-hydroxycyclopentyl]amino}propyl)-1H-pyrazol-1-yl]methyl}phenol, 2TFA, (3R,4S)-1-(3-{5-Amino-3H-[1,2,3]triazolo[4,5-b]pyridin-7-yl}-3-{1-[(3-hydroxyphenyl)methyl]-1H-pyrazol-4-yl}propyl)-4-benzylpyrrolidin-3-ol, 2TFA, 7-[1-(5-fluoropyridin-3-yl)-3-{[(1r,4r)-4-phenylcyclohexyl]amino}propyl]-3H-[1,2,3]triazolo[4,5-b]pyridin-5-amine, 7-[1-(6-fluoropyridin-3-yl)-3-{[(1r,4r)-4-phenylcyclohexyl]amino}propyl]-3H-[1,2,3]triazolo[4,5-b]pyridin-5-amine, 3-{[4-(1-{5-amino-3H-[1,2,3]triazolo[4,5-b]pyridin-7-yl}-3-(benzylamino)propyl)-1H-pyrazol-1-yl]methyl}phenol, 3-{[4-(1-{5-amino-3H-[1,2,3]triazolo[4,5-b]pyridin-7-yl}propyl)-1H-pyrazol-1-yl]methyl}phenol, 3-{[4-(1-{5-amino-3H-[1,2,3]triazolo[4,5-b]pyridin-7-yl}-3-({[3-(hydroxymethyl)phenyl]methyl}amino)propyl)-1H-pyrazol-1-yl]methyl}phenol, 3-{[4-(1-{5-amino-3H-[1,2,3]triazolo[4,5-b]pyridin-7-yl}-3-{[(3-hydroxyphenyl)methyl]amino}propyl)-1H-pyrazol-1-yl]methyl}phenol, 3-{2-[4-(1-{5-amino-3H-[1,2,3]triazolo[4,5-b]pyridin-7-yl}-3-({4-phenylbicyclo[2.2.2]octan-1-yl}amino)propyl)-1H-pyrazol-1-yl]ethyl}phenol, (2R)-4-[(3-{5-amino-3H-[1,2,3]triazolo[4,5-b]pyridin-7-yl}-3-{1-[(3-hydroxyphenyl)methyl]-1H-pyrazol-4-yl}propyl)amino]-1-phenylbicyclo[2.2.2]octan-2-ol, (2S)-4-[(3-{5-amino-3H-[1,2,3]triazolo[4,5-b]pyridin-7-yl}-3-{1-[(3-hydroxyphenyl)methyl]-1H-pyrazol-4-yl}propyl)amino]-1-phenylbicyclo[2.2.2]octan-2-ol, 3-{2-[4-(1-{5-amino-3H-[1,2,3]triazolo[4,5-b]pyridin-7-yl}-3-{[(1R,3S)-3-benzylcyclopentyl]amino}propyl)-1H-pyrazol-1-yl]ethyl}phenol, 3-{2-[4-(1-{5-amino-3H-[1,2,3]triazolo[4,5-b]pyridin-7-yl}-3-{[(1S,3S,4S)-3-benzyl-4-hydroxycyclopentyl]amino}propyl)-1H-pyrazol-1-yl]ethyl}phenol, 3-{5-amino-3H-[1,2,3]triazolo[4,5-b]pyridin-7-yl}-3-[1-({3-[(3-aminocyclopentyl)oxy]phenyl}methyl)-1H-pyrazol-4-yl]propan-1-ol, or a pharmaceutically acceptable salt, a stereoisomer, a tautomer, or a solvate thereof.

5. A pharmaceutical composition, comprising a pharmaceutically acceptable carrier and a compound according to claim 1, or a pharmaceutically acceptable salt, a stereoisomer, a tautomer, or a solvate thereof.

* * * * *